United States Patent
Tulshian et al.

(10) Patent No.: US 7,094,784 B2
(45) Date of Patent: Aug. 22, 2006

(54) HIGH AFFINITY LIGANDS FOR NOCICEPTIN RECEPTOR ORL-1

(75) Inventors: Deen Tulshian, Lebanon, NJ (US); Ginny D. Ho, Murray Hill, NJ (US); Lisa S. Silverman, Edison, NJ (US); Julius J. Matasi, Scotch Plains, NJ (US); Robbie L. McLeod, Branchburg, NJ (US); John A. Hey, Nutley, NJ (US); Richard W. Chapman, Somerville, NJ (US); Ana Bercovici, West Orange, NJ (US); Francis M. Cuss, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/761,977

(22) Filed: Jan. 21, 2004

(65) Prior Publication Data
US 2004/0152707 A1   Aug. 5, 2004

Related U.S. Application Data

(62) Division of application No. 10/155,277, filed on May 23, 2002, now Pat. No. 6,716,846, and a division of application No. 09/769,824, filed on Jan. 25, 2001, now Pat. No. 6,455,527, which is a division of application No. 09/359,771, filed on Jul. 26, 1999, now Pat. No. 6,262,066.

(60) Provisional application No. 60/094,240, filed on Jul. 27, 1998.

(51) Int. Cl.
C07D 401/04 (2006.01)
A61K 31/46 (2006.01)

(52) U.S. Cl. ...................... 514/249; 514/259; 514/299; 514/304; 544/283; 544/286; 544/354; 546/112; 546/125; 546/126; 546/127; 546/183

(58) Field of Classification Search ................. 514/299, 514/249, 259, 304; 544/283, 286, 354; 546/112, 546/125, 126, 127, 183
See application file for complete search history.

(56) References Cited

U.S. PATENT DOCUMENTS

| 3,311,624 | A | 3/1967 | Ohnacker et al. |
| 3,318,900 | A | 5/1967 | Janssen |
| 4,521,537 | A | 6/1985 | Kosley et al. |
| 4,526,896 | A | 7/1985 | Scherrer et al. |
| 4,707,487 | A | 11/1987 | Arrang et al. |
| 5,270,324 | A | 12/1993 | Zamboni et al. |
| 5,296,495 | A | 3/1994 | Matsuo et al. |
| 5,352,707 | A | 10/1994 | Pompni et al. |
| 5,436,255 | A | 7/1995 | Butler |
| 5,472,964 | A | 12/1995 | Young et al. |
| 5,489,599 | A | 2/1996 | Carter et al. |
| 5,495,052 | A | * 2/1996 | Shum et al. ................. 568/648 |
| 5,583,000 | A | 12/1996 | Ortiz de Montellano et al. |
| 5,654,316 | A | 8/1997 | Carruthers et al. |
| 5,658,908 | A | 8/1997 | Chang et al. |
| 5,665,719 | A | 9/1997 | Bock et al. |
| 5,698,567 | A | 12/1997 | Guillonneau et al. |

(Continued)

FOREIGN PATENT DOCUMENTS

DE    195 19 245    10/1996

(Continued)

OTHER PUBLICATIONS

Casy et al., Opioid properties of some derivatives of Pethidine based on tropane, J. Pharm. Pharmacol. 44(10), pp. 787-790, 1992.*

(Continued)

*Primary Examiner*—Deepak Rao
(74) *Attorney, Agent, or Firm*—Krishma G. Baneriee; Anita W. Magatti

(57) ABSTRACT

Novel compounds of the formula

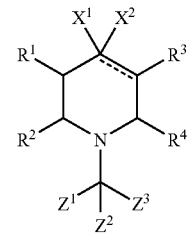

or a pharmaceutically acceptable salt or solvate thereof, wherein:
the dotted line represents an optional double bond;
$X^1$ is optionally substituted alkyl, cycloalkyl, aryl, heteroaryl or heterocycloalkyl;
$X^2$ is —CHO, —CN, optionally substituted amino, alkyl, or aryl;
or $X^1$ is optionally substituted benzofused heterocyclyl and $X^2$ is hydrogen;
or $X^1$ and $X^2$ together form an optionally benzofused spiro heterocyclyl group
$R^1$, $R^2$, $R^3$ and $R^4$ are independently H and alkyl, or ($R^1$ and $R^4$) or ($R^2$ and $R^3$) or ($R^1$ and $R^3$) or ($R^2$ and $R^4$) together can form an alkylene bridge of 1 to 3 carbon atoms;
$Z^1$ is optionally substituted alkyl, aryl, heteroaryl, cycloalkyl or heterocycloalkyl, or —$CO_2$(alkyl or substituted amino) or CN ; $Z^2$ is H or $Z^1$; $Z^3$ is H oralkyl; or $Z^1$, $Z^2$ and $Z^3$, together with the carbon to which they are attached, form bicyclic saturated or unsaturated rings; pharmaceutical compositions therefore, and the use of said compounds as nociceptin receptor inhibitors useful in the treatment of pain, anxiety, cough, asthma, depression and alcohol abuse are disclosed.

6 Claims, 4 Drawing Sheets

U.S. PATENT DOCUMENTS

| | | | |
|---|---|---|---|
| 5,710,155 | A | 1/1998 | Schnorrenberg et al. |
| 5,872,115 | A | 2/1999 | Binet et al. |
| 6,071,925 | A | 6/2000 | Adam et al. |
| 6,277,991 | B1 | 8/2001 | Hohlweg et al. |
| 6,727,254 | B1 * | 4/2004 | Tulshian et al. ....... 514/252.18 |

FOREIGN PATENT DOCUMENTS

| | | |
|---|---|---|
| EP | 0 121 972 | 10/1984 |
| EP | 0 173 516 | 3/1986 |
| EP | 0 199 543 | 10/1986 |
| EP | 0 480 717 | 4/1991 |
| EP | 0 709 375 | 5/1996 |
| EP | 0 743 312 | 11/1996 |
| EP | 0 856 514 | 8/1998 |
| EP | 921 125 | 6/1999 |
| EP | 997464 | 5/2000 |
| GB | 1043141 | 9/1966 |
| JP | 61-225167 | 10/1986 |
| WO | WO 96/26196 | 8/1996 |
| WO | WO 97/28797 | 8/1997 |
| WO | WO 98/52545 | 11/1998 |
| WO | WO 99/36421 | 7/1999 |

OTHER PUBLICATIONS

Rizzi er al, *Life Sciences*, 64, 13 (1999), p. PL157-163.
Ciccocioppo et al, *Psychopharmacology*, 141 (1999), p. 220-224.
Abstract of WO98/54168 Dec. 1998.
Fawzi et al, *Eur. J. Pharmacology*, 336 (1997), p. 233-242.
Bolser et al, *Brit. J. Pharmacology*, 114 (1995), p. 735-738.
West et al, *Molecular Pharmacology*, 38 (1990), p. 610-613.
Leysen et al, *Eur. J. Pharmacology*, 43 (1977), p. 253-267.
Obase et al, *Chem. Pharm. Bull.*, 30 (1982), p. 474-483.
Derwent Abstract No. 86-302680 (for JP 61-225167), 1986.
*Chem. Abstracts* 128:102008, 1998.
*Chem. Abstracts* 119:49233, 1993.
*Chem. Abstracts* 104:186309, 1986.
Henderson et al, *Trends in Pharm. Sci.*, 18 (1997), 293-299.
Urch et al, Chem. Abstract 129:67708 (1998).
Urch et al, Chem. Abstract 129:27892 (1998).
Urch et al, Chem. Abstract 126:104021 (1997).
Nagarathnam et al, Chem. Abstract 125:142759 (1996).
Fernandez Lopez et al, Chem. Abstract 120:270234 (1994).
Glennon, Chem. Abstract 118:225698 (1993).
Casy et al, Chem. Abstract 118:93788 (1993).
Fan et al, Chem. Abstract 115:64561 (1991).
Rao et al, Chem. Abstract 112:158030 (1990).
Ge et al, Chem. Abstract 110:108035 (1989).
Zhou et al, Chem. Abstract 110:18422 (1989).
Ding et al, Chem. Abstract 110:8449 (1989).
Daum et al, Chem. Abstract 83:71489 (1975).
Ohki et al, Chem. Abstract 81:99241 (1974).
Helsley, Chem. Abstract 77:5360 (1972).
Winter, Analgetics, pp. 10-74 (1965).
Stahl et al, *Chem. Abstracts* 88:182462, 1978.

* cited by examiner

HIGH AFFINITY LIGANDS FOR NOCICEPTIN RECEPTOR ORL-1

This application is a divisional of U.S. Ser. No. 10/155,277, filed May 23, 2002 now U.S. Pat. No. 6,716,846 B2, which is a divisional of U.S. Ser. No. 09/769,824, filed Jan. 25, 2001, now U.S. Pat. No. 6,455,527 B2 which is a divisional of U.S. Ser. No. 09/359,771, now U.S. Pat. No. 6,262,066, which claims the benefit of U.S. Provisional Application No. 60/094,240, filed Jul. 27, 1998.

BACKGROUND

The nociceptin receptor ORL-1 has been shown to be involved with modulation of pain in animal models. ORL-1 (the nociceptin receptor) was discovered as an "orphan opioid-like receptor" i.e. a receptor whose ligand was unknown. The nociceptin receptor is a G protein coupled receptor. While highly related in structure to the three classical opioid receptors, i.e. the targets for traditional opioid analgesics, it is not activated by endogenous opioids. Similarly, endogenous opioids fail to activate the nociceptin receptor. Like the classical opioid receptors, the nociceptin receptor has a broad distribution in the central nervous system.

In late 1995, nociceptin was discovered and shown to be an endogenous peptide ligand that activates the nociceptin receptor. Data included in the initial publications suggested that nociceptin and its receptor are part of a newly discovered pathway involved in the perception of painful stimuli. Subsequent work from a number of laboratories has shown that nociceptin, when administered intraspinally to rodents, is an analgesic. The efficacy of nociceptin is similar to that of endogenous opioid peptides. Recent data has shown that nociceptin acts as an axiolytic when administered directly into the brain of rodents. When tested in standard animals models of anxiety, the efficacy of nociceptin is similar to that seen with classical benzodiazapine anxiolytics. These data suggest that a small molecule agonist of the nociceptin receptor could have significant analgesic or anxiolytic activity.

Additional recent data (Rizzi, et al, *Life Sci.* 64, (1999), p. 157–163) has shown that the activation of nociceptin receptors in isolated guinea pig bronchus inhibits tachykinergic non adrenergic-non cholinergic contraction, indicating that nociceptin receptor agonists could be useful in the treatment of asthma. Also, it has been reported (Ciccocioppo et al, *Physchpharmacology.* 141 (1999), p. 220–224) nociceptin reduces the rewarding properties of ethanol in msP alcohol preferring rats, suggesting that intervention of nociceptin could be useful in the treatment of alcohol abuse. In EP 856,514, 8-substituted 1,3,8-triazaspiro[4,5]decan-4-on derivatives were disclosed as agonists and/or antagonists of orphanin OF (i.e., nociceptin) useful in the treatment of various disorders, including depression; 2-oxoimidazole derivatives disclosed in WO98/54168 were described as having similar utility. Earlier, benzimidazolyl piperidines were disclosed in U.S. Pat. No. 3,318,900 as having analgesic activity.

Potent analgesic agents such as traditional opioids, e.g. morphine, carry with them significant side-effects. Clinically relevant side-effects include tolerance, physical dependence, respiratory depression and a decrease in gastrointestinal motility. For many patients, particularly those subjected to chronic opioid therapy, i.e. cancer patients, these side effects limit the dose of opioid that can be administered. Clinical data suggests that more than one-third of cancer patients have pain which is poorly controlled by present agents. Data obtained with nociceptin suggest the potential for advantages over opioids. When administered chronically to rodents, nociceptin, in contrast to morphine, showed no addiction liability. Additionally, chronic morphine treatment did not lead to a "cross-tolerance" to nociceptin, suggesting that these agents act via distinct pathways.

In view of the current interest in pain relief, a welcome contribution to the art would be additional compounds useful for modifying the effect of nociceptin, a natural ligand to ORL-1 and therefore useful in the management of pain and anxiety. Such a contribution is provided by this invention.

SUMMARY OF THE INVENTION

Compounds of the present invention are represented by formula I

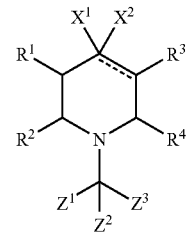

or a pharmaceutically acceptable salt or solvate thereof, wherein:

the dotted line represents an optional double bond;

$X^1$ is $R^5$—$(C_1$–$C_{12})$alkyl, $R^6$—$(C_3$–$C_{12})$cycloalkyl, $R^7$-aryl, $R^8$-heteroaryl or $R^{10}$—$(C_3$–$C_7)$heterocycloalkyl;

$X^2$ is —CHO, —CN, —NHC(=$NR^{26}$)$NHR^{26}$, —CH(=$NOR^{26}$), —NHOR$^{26}$, $R^7$-aryl, $R^7$-aryl($C_1$–$C_6$)alkyl, $R^7$-aryl($C_1$–$C_6$)alkenyl, $R^7$-aryl($C_1$–$C_6$)-alkynyl, —$(CH_2)_v$OR$^{13}_{21}$, —$(CH_2)_v$COOR$^{27}$, —$(CH_2)_v$CONR$^{14}$R$^{15}$, —$(CH_2)_v$NR$^{21}$R$^{22}$ or —$(CH_2)_v$NHC(O)R$^{21}$, wherein v is zero, 1, 2 or 3 and wherein q is 1 to 3 and a is 1 or 2;

or $X^1$ is

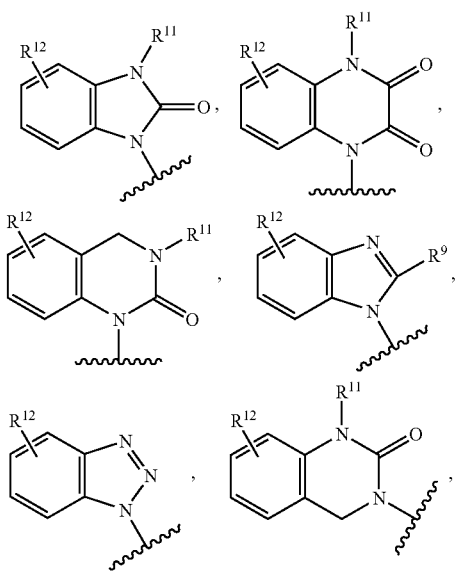

-continued

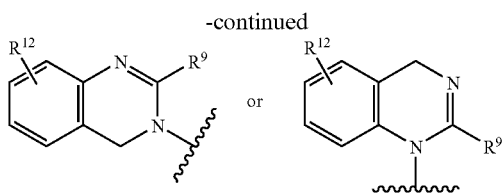

and $X^2$ is hydrogen;

or $X^1$ and $X^2$ together form a spiro group of the formula

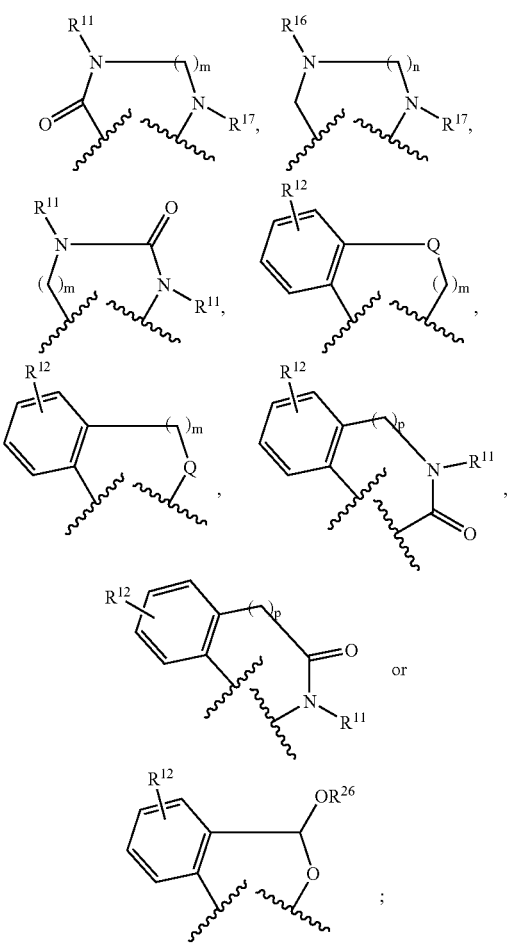

m is 1 or 2;

n is 1, 2 or 3, provided that when n is 1, one of $R^{16}$ and $R^{17}$ is —C(O)$R^{28}$;

p is 0 or 1;

Q is —CH$_2$—, —O—, —S—, —SO—, —SO$_2$— or —NR$^{17}$—;

$R^1$, $R^2$, $R^3$ and $R^4$ are independently selected from the group consisting of hydrogen and (C$_1$–C$_6$)alkyl, or ($R^1$ and $R^4$) or ($R^2$ and $R^3$) or ($R^1$ and $R^3$) or ($R^2$ and $R^4$) together can form an alkylene bridge of 1 to 3 carbon atoms;

$R^5$ is 1 to 3 substituents independently selected from the group consisting of H, $R^7$-aryl, $R^6$—(C$_3$–C$_{12}$)cycloalkyl, $R^8$-heteroaryl, $R^{10}$—(C$_3$–C$_7$)heterocycloalkyl, —NR$^{19}$R$^{20}$, —OR$^{13}$ and —S(O)$_{0-2}$R$^{13}$;

$R^6$ is 1 to 3 substituents independently selected from the group consisting of H, (C$_1$–C$_6$)alkyl, $R^7$-aryl, —NR$^{19}$R$^{20}$, —OR$^{13}$ and —SR$^{13}$;

$R^7$ is 1 to 3 substituents independently selected from the group consisting of hydrogen, halo, (C$_1$–C$_6$)alkyl, $R^{25}$-aryl, (C$_3$–C$_{12}$)cycloalkyl, —CN, —CF$_3$, —OR$^{19}$, —(C$_1$–C$_6$)alkyl-OR$^{19}$, —OCF$_3$, —NR$^{19}$R$^{20}$, —(C$_1$–C$_6$)alkyl-NR$^{19}$R$^{20}$, —NHSO$_2$R$^{19}$, —SO$_2$N(R$^{26}$)$_2$, —SO$_2$R$^{19}$, —SOR$^{19}$, —SR$^{19}$, —NO$_2$, —CONR$^{19}$R$^{20}$, —NR$^{20}$COR$^{19}$, —COR$^{19}$, —COCF$_3$, —OCOR$^{19}$, —OCO$_2$R$^{19}$, —COOR$^{19}$, —(C$_1$–C$_6$)alkyl-NHCOOC(CH$_3$)$_3$, —(C$_1$–C$_6$)alkyl-NH-COCF$_3$, —(C$_1$–C$_6$)alkyl-NHSO$_2$—(C$_1$–C$_6$)alkyl, —(C$_1$–C$_6$)alkyl-NHCONH—(C$_1$–C$_6$)-alkyl or

wherein f is 0 to 6; or $R^7$ substituents on adjacent ring carbon atoms may together form a methylenedioxy or ethylenedioxy ring;

$R^8$ is 1 to 3 substituents independently selected from the group consisting of hydrogen, halo, (C$_1$–C$_6$)alkyl, $R^{25}$-aryl, (C$_3$–C$_{12}$)cycloalkyl, —CN, —CF$_3$, —OR$^{19}$, —(C$_1$–C$_6$)alkyl-OR$^{19}$, —OCF$_3$, —NR$^{19}$R$^{20}$, —(C$_1$–C$_6$)alkyl-NR$^{19}$R$^{20}$, —NHSO$_2$R$^{19}$, —SO$_2$N(R$^{26}$)$_2$, —NO$_2$, —CONR$^{19}$R$^{20}$, —NR$^{20}$COR$^{19}$, —COR$^{19}$, —OCOR$^{19}$, —OCO$_2$R$^{19}$ and —COOR$^{19}$;

$R^9$ is hydrogen, (C$_1$–C$_6$)alkyl, halo, —OR$^{19}$, —NR$^{19}$R$^{20}$, —NHCN, —SR$^{19}$ or —(C$_1$–C$_6$)alkyl-NR$^{19}$R$^{20}$;

$R^{10}$ is H, (C$_1$–C$_6$)alkyl, —OR$^{19}$, —(C$_1$–C$_6$)alkyl-OR$^{19}$, —NR$^{19}$R$^{20}$ or —(C$_1$–C$_6$)alkyl-NR$^{19}$R$^{20}$;

$R^{11}$ is independently selected from the group consisting of H, $R^5$—(C$_1$–C$_6$)alkyl, $R^6$—(C$_3$–C$_{12}$)cycloalkyl, —(C$_1$–C$_6$)alkyl(C$_3$–C$_{12}$)cycloalkyl, —(C$_1$–C$_6$)alkyl-OR$^{19}$, —(C$^1$–C$_6$)alkyl-NR$^{19}$R$^{20}$ and $$—(CH_2)_q—N\underset{}{\overset{}{\diagdown}}\phantom{)_a}$$

wherein q and a are as defined above;

$R^{12}$ is H, (C$_1$–C$_6$)alkyl, halo, —NO$_2$, —CF$_3$, —OCF$_3$, —OR$^{19}$, —(C$_1$–C$_6$)alkyl-OR$^{19}$, —NR$^{19}$R$^{20}$ or —(C$_1$–C$_6$)alkyl-NR$^{19}$R$^{20}$;

$R^{13}$ is H, (C$_1$–C$_6$)alkyl, $R^7$-aryl, —(C$_1$–C$_6$)alkyl-OR$^{19}$, —(C$_1$–C$_6$)alkyl-NR$^{19}$R$^{20}$; —(C$_1$–C$_6$)alkyl-SR$^{19}$; or aryl (C$_1$–C$_6$) alkyl;

$R^{14}$ and $R^{15}$ are independently selected from the group consisting of H, $R^5$—(C$_1$–C$_6$)alkyl, $R^7$-aryl and $$—(CH_2)_q—\underset{\underset{O}{\|}}{C}—N\phantom{)_a}$$

wherein q and a are as defined above;

$R^{16}$ and $R^{17}$ are independently selected from the group consisting of hydrogen, $R^5$—(C$_1$–C$_6$)alkyl, $R^7$-aryl, (C$_3$–C$_{12}$)cycloalkyl, $R^8$-heteroaryl, $R^8$-heteroaryl(C$_1$–C$_6$)

alkyl, —C(O)R$^{28}$, —(C$_1$–C$_6$)alkyl(C$_3$–C$_7$)-heterocycloalkyl, —(C$_1$–C$_6$)alkyl-OR$^{19}$ and —(C$_1$–C$_6$)alkyl-SR$^{19}$;

R$^{19}$ and R$^{20}$ are independently selected from the group consisting of hydrogen, (C$_1$–C$_6$)alkyl, (C$_3$–C$_{12}$)cycloalkyl, aryl and aryl(C$_1$–C$_6$)alkyl;

R$^{21}$ and R$^{22}$ are independently selected from the group consisting of hydrogen, (C$_1$–C$_6$)alkyl, (C$_3$–C$_{12}$)cycloalkyl, (C$_3$–C$_{12}$)cycloalkyl(C$_1$–C$_6$)alkyl, (C$_3$–C$_7$)heterocycloalkyl, —(C$_1$–C$_6$)alkyl(C$_3$–C$_7$)-heterocycloalkyl, R$^7$-aryl, R$^7$-aryl (C$_1$–C$_6$)alkyl, R$^8$-heteroaryl(C$_1$–C$_{12}$)alkyl, —(C$_1$–C$_6$)alkyl-OR$^{19}$, —(C$_1$–C$_6$)alkyl-NR$^{19}$R$^{20}$, —(C$_1$–C$_6$)alkyl-SR$^{19}$, —(C$_1$–C$_6$)alkyl-NR$^{18}$—(C$_1$–C$_6$)alkyl-O—(C$_1$–C$_6$)alkyl and —(C$_1$–C$_6$)alkyl-NR$^{18}$—(C$_1$–C$_6$)alkyl-NR$^{18}$—(C$_1$–C$_6$)alkyl;

R$^{18}$ is hydrogen or (C$_1$–C$_6$)alkyl;

Z$^1$ is R$^5$—(C$_1$–C$_{12}$)alkyl, R$^7$-aryl, R$^8$-heteroaryl, R$^6$—(C$_3$–C$_{12}$)cycloalkyl, R$^{10}$—(C$_3$–C$_7$)heterocycloalkyl, —CO$_2$(C$_1$–C$_6$)alkyl, CN or —C(O)NR$^{19}$R$^{20}$; Z$^2$ is hydrogen or Z$^1$; Z3 is hydrogen or (C$_1$–C$_6$)alkyl; or Z$^1$, Z$^2$ and Z$^3$, together with the carbon to which they are attached, form the group

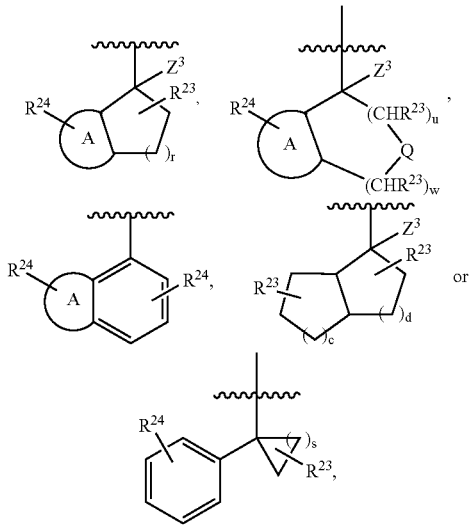

wherein r is 0 to 3; w and u are each 0–3, provided that the sum of w and u is 1–3; c and d are independently 1 or 2; s is 1 to 5; and ring A is a fused R$^7$-phenyl or R$^8$-heteroaryl ring;

R$^{23}$ is 1 to 3 substituents independently selected from the group consisting of H, (C$_1$–C$_6$)alkyl, —OR$^{19}$, —(C$_1$–C$_6$)alkyl-OR$^{19}$, —NR$^{19}$R$^{20}$ and —(C$_1$–C$_6$)alkyl-NR$^{19}$R$^{20}$;

R$^{24}$ is 1 to 3 substituents independently selected from the group consisting of R$^{23}$, —CF$_3$, —OCF$_3$, NO$_2$ or halo, or R$^{24}$ substituents on adjacent ring carbon atoms may together form a methylenedioxy or ethylenedioxy ring;

R$^{25}$ is 1–3 substituents independently selected from the group consisting of H, (C$_1$–C$_6$)alkyl, (C$_1$–C$_6$)alkoxy and halo;

R$^{26}$ is independently selected from the group consisting of H, (C$_1$–C$_6$)alkyl and R$^{25}$—C$_6$H$_4$—CH$_2$—;

R$^{27}$ is H, (C$_1$–C$_6$)alkyl, R$^7$-aryl(C$_1$–C$_6$)alkyl, or (C$_3$–C$_{12}$) cycloalkyl;

R$^{28}$ is (C$_1$–C$_6$)alkyl, —(C$_1$–C$_6$)alkyl(C$_3$–C$_{12}$)cycloalkyl, R$^7$-aryl, R$^7$-aryl-(C$_1$–C$_6$)alkyl, R$^8$-heteroaryl, —(C$_1$–C$_6$) alkyl-NR$^{19}$R$^{20}$, —(C$_1$–C$_6$)alkyl-OR$^{19}$ or —(C$_1$–C$_6$)alkyl-SR$^{19}$;

provided that when X$^1$ is

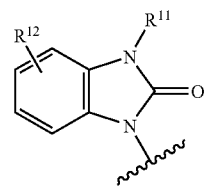

or X$^1$ and X$^2$ together are

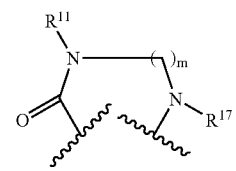

and Z$^1$ is R$^7$-phenyl, Z$^2$ is not hydrogen or (C$_1$–C$_3$)alkyl;

provided that when Z$^1$, Z$^2$ and Z$^3$, together with the carbon to which they are attached, form

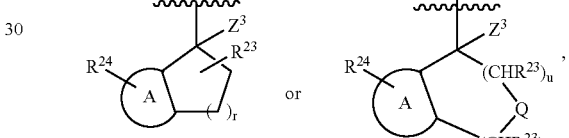

and X$^1$ and X$^2$ together are R$^{11}$ is not H, (C$_1$–C$_6$)alkyl, (C$_1$–C$_6$)alkoxy(C$_1$–C$_6$)alkyl or (C$_1$–C$_6$)hydroxyalkyl;

provided that when R$^2$ and R$^4$ form an alkylene bridge, Z$^1$, Z$^2$ and Z$^3$, together with the carbon to which they are attached, are not provided that when X$^1$ is

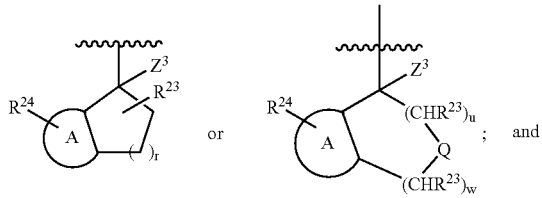

and Z$^1$ is R$^6$—(C$_3$–C$_{12}$)-cycloalkyl, Z$^2$ is not H.

Preferred compounds of the invention are those wherein Z$^1$ and Z$^2$ are each R$^7$-aryl, particularly R$^7$-phenyl. Preferred R$^7$ substituents are (C$_1$–C$_6$)alkyl and halo, with ortho-substitution being more preferred.

Compounds wherein R$^1$, R$^2$, R$^3$ and R$^4$ are each hydrogen are preferred, as well as compounds wherein R$^1$ and R$^3$ are each hydrogen and R$^2$ and R$^4$ are an alkylene bridge of 2 or 3 carbons.

Preferred are compounds wherein X$^1$ is R$^7$-aryl, for example R$^7$-phenyl, and X$^2$ is OH (i.e., X$^2$ is —(CH$_2$)$_v$OR$^{13}$, wherein v is 0 and R$^{13}$ is H) or —NC(O)R$^{28}$, compounds wherein X$^1$ is

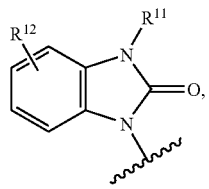

wherein $R^{12}$ is hydrogen and $R^{11}$ is $(C_1-C_6)$alkyl, $-(C_1-C_6)$alkyl$(C_3-C_{12})$cycloalkyl, $-(C_1-C_6)$alkyl-$OR^{19}$ or $-(C_1-C_6)$alkyl-$NR^{19}R^{20}$; and compounds wherein $X^1$ and $X^2$ together form the spirocyclic group

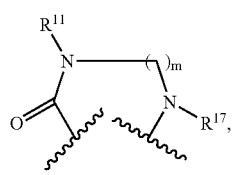

wherein m is 1, $R^{17}$ is phenyl and $R^{11}$ is $-(C^1-C_6)$alkyl-$OR^{19}$ or $-(C_1-C_6)$alkyl-$NR^{19}R^2$, or

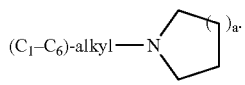

In another aspect, the invention relates to a pharmaceutical composition comprising a compound of formula I and a pharmaceutically acceptable carrier.

The compounds of the present invention are agonists and/or antagonists of the ORL-1 receptor, and therefore, in another aspect, the invention relates to a method of treating pain, anxiety, cough, asthma, alcohol abuse or depression, comprising administering to a mammal in need of such treatment an effective amount of a compound of formula I.

In another aspect, the invention relates to a method of treating cough, comprising administering to a mammal in need of such treatment: (a) an effective amount of a nociceptin receptor ORL-1 agonist; and (b) an effective amount of a second agent for treating cough, allergy or asthma symptoms selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In still another aspect, the invention relates to a pharmaceutical composition comprising a nociceptin receptor ORL-1 agonist and a second agent selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In yet another aspect, the present invention relates to a novel compound not included in the structure of formula I, said compound being:

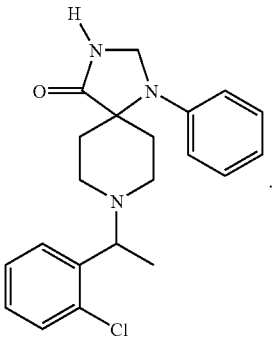

DETAILED DESCRIPTION OF THE INVENTION

Figure 1:
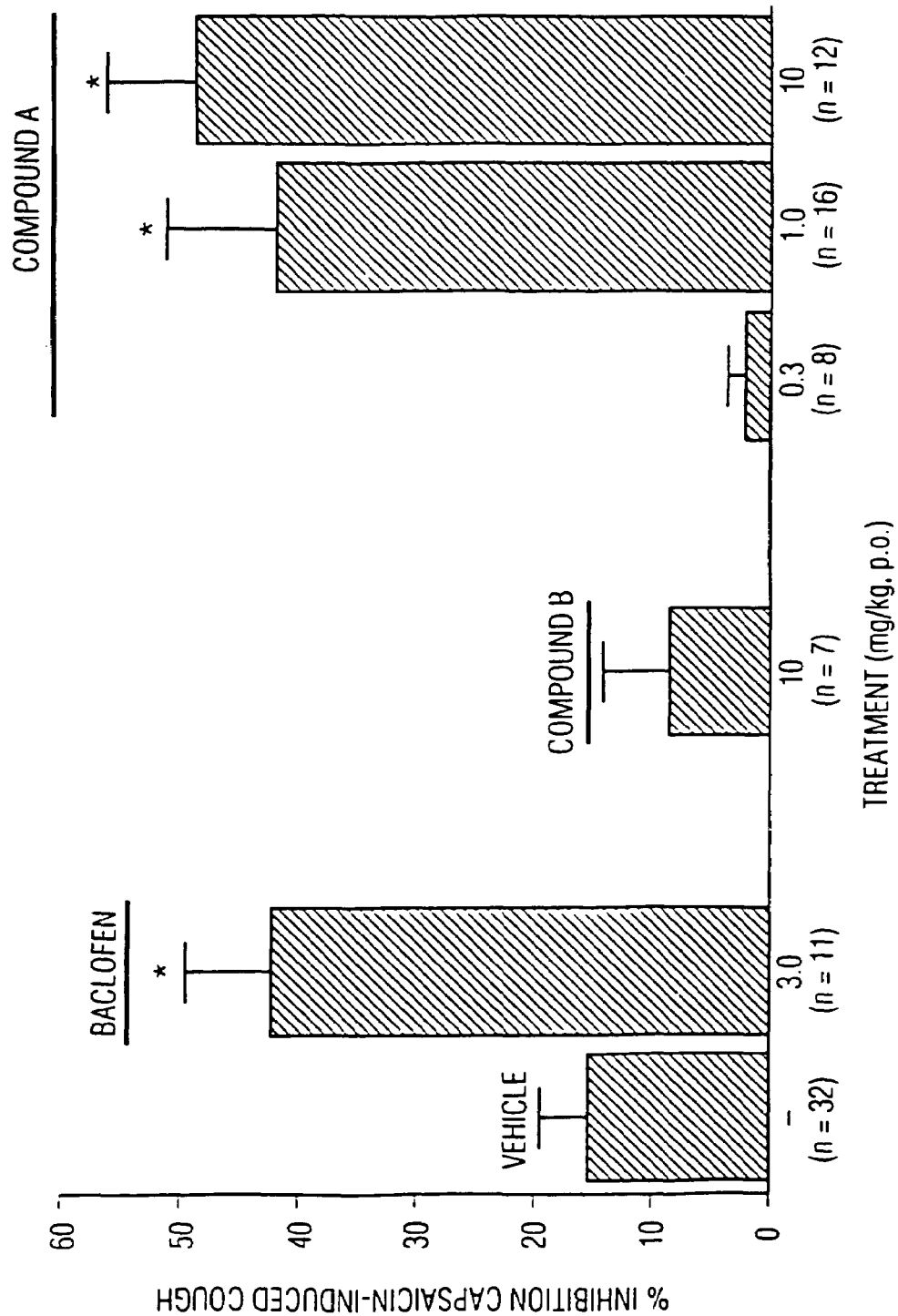
FIG. 1 illustrates the effect in guinea pigs of Compounds A and B (see Example 12) compared to baclofen on capsaicin-induced cough.

As used herein, the following terms are used as defined below unless otherwise indicated:

M+ represents the molecular ion of the molecule in the mass spectrum and MH+ represents the molecular ion plus hydrogen of the molecule in the mass spectrum;

Bu is butyl; Et is ethyl; Me is methyl; and Ph is phenyl;

alkyl (including the alkyl portions of alkoxy, alkylamino and dialkylamino) represents straight and branched carbon chains containing from 1 to 12 carbon atoms or 1 to 6 carbon atoms; for example methyl, ethyl, propyl, iso-propyl, n-butyl, t-butyl, n-pentyl, isopentyl, hexyl and the like;

alkenyl represents an alkyl chain of 2 to 6 carbon atoms comprising one or two double bonds in the chain, e.g., vinyl, propenyl or butenyl;

alkynyl represents an alkyl chain of 2 to 6 carbon atoms comprising one triple bond in the chain, e.g., ethynyl or propynyl;

alkoxy represents an alkyl moiety covalently bonded to an adjacent structural element through an oxygen atom, for example, methoxy, ethoxy, propoxy, butoxy, pentoxy, hexoxy and the like;

aryl (including the aryl portion of arylalkyl) represents a carbocyclic group containing from 6 to 15 carbon atoms and having at least one aromatic ring (e.g., aryl is phenyl), wherein said aryl group optionally can be fused with aryl, $(C_3-C_7)$cycloalkyl, heteroaryl or hetero$(C_3-C_7)$cycloalkyl rings; and wherein $R^7$-aryl means that any of the available substitutable carbon and nitrogen atoms in said aryl group and/or said fused ring(s) is optionally and independently substituted, and wherein the aryl ring is substituted with 1–3 $R^7$ groups. Examples of aryl groups are phenyl, naphthyl and anthill;

arylalkyl represents an alkyl group, as defined above, wherein one or more hydrogen atoms of the alkyl moiety have been substituted with one to three aryl groups; wherein aryl is as defined above;

aryloxy represents an aryl group, as defined above, wherein said aryl group is covalently bonded to an adjacent structural element through an oxygen atom, for example, phenoxy;

cycloalkyl represents saturated carbocyclic rings of from 3 to 12 carbon atoms, preferably 3 to 7 carbon atoms; wherein $R^6$-cycloalkyl means that any of the available substitutable carbon atoms in said cycloalkyl group is optionally and independently substituted, and wherein the cycloalkyl ring is substituted with 1–3 $R^6$ groups;

cycloalkylalkyl represents an alkyl group, as defined above, wherein one or more hydrogen atoms of the alkyl moiety have been substituted with one to three cycloalkyl groups, wherein cycloalkyl is as defined above;

halo represents fluoro, chloro, bromo and iodo;

heteroaryl represents cyclic groups having one to three heteroatoms selected from O, S and N, said heteroatom(s) interrupting a carbocyclic ring structure and having a sufficient number of delocalized pi electrons to provide aromatic character, with the aromatic heterocyclic groups containing from 5 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted, and wherein the heteroaryl ring can be substituted with 1–3 $R^8$ groups; representative heteroaryl groups can include, for example, furanyl, thienyl, imidazoyl, pyrimidinyl, triazolyl, 2-, 3- or 4-pyridyl or 2-, 3- or 4-pyridyl N-oxide wherein pyridyl N-oxide can be represented as:

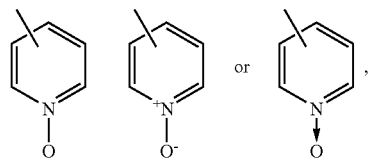

heteroarylalkyl represents an alkyl group, as defined above, wherein one or more hydrogen atoms have been replaced by one or more heteroaryl groups, as defined above;

heterocycloalkyl represents a saturated ring containing from 3 to 7 carbon atoms, preferably from 4 to 6 carbon atoms, interrupted by 1 to 3 heteroatoms selected from —O—, —S— and —$NR^{21}$—, wherein $R^{21}$ is as defined above, and wherein optionally, said ring may contain one or two unsaturated bonds which do not impart aromatic character to the ring; and wherein any of the available substitutable carbon atoms in the ring may substituted, and wherein the heterocycloalkyl ring can be substituted with 1–3 $R^{10}$ groups; representative heterocycloalkyl groups include 2- or 3-tetrahydrofuranyl, 2- or 3- tetrahydrothienyl, 1-, 2-, 3- or 4-piperidinyl, 2- or 3-pyrrolidinyl, 1-, 2- or 3-piperazinyl, 2- or 4-dioxanyl, morpholinyl,

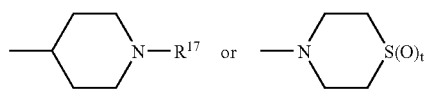

wherein $R^{17}$ is as defined above and t is 0, 1 or 2.

When the optional double bond in the piperidinyl ring of formula I is present, one of $X^1$ and $X^2$ forms the bond with the 3-position carbon and the remaining $X^1$ or $X^2$ is not hydrogen.

When $X^1$ and $X2$ form a spiro group as defined above, the wavy lines in the structures shown in the definition indicate the points of attachment to to the 4-position carbon of the piperidinyl ring, e.g., compounds of the following formulas are formed:

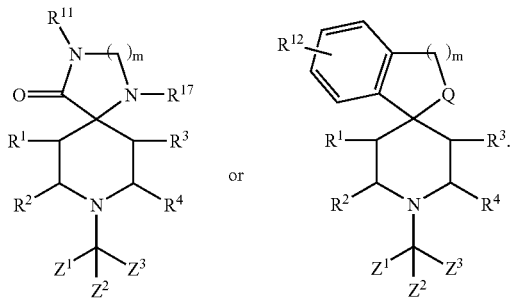

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpoposes of the invention.

Compounds of the invention can be prepared by known methods from starting materials either known in the art or prepared by methods known in the art. Examples of general procedures and specific preparative examples are given below.

Typically, $X^1,X^2$-substituted piperidines are alkylated with $Z^1,Z^2,Z^3$-substituted halomethanes in the presence of excess bases such as $K_2CO_3$ and $Et_3N$, in solvents such as DMF, THF or $CH_3CN$, at room temperature or at elevated temperatures.

$X^1,X^2$-substituted piperidines are either commercially available or made by known procedures. For example, 4-hydroxy-4-phenyl-piperidine can be converted to a 4-tBoc-amino-4-phenylpiperidine according to the following reaction scheme, wherein Bn is benzyl, Ph is phenyl and tBoc is t-butoxycarbonyl:

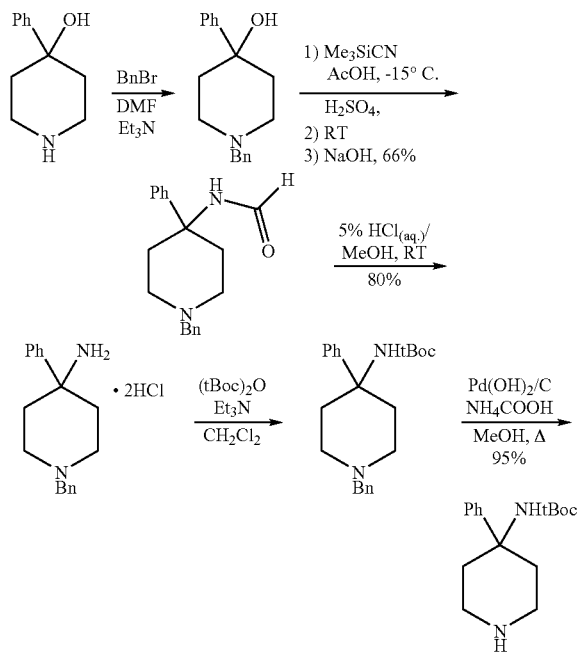

Commercially available 4-phenyl-4-piperidinol is protected with a benzyl group and the resulting intermediate is then treated with $Me_3SiCN$. The resultant amide is hydrolyzed with aqueous HCl in $CH_3OH$ to produce the 4-amino compound. The amino group is protected with tBoc and the N-benzyl group is removed by hydrogenolysis to produce the desired 4-amino-piperidine derivative.

The 4-(protected)amino-piperidine then can be reacted with a $Z^1,Z^2,Z^3$-halomethane and the protecting group removed. The amine (i.e., $X^2$ is $-NH_2$) can undergo various standard conversions to obtain amine derivatives. For example, the amine of formula I can be reacted with a $R^{22}$-carboxaldehyde in the presence of a mild reducing agent such as $Na(OAc)_3BH$ or with a compound of the formula $R^{22}$-L, wherein L is a leaving group such as Cl or Br, in the presence of a base such as $Et_3N$.

An alternative method for preparing compounds of formula I wherein $X^1$ is $R^7$-aryl and $X^2$ is OH involves alkylating a 4-piperidone hydrochloride with a $Z^1,Z^2,Z^3$-halomethane, then reacting the ketone with an appropriately substituted $R^7$-phenylmagnesium bromide or with a compound of the formula $X^1$-$L^1$, wherein $L^1$ is Br or I, and n-butyl-lithium.

$X^1,X^2$-substituted compounds of formula I can be converted into other compounds of formula I by performing reactions well known in the art on the $X^1$ and/or $X^2$ substituents. For example, a carboxaldehyde-substituted piperidine (i.e., $X^2$ is $-CHO$) can be converted to a substituted piperidine wherein $X^2$ is $R^{13}$—O—$CH_2$—, as shown in the following procedure for a compound of formula I wherein $X^1$ is phenyl, $Z^1$ and $Z^2$ are each phenyl, and $R^1$, $R^2$, $R^3$ and $R^4$, and $Z^3$ are H:

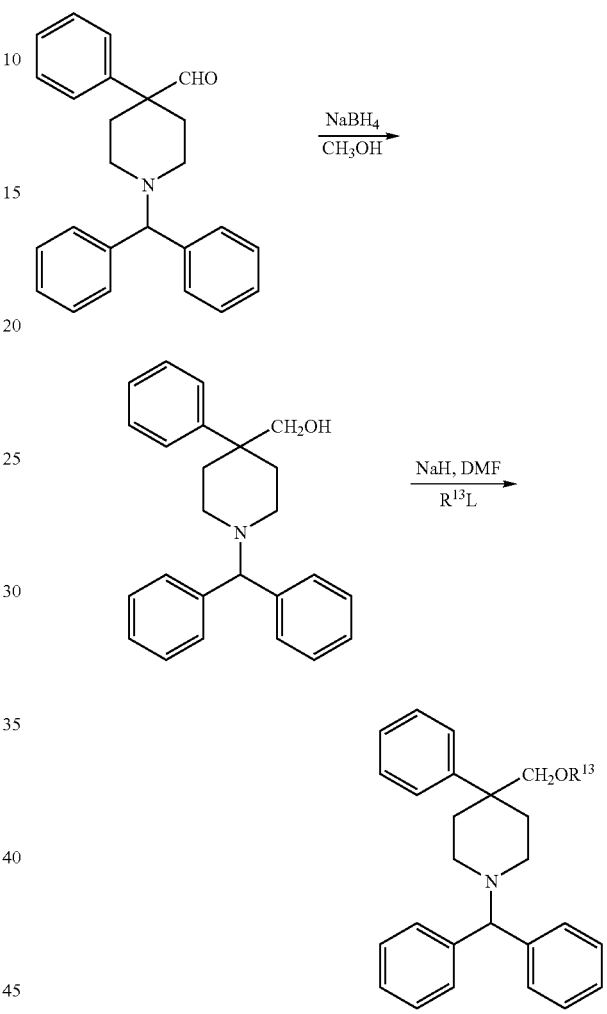

A cyano-substituted piperidine (i.e., $X^2$ is $-CN$) can be converted to a substituted piperidine wherein $X^2$ is $R^{21}R^{22}N$—$CH_2$— or $X^2$ is $R^{28}C(O)NH$—$CH_2$—, as shown in the following procedure for a compound of formula I wherein $X^1$ is phenyl, $R^{21}$, $R^1$, $R^2$, $R^3$ and $R^4$, and $Z^3$ are H, and L is a leaving group such as Cl or Br:

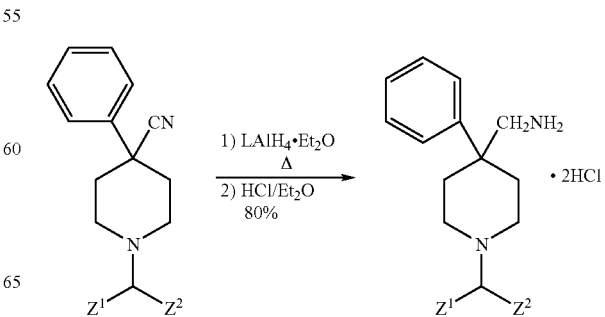

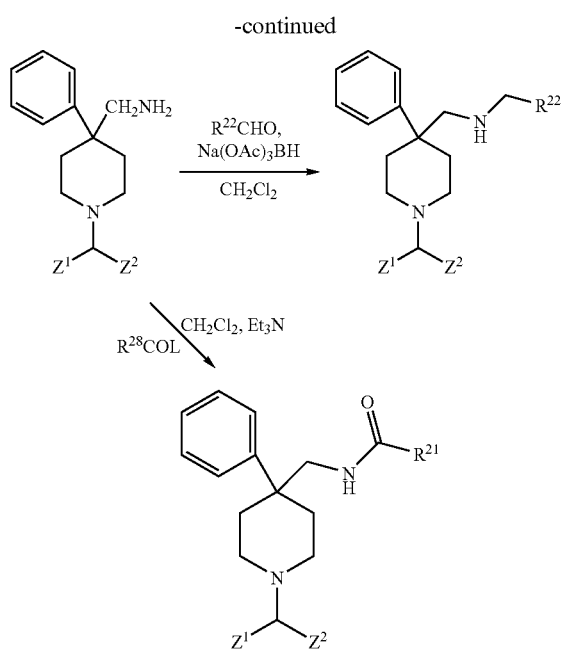

Compounds of formula I wherein $X^1$ is a benzofused nitrogen-containing heterocycle having an $R^{11}$ substituent other than hydrogen are prepared by reacting the corresponding compounds wherein $R^{11}$ is hydrogen with a compound of the formula $R^{11}$ L ($R^{11}$ is not H, and L is as defined above).

Alternatively, $X^1,X^2$-substituted piperidine starting materials can be converted into other $X^1,X^2$-substituted piperidines by similar procedures before reacting with the $Z^1,Z^2,Z^3$-substituted halomethane.

For compounds of formula I wherein $R^1$, $R^2$, $R^3$ and $R^4$ variously form alkylene bridges, commercially available N-protected 4-piperidones are treated with phenyl lithium and resulting intermediate is deprotected to produce the desired compounds, for example:

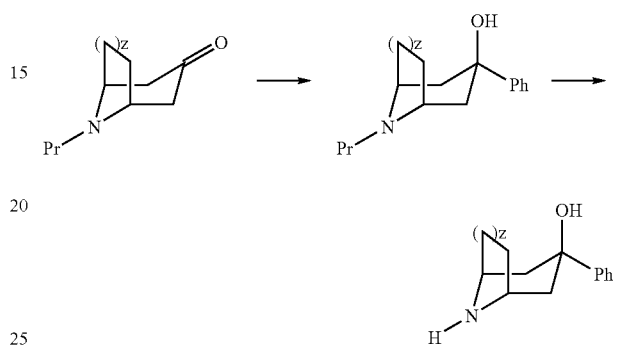

wherein Pr is a N-protecting group, Ph is phenyl and z is 1–2.

The $Z^1,Z^2,Z^3$-halomethyl derivatives wherein $Z^1$ and $Z^2$ are $R^7$-phenyl are either commercially available or can be prepared using the procedure shown in the following reaction scheme:

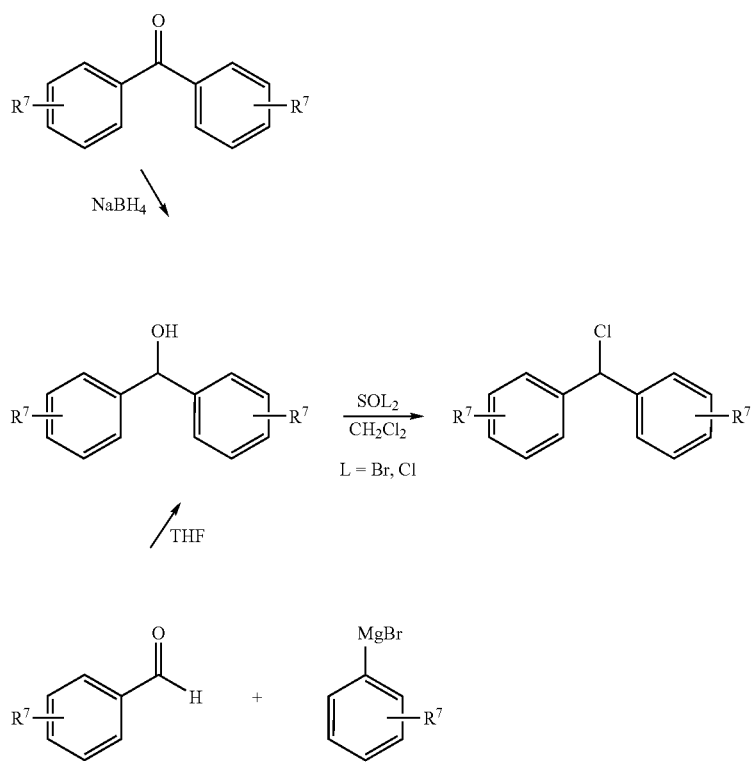

Similar procedures, or others known in the art, can be used to prepare compounds wherein the Z substituents are other than phenyl.

Compounds of the present invention and preparative starting materials thereof, are exemplified by the following examples, which should not be construed as limiting the scope of the disclosure.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); and diethyl ether (Et$_2$O). Room temperature is abbreviated as rt.

EXAMPLE 1

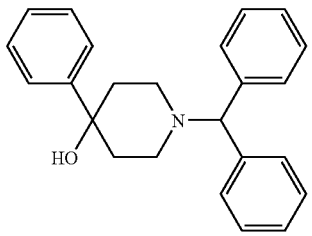

A mixture of 4-hydroxy-4-phenyl piperidine (1.5 g, 8.47 mmol) and K$_2$CO$_3$ (3.0 g, 21.73 mmol) in CH$_3$CN was stirred at rt. To this was added α-bromo-diphenylmethane (2.5 g, 10.12 mmol) and the reaction was stirred overnight. The reaction mixture was concentrated, redissolved in CH$_2$Cl$_2$, washed with water, dried (MgSO$_4$) and concentrated. Chromatography (SiO$_2$, 9:1 hexane/EtOAc) gave the title compound (2.6 g, 90%). $^1$H NMR (CDCl$_3$): δ 1.80 (m, 2H), 2.25 (m, 2H), 2.42 (m, 2H), 2.90 (m, 2H), 4.40 (s, 1H), 7.2–7.6 (m, 15H).

EXAMPLE 2

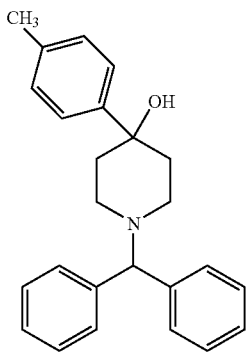

Step 1: A solution of 4-piperidone monohydrate hydrochloride (5 g, 32.6 mmol) in CH$_3$CN was alkylated using the procedure described in Example 1. Chromatography of the residue on silica (95:5 hexane/EtOAc) gave the desired compound.

Step 2: 4-Methylphenylmagnesium bromide (0.5 M in THF, 1.75 ml, 0.87 mmol) was added to a solution of product of Step 1 (191 mg, 0.72 mmol) in THF dropwise at 0° C. The solution was stirred at 0° for 2 h, quenched with ice-H$_2$O, extracted with EtOAc, washed with H$_2$O and brine, dried, and concentrated. Chromatography of the residue on silica (95:5 hexane/EtOAc, 93:7 hexane/EtOAc) gave the title compound (0.091 g, 30%). $^1$H NMR (CDCl$_3$) δ 7.5 (m, 6H, ArH), 7.3 (t, 4H, ArH), 7.2 (t, 4H, ArH), 4.35 (s, 1H), 2.8 (d, 2H), 2.4 (m, 5H), 2.2 (td, 2H), 1.75 (d, 2H); MS (Cl) 358 (M+1); Elemental analysis for C$_{25}$H$_{27}$NO.1.2 H$_2$O: calcd: C, 79.2; H, 7.82; N, 3.69; observed: C, 78.90; H, 8.02; N, 3.85.

EXAMPLE 3

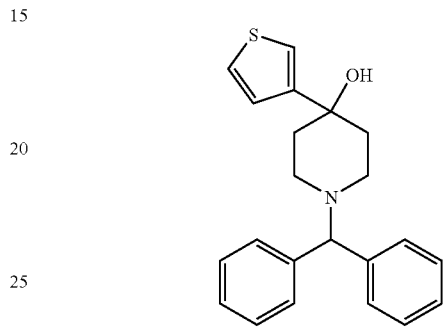

Add n-BuLi (2.5 M, 0.38 ml. 0.95 mmol) to a solution of 3-bromo-thiophene (0.15 g, 0.95 mmol) in Et$_2$O dropwise at −70° C. and stir for 2 h. Add a solution of the product of Step 1 of Example 2 (230 mg, 0.87 mmol) in Et$_2$O (4 ml) to the reaction mixture, slowly warm to rt over a period of 3 h, quench with ice-cooled NH$_4$Cl (aq), extract with Et$_2$O, wash with H$_2$O and brine, dry, and concentrate. Chromatograph the residue (95:5 hexane/EtOAc) to give the title compound (90 mg). $^1$H NMR (CDCl$_3$) δ 7.5 (d, 2H), 7.35 (bt, 4H), 7.25 (m, 3H), 7.2 (m, 2H), 4.4 (s, 1H), 2.8 (d, 2H), 2.5 (t, 2H), 2.3 (dt, 2H), 2.0 (d, 2H); MS (Cl) 350 (M+1); Elemental analysis for C$_{22}$H$_{22}$NOS.1.1 HCl.0.9 H$_2$O: calcd: C, 65.11; H, 6.43; N, 3.54; S, 7.8; Cl, 9.61; observed: C, 65.27; H, 6.54; N, 3.45; S, 7.30; Cl, 9.43.

EXAMPLE 4

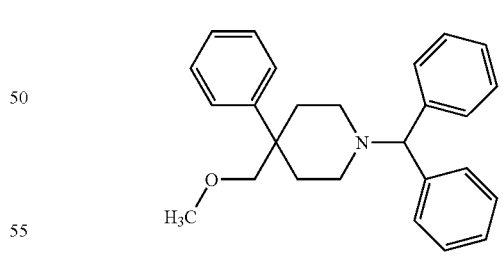

Step 1: 4-Phenyl-4-piperidinecarboxaldehyde (1.0 g, 5.29 mM) was alkylated using the procedure of Example 1, Step 1, to obtain the desired product (1.69 g, 90%). $^1$H NMR (CDCl$_3$): δ 2.40 (m, 4H), 2.50 (m, 2H), 2.85 (m, 2H), 4.25 (s, 1H), 7.20–7.50 (m, 15H), 9.42 (s, 1H).

Step 2: A solution of the product from Step 1 (3.0 g, 8.45 mmol) was cooled to 0° C. and treated with NaBH$_4$ (1.0 g, 26.32 mmol). After 0.5 h, reaction mixture was treated with 1N HCl and concentrated. The residue was extracted with CH$_2$Cl$_2$, dried (MgSO$_4$) and evaporated. Column chromatography on the residue (4:1 hexane:EtOAc) produced desired primary alcohol. $^1$H NMR (CDCl$_3$): δ 2.00 (m, 2H), 2.25 (m, 4H), 2.65 (m, 2H), 3.65 (d, 2H), 4.20 (s, 1H), 4.25 (d, 1H), 7.2–7.6 (m, 15H).

Step 3: The product of Step 2 was treated with NaH in DMF at 0° C. for 0.5 h. CH$_3$I was added and reaction was warmed up to rt. After stirring overnight, the reaction mixture was poured on ice, extracted with Et$_2$O, dried (MgSO$_4$) and evaporated. Column chromatography on the residue produced the title compound. $^1$H NMR (CDCl$_3$): δ 2.10 (m, 4H), 2.40 (m, 2H), 2.78 (m, 2H), 2.90 (m, 2H), 3.00 (s, 3H), 4.38 (s, 1H), 7.21–7.52 (m, 15H).

EXAMPLE 5

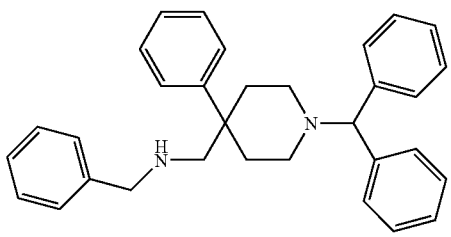

Step 1: A solution of 4-Cyano-4-phenylpiperidine hydrochloride (5.0 g, 22.4 mM) in DMF (30 ml) was treated with Et$_3$N (7.20 ml, 47 mM) and bromodiphenylmethane (6.38 g, 25.80 mM) and stirred at rt under N$_2$ for 20 h. The reaction mixture was concentrated in vacuo and partitioned between EtOAc and H$_2$O. The organic layer was washed with twice with water, then brine, and dried (MgSO$_4$), filtered and concentrated. Chromatography (SiO$_2$, 19:1 hexane/EtOAc) gave 6.0 g (76%) of the desired product. $^1$H NMR (CDCl$_3$): δ 2.21 (m, 4H), 2.49 (t, J=12.3 Hz, 2H), 3.11 (d, J=12.5 Hz, 2H), 4.46 (s, 1H), 7.45 (m, 15H).

Step 2: A solution of the product (6.0 g, 17 mM) of Step 1 in Et$_2$O (40 ml) was cooled to 0° C. and treated with a 1 M solution of of LAH (34.10 ml, 34 mM), dropwise, under N$_2$, over 0.5 h. The reaction mixture was allowed to warm to rt and then refluxed for 4 h. The reaction mixture was cooled to 0° C. and treated with water (8 eq.). The reaction mixture was allowed to warm to rt and was stirred for 1 h. The resultant solid was filtered off and rinsed with Et$_2$O, and the filtrate was concentrated to yield 5.45 g (90%) of desired product. $^1$H NMR (CD$_3$OD): δ 1.84 (m, 2H), 2.16 (m, 4H), 2.56 (m, 2H), 2.68 (m, 2H), 4.07 (s, 1H), 7.25 (m, 15H).

Step 3: A solution of the product (0.2 g, 0.56 mM) of Step 2 in CH$_2$Cl$_2$ (3 ml) was treated with benzoyl chloride (0.078 ml, 0.673 mM) and pyridine (0.045 g, 0.568 mM) at rt for 18 h under N$_2$. The reaction mixture was concentrated, then partitioned between H$_2$O and CH$_2$Cl$_2$. The organic layer was washed with water (2×) and brine, then dried (MgSO$_4$), filtered and concentrated. Chromatography (SiO$_2$, 3:1 hexane/EtOAc) gave 0.2 g (77%) of the desired product. $^1$H NMR (CD$_3$OD): δ 2.13 (m, 6H), 2.66 (m, 4H), 3.50 (s, 2H), 4.07 (s, 1H), 7.11–7.65 (m, 20H).

Step 4: A solution of the product (0.075 g, 0.16 mM) of Step 3 in THF (3 ml) was cooled to 0° C. with stirring. LAH (solid, 0.025 g, 0.65 mM) was added under N$_2$ and stirring was continued for 0.25 h. The reaction mixture was then refluxed for 5 h, then stirred at rt for 18 h. The reaction mixture was cooled to 0° C. and quenched with water (8 eq). The reaction mixture was allowed to warm to rt and was stirred for 1 h. The resultant solid was filtered off and rinsed with Et$_2$O, the filtrate was dried (MgSO$_4$) and concentrated. Chromatography (neutral Al$_2$O$_3$, CH$_2$Cl$_2$, then 3:1 CH$_2$Cl$_2$: EtOAc) gave 0.014 g (20%) of the title compound. $^1$H NMR (CD$_3$OD): δ 1.90 (m, 2H), 2.15 (m, 4H), 2.48 (m, 2H), 2.68 (s, 2H), 3.53 (s, 2H), 4.05 (s, 1H), 7.01–7.38 (m, 20H).

EXAMPLE 6

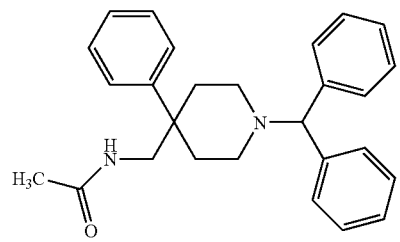

The product of Example 5, Step 2 (0.2 g, 0.561 mM), acetic anhydride (3 ml) and Et$_3$N (0.096 ml, 0.67 mM) were combined and stirred at rt for 18 h. The reaction mixture was concentrated and partitioned between H$_2$O and CH$_2$Cl$_2$. The organic layer was washed with water (2×), brine, then dried (MgSO$_4$), filtered and concentrated to give 0.214 g (95%) of the title compound. $^1$H NMR (CD$_3$OD): δ 1.87 (m, 5H), 2.16 (m, 4H), 2.61 (m, 2H), 3.31 (s, 2H), 4.07 (s, 1H), 7.12–7.40 (m, 20H).

EXAMPLE 7

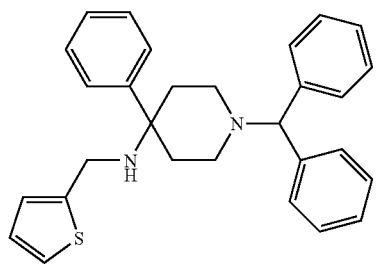

Step 1: A solution of 4-phenyl-4-hydroxy piperidine (10.0 g, 56.4 mM) in DMF (60 ml) was treated with Et$_3$N (8.28 ml, 59.2 mM) and benzyl bromide (7.37 ml, 62.10 mM) and stirred at rt under N$_2$ for 20 h. The reaction mixture was concentrated in vacuo, basified to pH 8 with saturated NaHCO$_3$ and partitioned between EtOAc and H$_2$O. The organic layer was washed twice with water, then brine, and dried (MgSO$_4$), filtered and concentrated. Chromatography (neutral Al$_2$O$_3$, hexane, then 1:1 hexane:EtOAc) gave 11.95 g (80%) of the desired product.

Step 2: To a mixture of the product (30.0 g, 0.112 mol) of Step 1 and (CH$_3$)$_3$SiCN (59.94 ml, 0.448 mol), cooled to −15° C. in an ethylene glycol/CO$_2$ bath, under N$_2$, is added glacial AcOH (47 ml) dropwise, while maintaining an internal temperature of −15° C. Concentrated H$_2$SO$_4$ (47 ml, 0.34 M) is added dropwise, with vigorous stirring, while maintaining an internal temperature of −15° C. The cooling bath was then removed and reaction mixture was stirred at rt for 18 h. The reaction mixture was poured on ice and adjusted to pH 7 with a 50% NaOH solution while maintaining a temperature of 25° C. The reaction mixture was then extracted with $CH_2Cl_2$, and the organic layer was washed with water (2×), then brine, and dried ($MgSO_4$), filtered and concentrated. Recrystalization with EtOAc/hexane (1:10) gave 22.35 g (68%) of desired compound. $^1H$ NMR ($CD_3OD$): δ 2.10 (m, 2H), 2.40 (m, 4H), 2.82 (d, J=11.50 Hz, 2H), 3.57 (s, 2H), 7.20–7.43 (m, 10H), 8.05 (s, 1H).

Step 3: The product of Step 2 (20 g, 67.9 mM) and 5% (w/w) concentrated HCl (aq)/$CH_3OH$ (350 ml) were stirred under $N_2$ for 48 h. The mixture was concentrated to yield a foam which was suspended in $Et_2O$ and concentrated to remove excess HCl. The resultant solid was resuspended in $Et_2O$, collected by vacuum filtration, washed with $Et_2O$ and dried under vacuum to give (23 g, 100%) of desired product. $^1H$ NMR ($CD_3OD$) of di-HCl salt: δ 2.59 (t, J=13.3 Hz, 2H), 2.93 (t, J=13.3 Hz, 2H), 3.07 (d, J=13.50 Hz, 2H), 3.58 (d, J=13 Hz, 2H), 4.26 (s, 2H), 7.56 (m, 10H).

Step 4: The product of Step 3 (24.10 g, 71 mM), $CH_2Cl_2$ (300 ml), (tBoc)$_2$O (17.0 g, 78.1 mM) and $Et_3N$ (14.37 g, 0.142 M) were combined and stirred under $N_2$, at rt, for 18 hrs. The reaction mixture was partitioned between $CH_2Cl_2$ and $H_2O$, and the aqueous layer was extracted with $CH_2Cl_2$. The combined organic layers were washed with water (2×), then brine, and dried ($MgSO_4$), filtered and concentrated. The resulting solid was suspended in $Et_2O$ and sonicated, filtered and dried to produce the desired compound (21.98 g, 90%). $^1H$ NMR ($CD_3OD$): δ 1.09 (bs, 2H), 1.39 (s, 1H), 2.05 (m, 2H), 2.34 (m, 4H), 2.65 (d, J=11.8 Hz, 2H), 3.56 (s, 2H), 7.18–7.40 (m, 10H).

Step 5: The product of Step 4 (5.22 g, 14.2 mM), $CH_3OH$ (430 ml). Pd(OH)$_2$/C (3.0 g) and $NH_4COOH$ (18.86 g, 0.298 M) were combined and refluxed under $N_2$ for 8 h. The reaction mixture was filtered using celite, washing with $CH_3OH$. The combined filtrates were concentrated to produce (3.90 g, 97%) of the desired product. $^1H$ NMR ($CD_3OD$): δ 1.10 (bs, 2H), 1.39 (s, 7H), 1.90 (m, 2H), 2.26 (m, 4H), 2.92 (m, 4H), 7.17–7.41 (m, 5H).

Step 6: The product of Step 5 (2.74 g, 9.91 mM), $CH_3CN$ (85 ml), $Et_3N$ (1.75 ml, 12.40 mM) and bromodiphenylmethane (2.70 g, 10.9 mM) were combined and stirred at rt under $N_2$ for 18 hrs. The mixture was concentrated and the resultant residue was partitioned between $H_2O$ and EtOAc. The EtOAc layer was washed with water (2×), brine, then dried ($MgSO_4$), filtered and concentrated. Chromatography (neutral $Al_2O_3$, hexane, then 4:1 hexane:EtOAc) gave 2.85 g (65%) of the desired product. $^1H$ NMR ($CD_3OD$): δ 1.07 (bs, 2H), 1.37 (s, 7H), 2.23 (m, 2H), 2.24 (m, 4H), 2.74 (d, J=12.1 Hz, 2H), 4.27 (s, 1H), 7.10–7.47 (m, 15H).

Step 7: The product of Step 6 (4.6 g, 10 mM), 1,4-dioxane (38 ml) and 4 M HCl in 1,4-dioxane (25 ml, 101 mM) were combined and stirred at rt under $N_2$ for 4 h. The mixture was concentrated and the residue was suspended in $Et_2O$ and re-concentrated. The resultant solid was resuspended in $Et_2O$, sonicated and the product was collected by vacuum filtration and dried to give 3.27 g (80% of the desired product. $^1H$ NMR ($CD_3OD$) of di-HCl salt: δ 2.91(m, 8H), 5.34 (s, 1H), 7.37–7.77 (m, 15H).

Step 8: To a suspension of the product of Step 7 (0.3 g, 0.722 mM) in $CH_2Cl_2$ (3 ml), under $N_2$ at rt, was added 2-thiophenecarboxaldehyde (0.133 ml, 1.44 mM). The pH of the reaction was adjusted to 6 with $Et_3N$ and the mixture was stirred for 0.5 h. Na(OAc)$_3$BH (0.230 g, 1.08 mM) was then added and the reaction mixture was stirred at rt under $N_2$ for 3 h. The reaction was quenched with saturated $NaHCO_3$(aq) and partitioned between $Et_2O$ and $H_2O$. The organic layer was washed with $H_2O$ (2×), brine, dried ($MgSO_4$), filtered and concentrated. Chromatography ($SiO_2$, toluene, then 1:19 EtOAc: toluene) gave 0.158 g (50%) of the desired product. $^1H$ NMR ($CD_3OD$): δ 1.96 (m, 2H), 2.17 (m, 2H), 2.52 (m, 4H), 3.45 (s, 2H), 4.24 (s, 1H), 6.76 (d. J=3.5 Hz, 1H), 6.85 (dd, J=3.6 Hz, 1H), 7.13–7.50 (m, 16H).

EXAMPLE 8

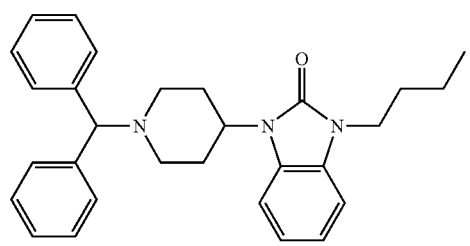

Step 1: Alkylate a solution of 4-(2-oxo-1-benzimidazolyl)-piperidine in $CH_3CN$ using the procedure described in Step 1 of Example 1 to produce the desired compound.

Step 2: Add NaH to a solution of 3-[1-(diphenylmethyl)-4-piperidinyl]-1,3-dihydro-2H-benzimidazo-1-one (2.5 g, 6.6 mmol) in DMF (25 ml) and stir at rt for 1 h. Add n-butyl iodide to the mixture at rt and stir overnight. Quench with ice-$H_2O$, extract with EtOAc, wash with $H_2O$ and brine, dry ($MgSO_4$) and concentrate. Chromatograph the residue on silica (1:9 EtOAc/hexane) to give the title compound (2.35 g). Dissolve the title compound in $Et_2O$, add HCl in $Et_2O$ (8 ml, 1 M), stir for 1 h and filter to give the HCl salt. $^1H$ NMR (CDCl$_3$) δ 7.55 (m, 4H, ArH), 7.35 (m, 5H, ArH), 7.25 (m, 2H, ArH), 7.15 (m, 2H, ArH), 7.1 (m, 1H, ArH), 4.4 (m, 2H), 3.95 (t, 2H), 3.15 (d, 2H), 2.6 (dq, 2H), 2.1 (t, 2H, 1.8, m, 4H), 1.5 (m, 2H), 1.0 (t, 3H); ESI-MS 440 (M+1); Elemental analysis for $C_{29}H_{33}N_3O$. HCl.$H_2O$: calcd: C, 70.5; H, 7.3; N, 8.5; Cl, 7.18; observed: C, 70.48; H, 7.28; N, 8.49; Cl, 7.49).

EXAMPLE 9

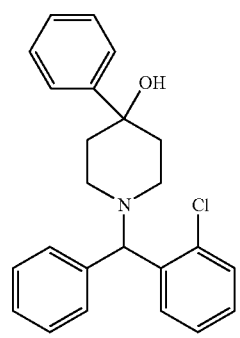

Add SOCl$_2$ (247 mg, 2.07 mmol) to a solution of 2-(chloro-phenyl)phenylmethanol (300 mg, 1.38 mmol) in $CH_2Cl_2$ at rt, stir at rt for 5 h and concentrate. Dissolve the residue in CH₃CN, add K₂CO₃, 4-hydroxy-4-phenylpiperidine and NaI. Stir the solution at reflux overnight, filter and concentrate. Chromatograph the residue on silica (9:1 hexane/EtOAc) to give the title compound. ¹H NMR (CDCl₃) δ 7.91 (d, 1H), 7.58 (d, 2H), 7.54 (d, 2H), 7.42 (t, 2H), 7.32 (m, 5H), 7.26 (t, 3H), 7.16 (t, 3H), 5.0 (s, 1H), 2.8 (dd, 2H), 2.5 (dq, 2H), 2.2 (dt, 2H), 1.75 (d, 2H). Dissolve the title compound in ether, add HCl/Et₂O (1 M) to give the HCl salt. MS Cl (378 (M+1); Elemental analysis for C₂₄H₂₄NOCl.HCl.0.2H₂O: calcd: C, 68.97; H, 6.13; N, 3.35; Cl, 16.96; observed: C, 68.87; H, 6.04; N, 3.35; Cl, 17.00.

EtOAc, wash with brine, dry and concentrate. Chromatograph the residue (95:5, 9:1 hexane/EtOAc) to give the title compound (330 mg). ¹H NMR (CDCl₃) δ 7.76 (d, 1H), 7.62 (d, 1H), 7.55 (d, 1H), 7.45 (t, 1H), 7.34 (m, 3H), 7.24 (m, 2H), 7.03 (t, 1H), 6.90 (d, 2H), 4.88 (s, 1H), 3.89 (s, 3H), 2.94 (d, 1H), 2.82 (d, 1H), 2.45 (td, 2H), 2.26 (t, 2H), 1.78 (d, 2H). Dissolve the title compound in Et₂O, add HCl in Et₂O, stir for 1 h and filter to give the HCl salt. MS FAB 374.1 (M+1); elemental analysis for C₂₅H₂₇NO₂.HCl.0.15H₂O: calcd: C, 72.77; H, 6.91; N, 3.39; Cl, 8.59; obserbed: C, 72.76; H, 7.02; N, 3.59; Cl, 8.83.

EXAMPLE 10

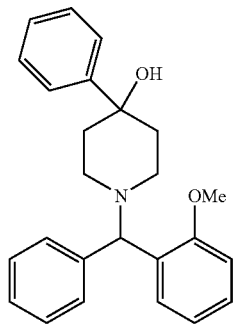

Step 1: Alkylate a solution of 4-piperidone monohydrate hydrochloride (880 mg, 5 mmol) in CH₃CN with mandelonitrile (1 g, 7.51 mmol) using the procedure described in Example 9. Chromatography of the residue on silica followed by recrystallization (EtOAc) gives the desired compound (630 mg).

Step 2: Add a solution of 2-methoxyphenylmagnesium bromide in THF (24 ml, 0.5 M, 11.85 mmol) to a solution of the product of Step 1 (330 mg, 1.185 mmol) in THF at 0° C. Remove the ice-bath and stir the reaction mixture at reflux for 6 h. Quench the reaction with NH₄Cl (aq), extract with

EXAMPLE 11

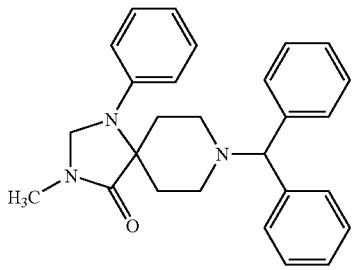

Step 1 Alkylate a solution of 1-phenyl-1,3,8-triazaspiro[4,5]decan-4-one (0.5 g) in CH₃CN using the procedure described in Step 1 of Example 1 to produce desired compound.

Step 2 Alkylate the product from Step 1, 1-phenyl-8-(diphenylmethyl)-1,3,8-triazaspiro[4,5]decan-4-one (0.4 g) with CH₃I using the procedure described in Step 2 of Example 1 to produce the title compound (0.25 g). ¹H NMR (CDCl₃) δ 1.70 (d, 2H), 2.85 (m, 6H), 3.05(s, 3H), 4.50 (s, 1H), 4.72 (s, 2H), 6.95 (t, 1H), 7.05(d 2H), 7.20–7.60 (m, 12H).

Using the procedures of Examples 1 to 11, employing the appropriate starting material, compounds shown in the following tables are prepared.

TABLE 1

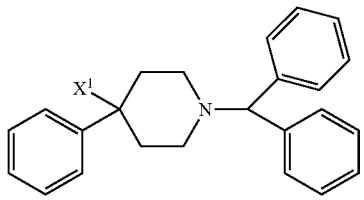

wherein X¹ is as defined below:

| X¹ | Physical Data |
|---|---|
| H | C₂₄H₂₅N |
|  | FAB 283.3 (100), 167.2 52) |
| OMe | C₂₅H₂₇NO |
|  | FAB 358 (80), 167 (70) |
| OEt | C₂₆N₂₉NO: HCl |
|  | FAB 342 (67) 167 (100) |
| 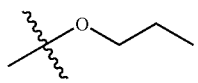 | C₂₇H₃₁NO |
|  | ESI 386.1 (79), 167 (100) |

TABLE 1-continued
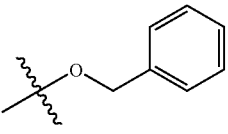
wherein X¹ is as defined below:
| X¹ | Physical Data |
|---|---|
| 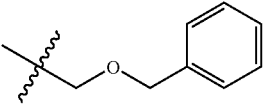 | $C_{31}H_{31}NO$: HCl<br>ESI 434.2 (62), 167 (100) |
| CN | $C_{25}H_{24}N_2$<br>FAB 353.2 (53), 275.10 (24). |
| CHO | $C_{25}H_{25}NO$<br>Cl 356 (28), 167 (100) |
| CH₂OH | $C_{25}H_{27}NO$<br>Cl 358.1 (37), 167 (100) |
| 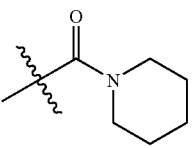 | $C_{32}H_{33}NO$:HCl<br>FAB 448.1 (46), 167.2 (100) |
| CH₂OMe | $C_{25}H_{27}NO$<br>FAB 357.10 (10), 167 (100) |
| CH₂OEt | $C_{26}H_{29}NO$<br>Cl 373.3 (12), 372 (42), 167 100) |
| 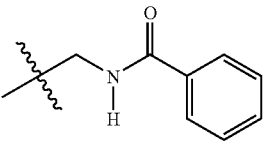 | $C_{30}H_{34}NO$<br>Cl 440.25 (33), 439.2 (100), 167.2 (89) |
| CH₂NH₂ | $C_{25}H_{28}N_2$:2HCl<br>ESI 357.10 (37), 167 (100) |
| CH₂NHCOCH₃ | $C_{27}H_{30}N_2O$<br>ESI 399.1 (53), 167.0 (100) |
| 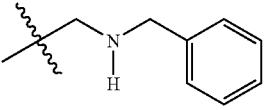 | $C_{32}H_{32}N_2O$<br>FAB 462.1 (15), 461.1 (41), 393 (8) |
| 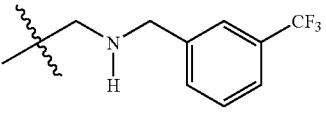 | $C_{32}H_{34}N_2$:HCl<br>ESI 447.1 (100), 281.1 (29) |
| 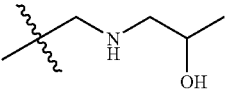 | $C_{33}H_{32}N_2F_3$:HCl<br>ESI 515 (100), 349.10 (33), 167 (49) |
| CH₂NHCH₂CH₃ | $C_{27}H_{32}N_2$:HCl<br>ESI 385.1 (100), 219.10 (26), 167 (76) |
|  | $C_{29}H_{36}N_2O$:HCl<br>Cl 429 (53), 351 (100) 327 (13), 167 (34) |

TABLE 1-continued
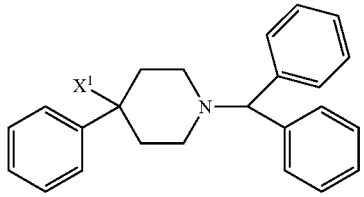
wherein X¹ is as defined below:
| X¹ | Physical Data |
|---|---|
| 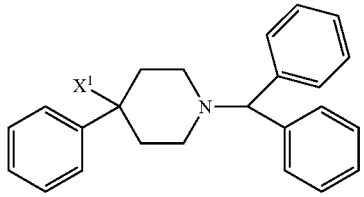 | $C_{28}H_{32}N_2O_2$<br>Cl 429 (100), 351 (9), 261 (11), 167 (81) |
| 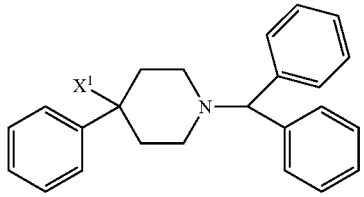 | $C_{28}H_{34}N_2O$:HCl<br>Cl 415 (100), 327 (33), 167 (65) |
| 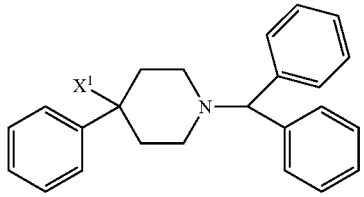 | $C_{31}H_{39}N_3O$:HCl<br>ESI 470 (100), 304 (51), 259 (16), 167 (46) |
| 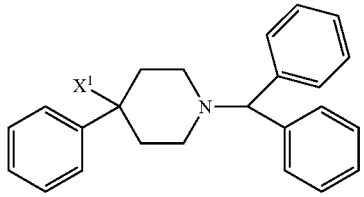 | $C_{31}H_{41}N_3$:HCl<br>ESI 456 (100), 290 (11), 167 (11) |
| 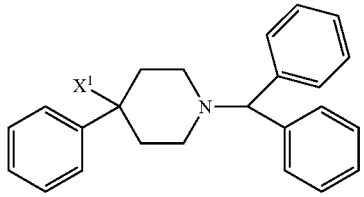 | $C_{30}H_{30}N_2O_2$<br>ESI 451 (100), 283 (8), 167 (94) |
| 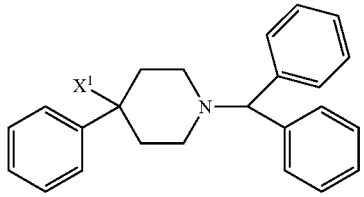 | $C_{34}H_{43}N_3O$: HCl<br>ESI 510 (88), 344 (73), 167 (100) |
| 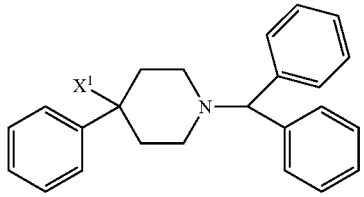 | $C_{32}H_{41}N_3$:HCl<br>ESI 468 (98), 302 (22), 167 (100) |
| 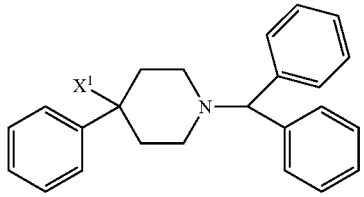 | $C_{31}H_{31}N_3O$:HCl<br>Cl 462 (100), 384 (4), 167 (45) |
| 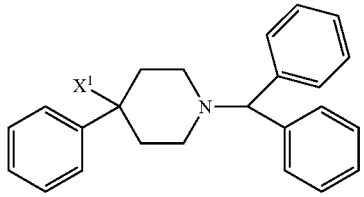 | $C_{30}H_{32}N_2O$:Cl<br>ESI 437 (100), 271 (11), 167 (41) |
|  | $C_{30}H_{32}N_2O$:HCl<br>ESI 437 (87), 271 (7), 167 (100) |

TABLE 1-continued
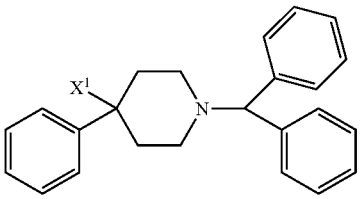
wherein X¹ is as defined below:
| X¹ | Physical Data |
|---|---|
| 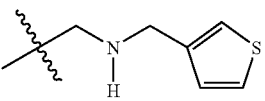 | $C_{30}H_{32}N_2S$:HCl<br>ESI 453 (92), 167 (100) |
| 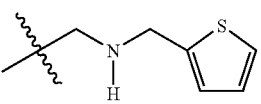 | $C_{30}H_{32}N_2S$:HCl<br>ESI 453 (100), 287 (6), 167 (78) |
| 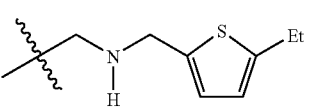 | $C_{32}H_{36}N_2S$:HCl<br>ESI 481 (69), 340 (5), 167 (100) |
| 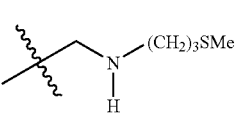 | $C_{29}H_{36}N_2S$:HCl<br>ESI 445 (100), 399 (3), 279 (11), 167 (84) |
| 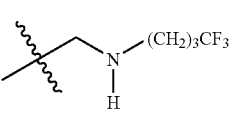 | $C_{29}H_{33}N_2F_3$:HCl<br>ESI 467 (69), 167 (100) |
| $CH_2NMe_2$ | $C_{27}H_{32}N_2$:HCl<br>FAB 385.3 (100), 219.2 (6), 162.2 (77) |
| $NH_2$ | $C_{24}H_{26}N_2$:HCl<br>ESI 343 (48), 326 (70), 167 (100) |
| $NH(CH_2)_3NEt_2$ | $C_{31}H_{41}N_3$:HCl<br>ESI 456 (72), 326 (74), 167 (100) |
| 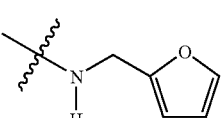 | $C_{29}H_{30}N_2O$:HCl<br>Cl 423 (60), 326 (100), 167 (74) |
| 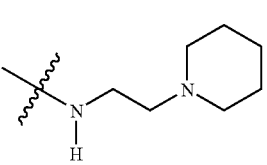 | $C_{31}H_{39}N_3$:HCl<br>ESI 454 (76), 326 (60), 167 (100) |
| 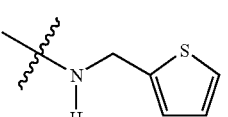 | $C_{29}H_{30}N_2S$:HCl<br>FAB 439 (90), 326 (25), 167 (100) |
| NHMe | $C_{25}H_{28}N_2$:HCl<br>ESI 357 (20), 326 (87), 167 (100) |
| $NMe_2$ | $C_{26}H_{30}N_2$:HCl<br>ESI 371 (11), 326 (81), 167 (100) |

TABLE 2
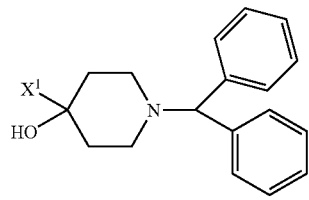
wherein X[1] is as defined below
| X[1] | Physical Data |
|---|---|
| phenyl | $C_{24}H_{25}NO$<br>FAB 343.1 (13), 342.1 (26) |
| 4-Br-phenyl | $C_{24}H_{24}BrNO$<br>ESI 424 (20) 422 (18) 167-2 (92) |
| 4-Cl-phenyl | $C_{24}H_{24}NOCl$<br>Cl 363 (43), 362 (22), 167.20 (100) |
| 4-F-phenyl | $C_{24}H_{24}FNO$<br>361 (22), 167.2 (75) |
| Benzyl | $C_{25}H_{27}NO$<br>Cl 358.1 (62), 167 (78) |
| n-Propyl-phenyl | $C_{27}H_{31}NO \cdot HCl$<br>FAB 386.1 (46), 167 (100) |
| 4-Cl-3-CF$_3$-phenyl | $C_{25}H_{23}NOF_3Cl$<br>EI 369 (3), 368 (14), 167 (100) |
| 3-CF$_3$-phenyl | $C_{25}H_{24}F_3NO$<br>FAB 413 (31), 412 (57), 167 (100) |
| 4-MeO-phenyl | $C_{25}H_{27}NO_2$<br>Cl 374.45 (M + 1), 266.30 (39%), 167.25 (100%) |
| 4-Me$_2$N-phenyl | $C_{26}H_{30}N_2O$<br>FAB 387 (86%), 369 (22%) |

TABLE 2-continued
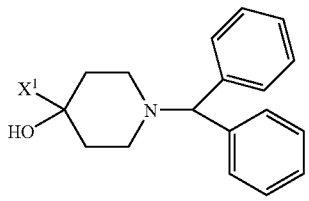
wherein X¹ is as defined below
| X¹ | Physical Data |
|---|---|
| Me–⟨F⟩–⟨⟩⤳ (4-Me, 3-F phenyl) | $C_{25}H_{26}NOF$<br>FAB 376.2 (68%), 375.2 (32%). 358.20 (6) |
| MeO–⟨⟩⤳ (3-MeO phenyl) | $C_{25}H_{27}NO_2$<br>Cl 374.45 (58%), 375.45 (27), 356.35 (29) |
| Cl–⟨⟩⤳ (3-Cl phenyl) | $C_{24}H_{24}ClNO$<br>Cl 378.35 (31%), 377.35 (18%), 360.30 (22) |
| Me–⟨⟩⤳ (3-Me phenyl) | $C_{25}H_{27}NO$<br>Cl 358.35 (68), 357.35 (38), 340.35 (47), 167.25 (100) |
| F–⟨F⟩⤳ (3,5-diF phenyl) | $C_{24}H_{23}F_2NO$<br>Cl 380.35 (28%), 379.35 (22), 362.35 (23), 167.25 (100) |
| Me–⟨⟩⤳ (4-Me phenyl) | $C_{25}H_{27}NO$<br>Cl 358.35 (63), 357.35 (43), 340.35 (53), 167.25 (100) |
| ⟨Me⟩⤳ (2-Me phenyl) | $C_{25}H_{27}NO$<br>Cl 358.35 (49), 357.35 (41), 340.35 (35), 167.25 (100) |
| F–⟨⟩⤳ (3-F phenyl) | $C_{24}H_{24}FNO$<br>Cl 362.35 (41), 361.35 (218), 344.35 (39), 167.25 (100) |

TABLE 2-continued

[Structure: 1-benzhydryl-4-hydroxy-4-X¹-piperidine]

wherein X¹ is as defined below

| X¹ | Physical Data |
|---|---|
| phenylethynyl- | C₂₆H₂₅NO<br>FAB 368 (37), 367 (38), 366 (100), 290 (41) |
| 2-methoxyphenyl- | C₂₅H₂₇NSO<br>FAB 375 (10), 374.20 (40), 306.7 (13) |
| 4-(methylthio)phenyl- | C₂₅H₂₇NSO<br>FAB 390 (22), 389(27), 388 (100), 312 (48) |
| 3,4-difluorophenyl- | C₂₄H₂₃NOF₂<br>380.2 (11), 379.2 (16), 378.2 (31) |
| 4-ethylphenyl- | C₂₆H₂₉NO<br>Cl 373.45 (22), 372.40 (82), 354.35 (60), 167.25 (100) |
| cyclohexyl- | C₂₄H₃₁NO<br>FAB 350.3 (4), 349.3 (7), 348 917) |
| n Hexyl | C₂₄H₃₃NO<br>FAB 352 (85), 274 (189) |
| n propyl | C₂₇H₃₁NO<br>ESI 386 (70), 167 (100) |
| n butyl | C₂₈H₃₃NO<br>ESI 400.1 (68), 167 (100) |
| 2-methylallyl- (isopropenyl) | C₂₁H₂₅NO:HCl<br>ESI 308.1 (32), 167.0 (100) |
| 2-furyl- | C₂₂H₂₃NO₂:HCl<br>Cl 334.25 (34), 333.25 (26), 316.25 (41), 167.25 (100) |

TABLE 2-continued wherein X¹ is as defined below

| X¹ | Physical Data |
|---|---|
| (2-thienyl-methyl) | $C_{22}H_{23}NOS:HCl$<br>CI 350.25 (32), 349.35 (24), 332.25 (41), 167.25 (100) |
| (3-thienyl-methyl) | $C_{22}H_{23}NOS:HCl$<br>CI 350.25 (27), 349.35 (18), 332.25 (20), 167.25 (100) |
| (2-pyridyl-methyl) | $C_{23}H_{24}N_2O:HCl$<br>ESI 345.1 (68), 167 (100) |
| (3-furyl-methyl) | $C_{22}H_{23}NO_2$<br>CI 334.25 (37), 333.25 (24), 316.25 (31), 167.25 (100) |
| (4-cyanophenyl-methyl) | $C_{25}H_{24}N_2O:HCl$<br>FAB 369.3 (3), 368.3 (6), 367.3 (13) |
| (isobutyl-methyl) | $C_{21}H_{27}NO:HCl$<br>CI 310.40 (38), 309.40 (25), 292.40 (33), 167.25 (100) |
| (2-fluorophenyl-methyl) | $C_{24}H_{24}NOF:HCl$<br>FAB 362.1 (100), 232.1 (11) |
| (tert-butyl-methyl) | $C_{22}H_{29}NO:HCl$<br>FAB 324.30 (100) |
| (cyclopropyl-methyl) | $C_{21}H_{25}NO:HCl$<br>CI 308.2 (64), 307.2 (30), 290.2 (57), 167.25 (100) |

TABLE 2-continued

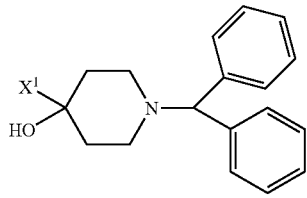

wherein $X^1$ is as defined below

| $X^1$ | Physical Data |
|---|---|
| 3-methylthiophen-2-yl (Me on thiophene) | $C_{23}H_{25}NOS:HCl$<br>Cl 364.15 (69), 346.15 (71), 167.25 (100) |
| thiazol-2-yl | $C_{21}H_{22}N_2SO:HCl$<br>Cl 351.1 (52), 350.1 (8), 266.15 (12), 167.2 (100) |
| 1-methylindol-2-yl | $C_{27}H_{28}N_2O:HCl$<br>FAB 397.2 (80), 167.2 (100) |
| 2-(aminomethyl)phenyl (CH$_2$NH$_2$) | $C_{25}H_{28}N_2O:HCl$<br>ESI 373.1 (28), 167 (100) |
| 2-(hydroxymethyl)phenyl (CH$_2$OH) | $C_{25}H_{27}NO_2:HCl$<br>ESI 374.1 (43), 167 (100) |

TABLE 3

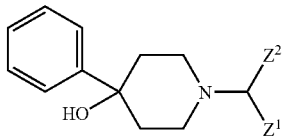

wherein $Z^1$ and $Z^2$ are as defined below:

| $Z^1$ | $Z^2$ | Physical Data |
|---|---|---|
| 4-chlorophenyl | phenyl | $C_{24}H_{24}NOCl$<br>Cl 380 (30), 378.1 (100), 201 (100) |
| 4-fluorophenyl | 4-fluorophenyl | $C_{24}H_{23}NOF_2$<br>Cl 380.15 (79), 379.15 (47), 362.05 (100) |

TABLE 3-continued
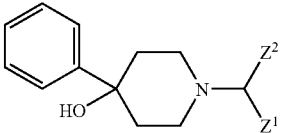
wherein Z¹ and Z² are as defined below:
| Z¹ | Z² | Physical Data |
|---|---|---|
| 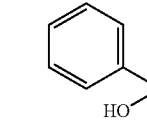 | 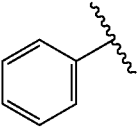 | $C_{23}H_{24}N_2O$:HCl<br>ESI 345.1 (69), 327.1 (49), 168 (100) |
| 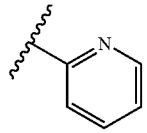 | 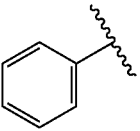 | $C_{25}H_{24}N_2O$:HCl<br>ESI 345.1 (58), 168 (100) |
| 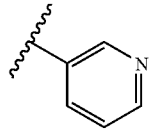 | 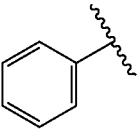 | $C_{25}H_{27}NO$:HCl<br>Cl 358.20 (60), 340.20 (51), 181.25 (100) |
| 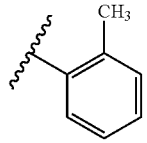 | 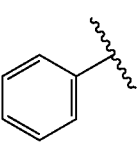 | $C_{24}H_{24}NOBr$:HCl<br>ESI 424.1 (17), 422 (17), 247.1 (100), 245.1 (99) |
| 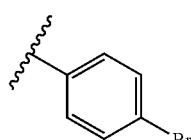 | 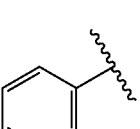 | $C_{25}H_{27}NO$:HCl<br>ESI 358.1 (32.70), 181 (100) |
| 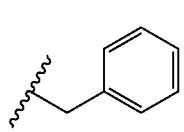 | 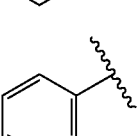 | $C_{24}H_{24}NOCl$:HCl<br>Cl 380.10 (30), 378.15 (100) |
| 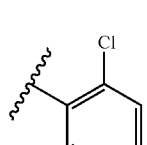 | 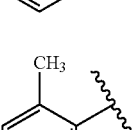 | $C_{26}H_{29}NO$:HCl<br>ESI 372,1 (24), 195.1 (100) |
| 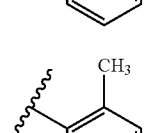 | 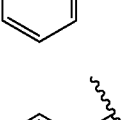 | $C_{25}H_{27}NO$:HCl<br>ESI 358.1 (48%), 181.1 (100) |
| 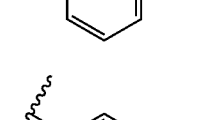 | 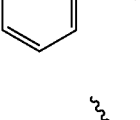 | $C_{25}H_{24}ONF_3$:HCl<br>ESI 412.1 (56), 235 (100) |

TABLE 3-continued
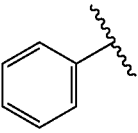
wherein $Z^1$ and $Z^2$ are as defined below:
| $Z^1$ | $Z^2$ | Physical Data |
|---|---|---|
| 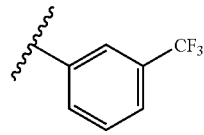 | 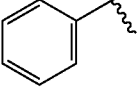 | $C_{25}H_{24}ONF_3$:HCl<br>ESI 412.1 (73), 235.1 (100) |
| 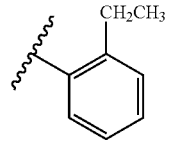 | 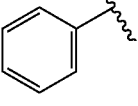 | $C_{26}H_{29}NO$:HCl<br>ESI 372.1 (39), 195.1 (100) |
| 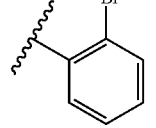 | 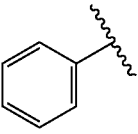 | $C_{24}H_{24}NOBr$:HCl<br>ESI 424.10 (48), 422.1 (47), 245.1 (100) |
| 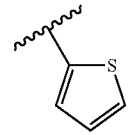 | 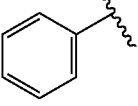 | $C_{22}H_{23}NOS$:HCl<br>ESI 350.1 (31), 173 (100) |
| 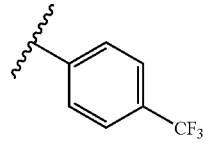 | 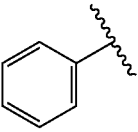 | $C_{25}H_{24}ONF_3$:HCl<br>ESI 412.1 (54), 235.10 (100) |
| 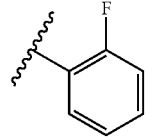 | 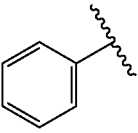 | $C_{24}H_{24}NOF$:HCl<br>ESI 362.1 (23), 185.1 (100) |
| 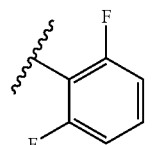 | 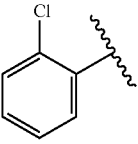 | $C_{24}H_{23}NOF$:HCl<br>Cl 380.15 (100), 362.15 (89), 203.25 (99) |
| 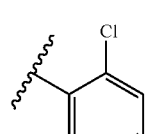 |  | $C_{24}H_{23}NOCl_2$:HCl<br>ESI 416.1 (7), 414 (32), 412 (45), 235.1 (100) |

TABLE 3-continued
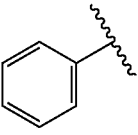
wherein Z¹ and Z² are as defined below:
| Z¹ | Z² | Physical Data |
|---|---|---|
| 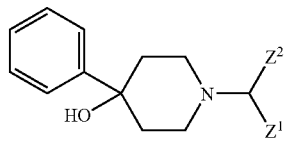 | 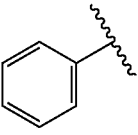 | $C_{25}H_{24}N_2O_2F_2$:HCl<br>FAB 423.2 (100), 218.0 (18) |
| 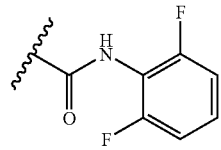 | 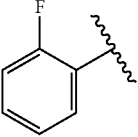 | $C_{24}H_{23}NOF_2$:HCl<br>Cl 380.15 (79), 379.15 (45), 362.05 (100) |
| 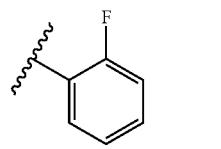 | 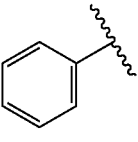 | $C_{26}H_{29}NO_2$:HCl<br>FAB 388.3 (100), 266.1 (15) |
| 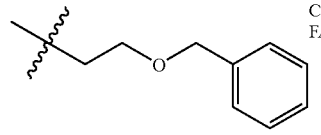 | 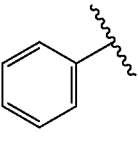 | $C_{25}H_{27}NO_2$:HCl<br>FAB 374.1 (100), 197 (73) |
| 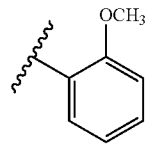 | 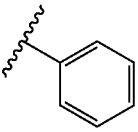 | $C_{24}H_{24}NOCl$:HCl<br>FAB 380.1 (27), 378.2 (80), 201.0 (100) |
| 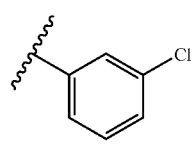 | 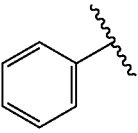 | $C_{25}H_{27}NO$:HCl<br>ESI 358.1 (15), 181.1 (100) |
| Methyl | 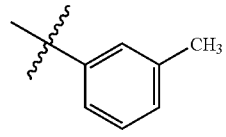 | $C_{19}H_{23}NO$:HCl<br>ESI 282.1 (100), 160.0 (84.5) |
| Ethyl | 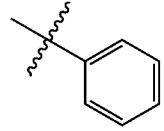 | $C_{20}H_{25}NO$:HCl<br>ESI 296.1 (100), 160.0 (84) |
| 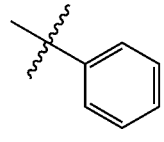 |  | $C_{21}H_{27}NO$:HCl<br>ESI 310.1 (100), 160.1 (52) |

TABLE 3-continued wherein $Z^1$ and $Z^2$ are as defined below:

| $Z^1$ | $Z^2$ | Physical Data |
|---|---|---|
| n-butyl | phenyl | $C_{22}H_{29}NO:HCl$<br>ESI 324.1(100), 160.1 (52) |
| n-pentyl | phenyl | $C_{23}H_{31}NO:HCl$<br>Cl 338.3 (100), 266.20 (77), 160.35 (17) |
| n-hexyl | phenyl | $C_{24}H_{33}NO:HCl$<br>ESI 352.1 (100), 160.0 (41.83) |
| cyclopentyl | phenyl | $C_{23}H_{29}NO:HCl$<br>ESI 336.1 (66.39), 160.0 (63), 159 (100) |
| morpholinomethyl | phenyl | $C_{23}H_{30}N_2O_2:HCl$<br>ESI 367.1 (35), 190 (100) |
| isohexyl | phenyl | $C_{23}H_{31}NO:HCl$<br>ESI 338.1 (100), 161.0 (36), 160 (70) |

TABLE 4 wherein $X^1$, $X^2$, $Z^1$ and $Z^2$ are as defined below

| $X^1$ | $X^2$ | $Z^1$ | $Z^2$ | Physical Data |
|---|---|---|---|---|
| α-methylbenzyl | $NH_2$ | n-butyl | phenyl | $C_{22}H_{30}N_2:HCl$<br>ESI 323 (71), 306 (100), 160 (31) |

TABLE 4-continued wherein X¹, X², Z¹ and Z² are as defined below

| X¹ | X² | Z¹ | Z² | Physical Data |
|---|---|---|---|---|
| phenyl | -CH₂-NH-CH₂-(2-thienyl) | pentyl | phenyl | $C_{27}H_{34}N_2S$:HCl ESI 419 (23), 306 (100) |
| phenyl | CH₂NH₂ | pentyl | phenyl | $C_{23}H_{32}N_2$:HCl ESI 337 (96), 174 (100), 160 (19) |
| phenyl | -CH₂-NH-CH₂-(3-thienyl) | pentyl | phenyl | $C_{28}H_{36}N_2S$:HCl ESI 433 (100), 320 (65), 174 (58) |
| phenyl | NH₂ | 2-methylphenyl | phenyl | $C_{25}H_{28}N_2$:HCl Cl 357 (47), 340 (24), 279 (8), 181 (100) |
| phenyl | -CH₂-NH-CH₂-(2-thienyl) | pentyl | phenyl | $C_{28}H_{36}N_2S$:HCl ESI 433 (100), 320 (42), 174 (77) |
| phenyl | -CH₂-NH-CH₂-(2-thienyl) | 2-methylphenyl | phenyl | $C_{30}H_{32}N_2S$:HCl ESI 453 (24), 340 (27), 181 (100) |
| phenyl | NH₂ | 2-methylphenyl | 2-methylphenyl | $C_{26}H_{30}N_2$:HCl ESI 371 (16) 195 (100) |
| phenyl | -CH₂-NH-CH₂-(2-thienyl) | 2-methylphenyl | 2-methylphenyl | $C_{31}H_{34}N_2S$:HCl ESI 467 (25), 354 (30), 195 (100) |
| phenyl | NH₂ | 2-chlorophenyl | 2-chlorophenyl | $C_{24}H_{24}N_2Cl_2$:HCl ESI 413 (18), 411 (26), 396 (39), 394 (51), 237 (69), 235 (100) |

TABLE 4-continued

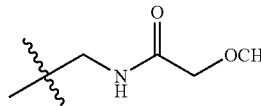

wherein X¹, X², Z¹ and Z² are as defined below

| X¹ | X² | Z¹ | Z² | Physical Data |
|---|---|---|---|---|
| 4-Br-phenyl | OH | 2-methylphenyl | 2-methylphenyl | $C_{26}H_{28}BrNO\cdot HCl$ 450 (12), 195.1 (100) |
| 4-F-phenyl | OH | 2-methylphenyl | 2-methylphenyl | $C_{26}H_{28}FNO\cdot HCl$ ESI 390.1 (9.6), 195.1 (100) |
| 4-Cl-phenyl | OH | 2-methylphenyl | 2-methylphenyl | $C_{26}H_{28}ClNO\cdot HCl$ 407.1 (5), 195.1 (100) 406.1 (16) |
| phenyl | -NHC(O)-(2-thienyl) | 2-methylphenyl | 2-methylphenyl | $C_{31}H_{32}N_2OS$ ESI 481 (25), 195 (100) |
| phenyl | -NHC(O)CH₃ | 2-methylphenyl | 2-methylphenyl | $C_{28}H_{32}N_2O$ Cl 413 (31), 354 (8), 195 (100) |
| phenyl | -NHCH₂-(2-thienyl) | 2-Cl-phenyl | 2-Cl-phenyl | $C_{29}H_{28}Cl_2N_2S\cdot HCl$ ESI 509 (10), 507 (14), 396 (56), 394 (77), 237 (68), 235 (100) |
| 2-(aminomethyl)phenyl | OH | 2-Cl-phenyl | 2-Cl-phenyl | $C_{25}H_{26}N_2OCl_2\cdot HCl$ ESI 443 (42), 441 (56), 425 (31), 235 (100) |
| phenyl | -NHC(O)CH₂CH₂SCH₃ | 2-methylphenyl | 2-methylphenyl | $C_{30}H_{36}N_2OS$ ESI 473 (39), 195 (100) |
| phenyl | -NHC(O)-phenyl | 2-methylphenyl | 2-methylphenyl | $C_{33}H_{34}N_2O$ ESI 475 (41), 195 (100) |

TABLE 4-continued wherein $X^1$, $X^2$, $Z^1$ and $Z^2$ are as defined below

| $X^1$ | $X^2$ | $Z^1$ | $Z^2$ | Physical Data |
|---|---|---|---|---|
| phenyl | -NHC(O)CH₂OCH₃ | o-tolyl | o-tolyl | $C_{29}H_{34}N_2O_2$ ESI 443 (31), 195 (100) |
| phenyl | -NHC(O)-cyclopropyl | o-tolyl | o-tolyl | $C_{30}H_{34}N_2O$:HCl ESI 439 (17), 195 (100) |
| phenyl | -NHC(O)CH₂CH₂-cyclopentyl | o-tolyl | o-tolyl | $C_{34}H_{42}N_2O$:HCl ESI 495 (30), 195 (100) |
| phenyl | -NHCH₂-phenyl | o-tolyl | o-tolyl | $C_{33}H_{36}N_2$:HCl ESI 461 (17), 354 (28), 195 (100) |
| phenyl | -NHC(O)CH₃ | o-tolyl | o-chlorophenyl | $C_{26}H_{26}N_2OCl_2$ ESI 455 (57), 453 (75), 396 (7), 394 (10), 237 (73), 235 (100) |
| 2-(N-trifluoroacetyl-aminomethyl)phenyl | OH | o-tolyl | o-tolyl | $C_{29}H_{31}N_2O_3F_3$:HCl FAB 497.2 (507), 195.1 (100) |
| phenyl | -NHC(O)CH₃ | phenyl | n-butyl | $C_{24}H_{32}N_2O$:HCl ESI 365 (100), 219 (31), 160 (23) |
| phenyl | -NHC(O)CH₃ | phenyl | o-tolyl | $C_{27}H_{30}N_2O$:HCl ESI 399 (60), 181 (100) |

TABLE 4-continued
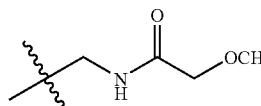
wherein X¹, X², Z¹ and Z² are as defined below
| X¹ | X² | Z¹ | Z² | Physical Data |
|---|---|---|---|---|
| 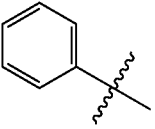 | 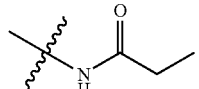 | 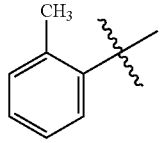 | 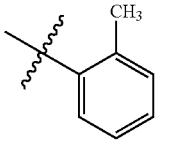 | $C_{29}H_{34}N_2O$:HCl ESI 427 (41), 195 (100) |
| 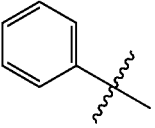 | 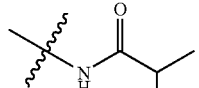 | 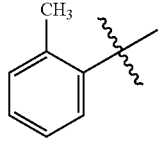 | 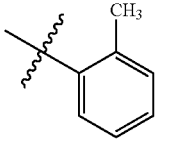 | $C_{30}H_{36}N_2O$:HCl ESI 441 (47), 195 (100) |
| 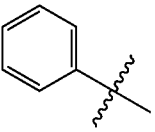 | 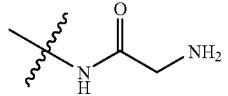 | 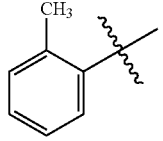 | 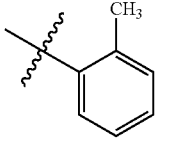 | $C_{28}H_{32}N_3O$:HCl ESI 428 (41), 195 (100) |
| 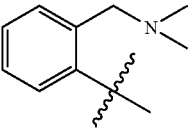 | OH | 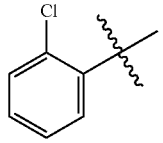 | 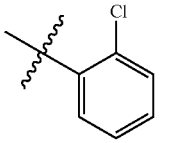 | $C_{27}H_{30}Cl_2N_2O$ FAB 469.2 (30), 235.1 (100) |
| 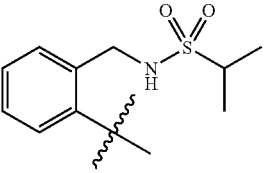 | OH | 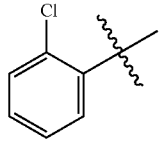 | 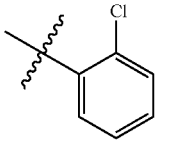 | $C_{28}H_{32}Cl_2N_2O_3S$ Cl 549.15 (69), 548.15 (37), 547.15 (100) |
| 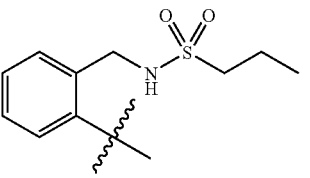 | OH | 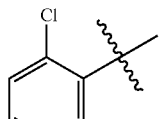 | 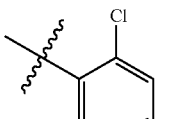 | $C_{28}H_{32}Cl_2N_2O_3S$ FAB 549 (60), 547.1 (87) |
| 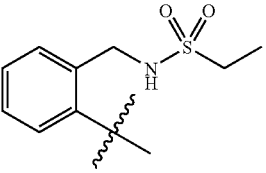 | OH | 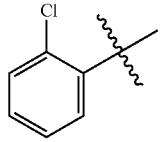 | 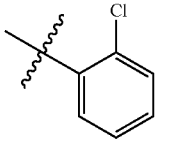 | $C_{27}H_{30}Cl_2N_2O_3S$ FAB FAB 535 (78), 533 (100) |
| 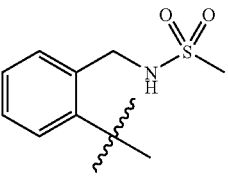 | OH | 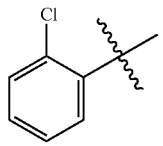 | 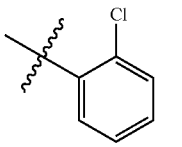 | $C_{26}H_{28}Cl_2N_2O_3S$ FAB 523 (25) |

TABLE 4-continued
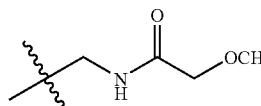
wherein X¹, X², Z¹ and Z² are as defined below
| X¹ | X² | Z¹ | Z² | Physical Data |
|---|---|---|---|---|
| 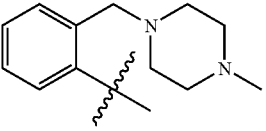 | OH | 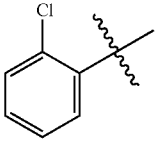 | 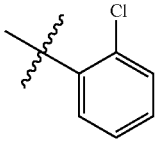 | $C_{30}H_{35}Cl_2N_3O$ FAB 524.40 (20), 330.3 (100) |
| 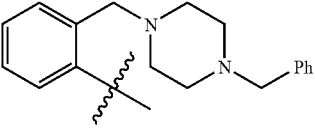 | OH | 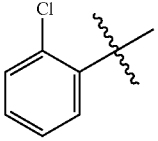 | 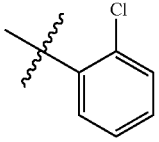 | $C_{36}H_{39}Cl_2N_3O$ FAB 600.5 (50), 330.4 (70) |
| 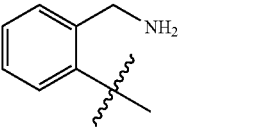 | OH | 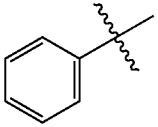 | 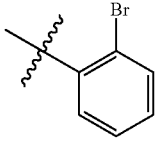 | $C_{25}H_{27}BrN_2O$ FAB 453.2 (100), 245 (100) |
| 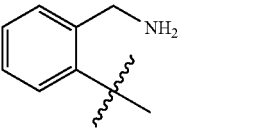 | OH | 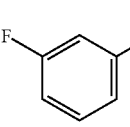 | 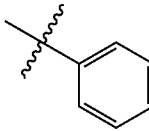 | $C_{25}H_{26}N_2F_2O$ FAB 410.2 (25), 409.2 (100), 203.2 (50) |
| 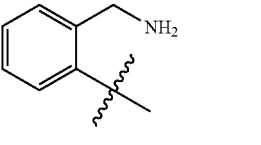 | OH | 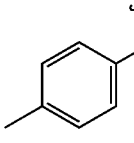 | 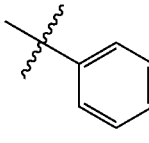 | $C_{27}H_{32}N_2O$ FAB 401.2 (95), 195 (100) |
| 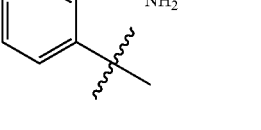 | OH | 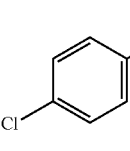 | 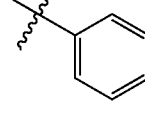 | $C_{25}H_{26}Cl_2N_2O$ 441.1 (40), 235 (42), 157 (100) |
| 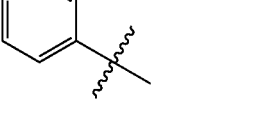 | OH | 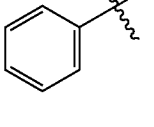 | 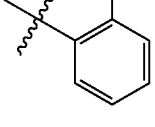 | $C_{25}H_{27}NO_2$ Cl 374.25 (52), 356.2 (100), 178.25 (40), 160.25 (57) |
| 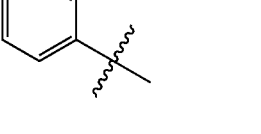 | OH | 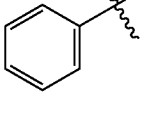 | 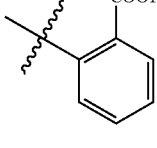 | $C_{25}H_{25}NO_3$ FAB 388.23 (100), 210.8 (21), 168.28 (20) |
| 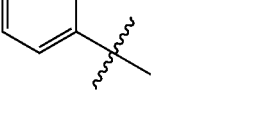 | OH | 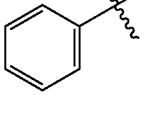 | —$(CH_2)_4CH_3$ | $C_{24}H_{34}N_2O$ FAB 368.3 (30), 367.3 (100) |

TABLE 4-continued
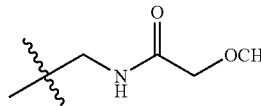
wherein X¹, X², Z¹ and Z² are as defined below
| X¹ | X² | Z¹ | Z² | Physical Data |
|---|---|---|---|---|
| 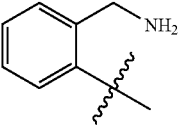 | OH | 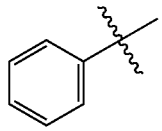 | —CH₂)₃CH₃ | $C_{23}H_{32}N_2O$<br>GAB 353.3 (100) |
| 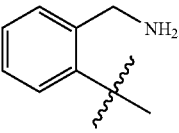 | OH | 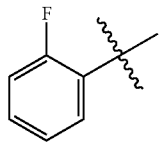 | 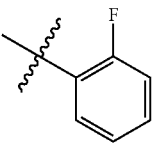 | $C_{25}H_{26}N_2F_2O$<br>FAB 410.6 (35),<br>409.4 (98), 203.1 (65) |
| 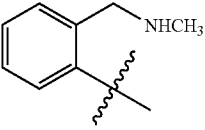 | OH | 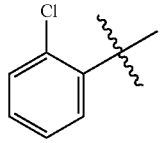 | 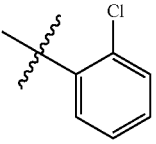 | $C_{26}H_{28}Cl_2N_2O$<br>FAB 457.3 (70),<br>455.3 (100), 237 (30), 235.1 (52) |
| 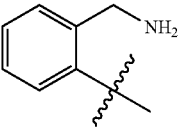 | OH | H | 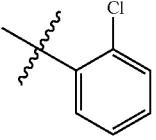 | $C_{19}H_{23}N_2OCl$<br>FAB 331.2 (100), |
| 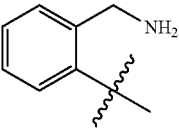 | OH | 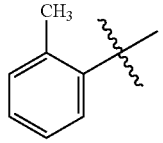 | 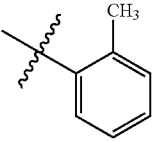 | $C_{27}H_{32}N_2O$<br>FAB 402.1 (20.46),<br>401.1 (44.89), 195.1 (100) |
| 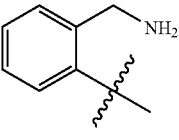 | OH | 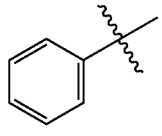 | 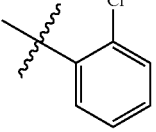 | $C_{25}H_{27}ClN_2O$<br>ES 409.2 (55),<br>408.2 (45), 407.2 (95) |
| 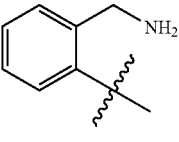 | OH | 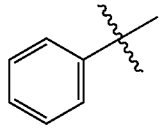 | 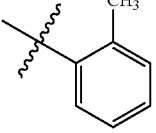 | $C_{26}H_{30}N_2O$<br>ES 387 (100) |
| 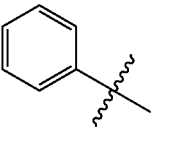 | OH | 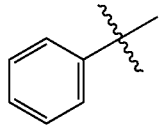 | 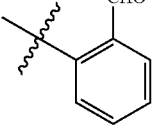 | $C_{25}H_{25}NO_2$<br>CI 372.15 (100),<br>354.15 (38), 195.15 (37) |
| 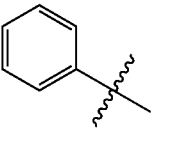 | OH | 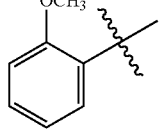 | 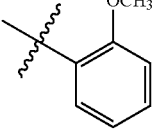 | $C_{26}H_{29}NO_3$<br>FAB 404.3 (100),<br>227.1 (70) |

TABLE 4-continued
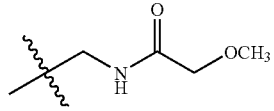
wherein X¹, X², Z¹ and Z² are as defined below
| X¹ | X² | Z¹ | Z² | Physical Data |
|---|---|---|---|---|
| 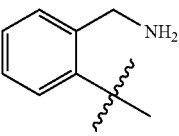 | OH | H | 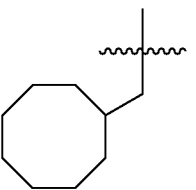 | $C_{21}H_{34}N_2O$<br>FAB 331.4 (100),<br>266.2 (20) |
| 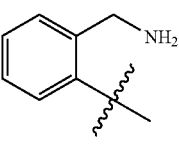 | OH | $CH_3(CH_2)_3$— | | $C_{24}H_{32}N_2O$<br>FAB 367.2 (100) |
| 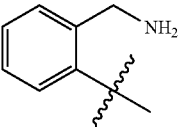 | OH | 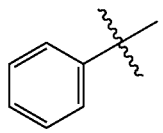 | 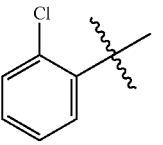 | $C_{27}H_{32}N_2O$<br>ES 401.1 (46),<br>195.1 (100) |
| 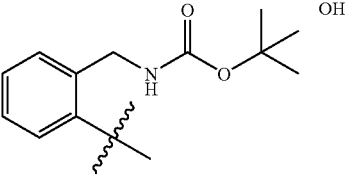 | OH | 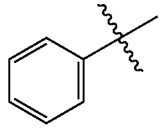 | 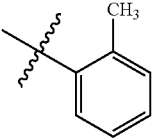 | $C_{31}H_{38}N_2O_3$<br>ES 487 (100) |
| 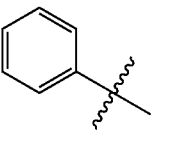 | 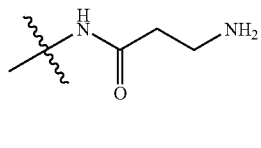 | 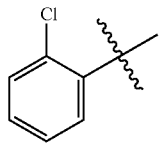 | 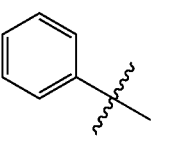 | $C_{27}H_{29}Cl_2N_3O$<br>ESI 484.2 (72),<br>482.2 (100), 237<br>(60), 235.0 (65) |
| 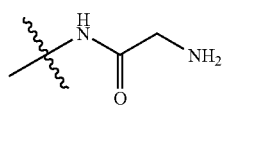 | 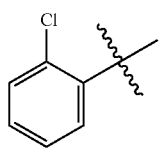 | 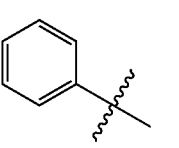 | 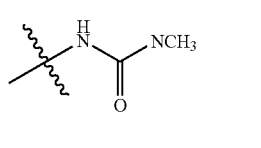 | $C_{26}H_{27}Cl_2N_3O$<br>ESI 470.1 (80),<br>468.1 (100), 235<br>(78) |
| 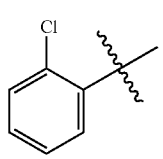 | 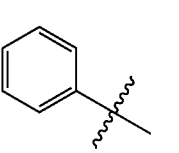 | 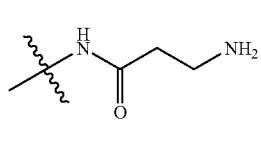 | 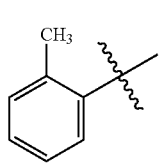 | $C_{26}H_{27}Cl_2N_3O$<br>ESI 470.2 (78),<br>468.2 (90), 237.0<br>(65), 235 (100) |
|  |  |  |  | $C_{29}H_{35}N_3O$<br>ESI 442.3 (100) |

TABLE 4-continued

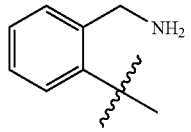

wherein $X^1$, $X^2$, $Z^1$ and $Z^2$ are as defined below

| $X^1$ | $X^2$ | $Z^1$ | $Z^2$ | Physical Data |
|---|---|---|---|---|
| 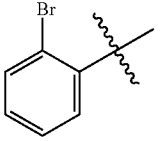 | OH | 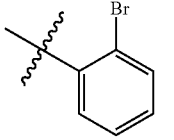 | 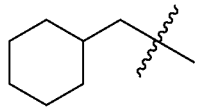 | $C_{25}H_{26}N_2OBr_2$ ESI 533 (55), 531 (100) 324.8 (30) |

TABLE 5

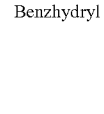

wherein $R^{11}$, $Z^1$ and $Z^2$ are as defined in the following table, wherein Ac is acetyl, Me is methyl and Et is ethyl::

| $R^{11}$ | $CH(Z^1)(Z^2)$ | Physical Data |
|---|---|---|
| H | Benzhydryl | |
| 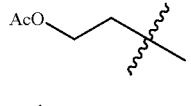 | Benzhydryl | $C_{32}H_{37}N_3O$:HCl Cl 480 (100), 167.25 (22) |
| 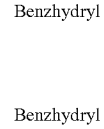 | Benzhydryl | $C_{29}H_{31}N_3O_3$:HCl Cl 470.15 (100), 167.25 (25) |
| 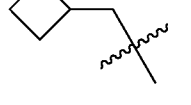 | Benzhydryl | $C_{29}H_{31}N_3O$:HCl Cl 438.20 (100), 167.25 (29) |
|  | Benzhydryl | $C_{30}H_{33}N_3O$:HCl FAB 452.3 (100), 167.0 (92) |
| 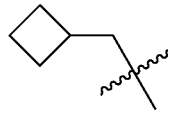 | Benzhydryl | $C_{29}H_{33}N_3O$:HCl Cl 440.20 (100), 167.25 (22) |
| Me | Benzhydryl | $C_{26}H_{27}N_3O$:HCl Cl 398.15 (100), 167.25 (39) |
| Ethyl | Benzhydryl | $C_{27}H_{29}N_3O$:HCl Cl 412.15 (100), 167.25 (32) |
| n propyl | Benzhydryl | $C_{28}H_{31}N_3O$:HCl ESI 426.1 (14), 167 (100) |
| n butyl | Benzhydryl | $C_{29}H_{33}N_3O$:HCl ESI 440.10 (100), 167.10 (33) |
| isopropyl | Benzhydryl | $C_{28}H_{31}N_3O$:HCl ESI 446.10 (28), 167. (100) |

TABLE 5-continued

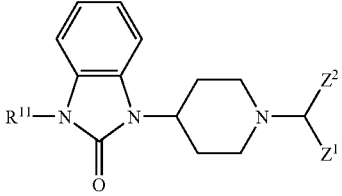

wherein R¹¹, Z¹ and Z² are as defined in the following table, wherein Ac is acetyl, Me is methyl and Et is ethyl::

| R¹¹ | CH(Z¹)(Z²) | Physical Data |
|---|---|---|
| 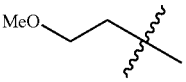 MeO | Benzhydryl | $C_{28}H_{31}N_3O_2$:HCl<br>ESI 442.10 (15), 167. (100) |
| 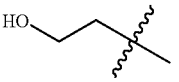 HO | Benzhydryl | $C_{27}H_{29}N_3O_2$:HCl<br>FAB 428.3 (65), 232.1 (57) |
| H | 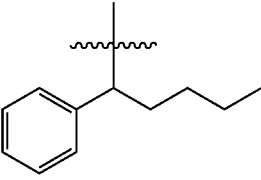 | $C_{23}H_{29}N_3O$:HCl<br>ESI 364.1 (58), 218.1 (100) |
| 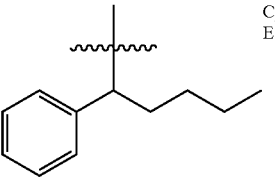 HO | 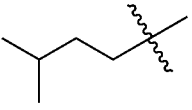 | $C_{25}H_{33}N_3O_2$:HCl<br>ESI 408.1 (93), 262.1 (100) |
| n pentyl | Benzhydryl | $C_{30}H_{35}N_3O$:Hcl<br>ESI 454.1 (46), 167.1 (100) |
| n-hexyl | Benzhydryl | $C_{31}H_{37}N_3O$:HCl<br>ESI 468.1 (26), 167 (100) |
| 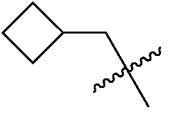 | Benzhydryl | $C_{28}H_{31}N_3O_2$:HCl<br>ESI 442.10 (15), 167 (100) |
| 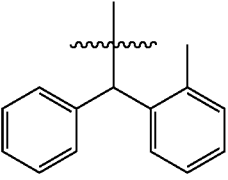 | 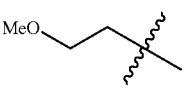 | $C_{31}H_{35}N_3O$: HCl<br>ESI 466.1 (44), 181.1 (100) |
| 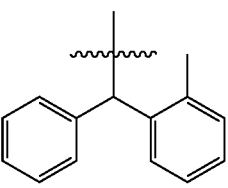 MeO | 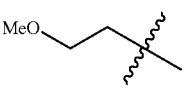 | $C_{29}H_{33}N_3O_2$:HCl<br>ESI 456.1 (48), 181.10 (100) |

TABLE 5-continued
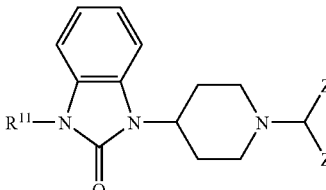
wherein R[11], Z[1] and Z[2] are as defined in the following table, wherein Ac is acetyl, Me is methyl and Et is ethyl::
| R[11] | CH(Z[1])(Z[2]) | Physical Data |
|---|---|---|
| H |  | $C_{24}H_{31}N_3O$:HCl<br>Cl 378.25 (100), 306.20 (22), 218.20 (24) |
| H | 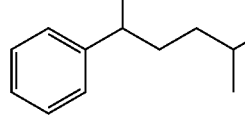 | $C_{26}H_{27}N_3O$:HCl<br>ESI 398.10 (44), 181.1 (100) |
|  | 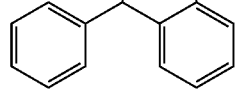 | $C_{27}H_{33}N_3O$:HCl<br>ESI 416.10 (36), 286.1 (39) |
| 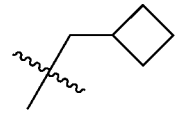 |  | $C_{30}H_{31}N_3OCl_2$:HCl<br>ESI 522.1 (79), 521.1 (48), 520 (100) |
| 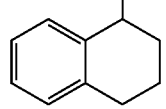 | Benzhydryl | $C_{30}H_{34}N_2O$:HCl<br>Cl 439.25 (100), 168.30 (20) |
| H |  | $C_{27}H_{29}N_3O$:HCl<br>Cl 412.20 (32), 218.20 (42), 195.35 (100) |
| 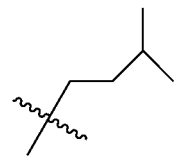 | Benzhydryl | $C_{29}H_{31}N_3O_3$:HCl<br>ESI 470.1 (100), 167.1 (77.40) |

TABLE 5-continued
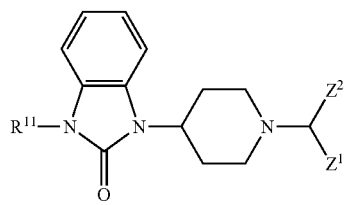
wherein R[11], Z[1] and Z[2] are as defined in the following table, wherein Ac is acetyl, Me is methyl and Et is ethyl::
| R[11] | CH(Z[1])(Z[2]) | Physical Data |
|---|---|---|
| H | 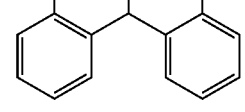 | $C_{25}H_{23}N_3Cl_2O$:HCl<br>ESI 452.1 (100), 235 (85) |
|  | 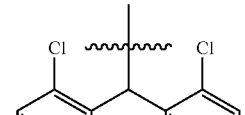 | $C_{30}H_{33}N_3O_2Cl_2$:HCl<br>ESI 525.1 (39), 524.1 (82), 522 (100) |
| 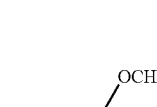 | 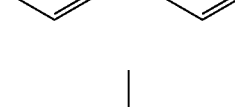 | $C_{28}H_{29}N_3OCl_2$:HCl<br>ESI 511.1 (46), 510 (100), 514 (20),<br>513.1 (33.50) |
|  | 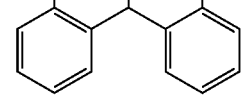 | $C_{32}H_{39}N_3O$:HCl<br>ESI 482.1 (48), 195.1 (100) |
|  | 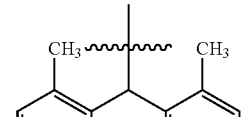 | $C_{30}H_{35}N_3O_2$:HCl<br>ESI 471.1 (13), 470.1 (30), 195.1 (100) |
| H | 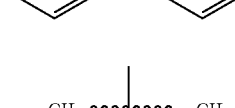 | $C_{25}H_{24}N_3OCl$:HCl<br>FAB 420.2 (35), 418.2 (100),<br>201.0<br>(75) |

TABLE 5-continued

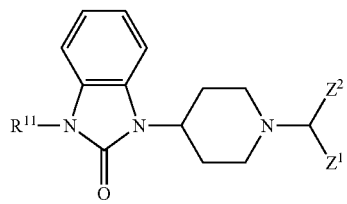

wherein R$^{11}$, Z$^1$ and Z$^2$ are as defined in the following table, wherein Ac is acetyl, Me is methyl and Et is ethyl::

| R$^{11}$ | CH(Z$^1$)(Z$^2$) | Physical Data |
|---|---|---|
| H | ![structure: CH(phenyl)(2-fluorophenyl)] | C$_{25}$H$_{24}$N$_3$OF:HCl<br>Elemental Analysis C: 68.12; H: 5.83;<br>N: 9.48; Cl: 8.21; F;: 4.59 |
| ![CH2CH2NHMe] | Benzhydryl | C$_{28}$H$_{32}$N$_4$O:HCl<br>ESI 442.1 (39), 441.1 (92), 167 (100) |
| ![CH2CH2NHEt] | Benzhydryl | C$_{29}$H$_{34}$N$_4$O:HCl<br>ESI 455.1 (100), 290.1 (14), 289.1<br>(57.88), 167 (94) |
| ![CH2CH2NH2] | Benzhydryl | C$_{27}$H$_{30}$N$_4$O:HCl<br>ESI 428.1 (42), 427.1 (97), 167 (100) |
| ![CH2CH2NHiPr] | Benzhydryl | C$_{30}$H$_{36}$N$_4$O.HCl<br>ESI 470.1 (48), 469 (100), 303 (93),<br>167 (82.75) |
| ![CH2CH2NMe2] | Benzhydryl | C$_{29}$H$_{34}$N$_4$O:HCl<br>ESI 457.1 (13), 456 (57), 455.1 (100),<br>167 (72) |
| ![CH2C(O)OMe] | Benzhydryl | C$_{28}$H$_{29}$N$_3$O$_3$<br>FAB 456.2 (78), 167.0 (100) |
| ![CH2C(O)OMe] | ![CH(2,6-dichlorophenyl)] | C$_{22}$H$_{23}$Cl$_2$N$_3$O$_3$<br>FAB 450.1 (27), 448.0 (100) |
| H | ![CH(2-methylphenyl)(propyl)] | C$_{24}$H$_{31}$N$_3$O<br>FAB 378.4 (100), 218.2 (30) |
| ![CH2CH2CH2C(O)OEt] | Benzhydryl | C$_{31}$H$_{35}$N$_3$O$_3$<br>498.2 (100), 167.1 (90) |

TABLE 5-continued
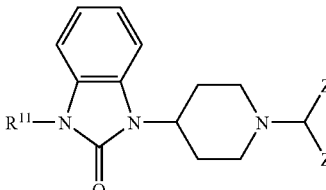
wherein R[11], Z[1] and Z[2] are as defined in the following table, wherein Ac is acetyl, Me is methyl and Et is ethyl::
| R[11] | CH(Z[1])(Z[2]) | Physical Data |
|---|---|---|
|  | Benzhydryl | $C_{29}H_{31}N_3O_3$<br>ESI 470.1 (100), 167.1 (55) |
|  | 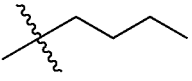 | $C_{23}H_{27}Cl_2N_3O$<br>ESI 434.1 (80), 432.1 (100) |
| 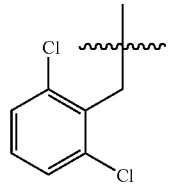 | 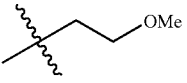 | $C_{22}H_{25}Cl_2N_3O_2$<br>ESI 436.1 (58), 434.1 (100) |
| 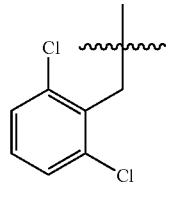 |  | $C_{23}H_{27}Cl_2N_3O$<br>ESI 434.1 (35), 432.1 (100) |
| 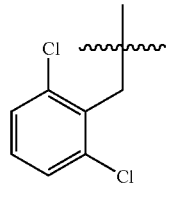 | 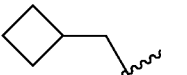 | $C_{24}H_{27}Cl_2N_3O$<br>ESI 446.1 (77)), 444.1 (100) |
| 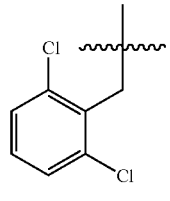 | 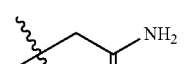 | $C_{21}H_{22}Cl_2N_4O_2$<br>FAB 435.1 (78), 433.1 (100) |

TABLE 6

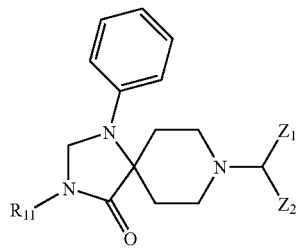

wherein $R^{11}$, $Z^1$ and $Z^2$ are as defined in the following table:

| $R^{11}$ | $CH(Z^1)(Z^2)$ | Physical Data |
|---|---|---|
| H | Benzhydryl | |
| isopropyl (shown as structure) | Benzhydryl | $C_{29}H_{33}N_3O$<br>ESI: 440 (100) 167 (80) |
| allyl (shown as structure) | Benzhydryl | $C_{29}H_{31}N_3O$<br>ESI: 438 (100) 167 (99) |
| n-pentyl (shown as structure) | Benzhydryl | $C_{30}H_{35}N_3O$<br>ESI: 454 (100) 167 (94) |
| propargyl (shown as structure) | Benzhydryl | $C_{29}H_{29}N_3O$<br>ESI: 436 (99) 167 (100) |
| $CH_3$ | Benzhydryl | $C_{27}H_{29}N_3O$<br>FAB: 412 (100) |
| sec-butyl (shown as structure) | Benzhydryl | $C_{28}H_{31}N_3O$<br>FAB: 426 (100) |
| $CH_2C(O)OEt$ (shown as structure) | Benzhydryl | $C_{30}H_{33}N_3O_3$<br>FAB: 484 (7) 261 (14) 167 (100) |
| cyclopropylmethyl (shown as structure) | Benzhydryl | $C_{30}H_{33}N_3O$<br>ESI: 452 (100) 167 (60) |
| cyclohexylmethyl (shown as structure) | Benzhydryl | $C_{33}H_{39}N_3O$<br>ESI: 494 (100) 167 (30) |
| cyclobutylmethyl (shown as structure) | Benzhydryl | $C_{31}H_{35}N_3O \cdot HCl$<br>FAB: 466 (100) |
| $CH_2CH_2C(O)OCH_3$ (shown as structure) | Benzhydryl | $C_{30}H_{33}N_3O_3 \cdot HCl$<br>FAB: 484 (100 167 41 |

TABLE 6-continued

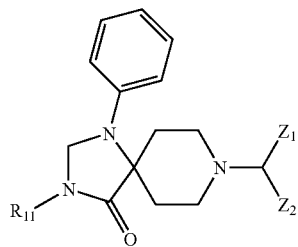

wherein $R^{11}$, $Z^1$ and $Z^2$ are as defined in the following table:

| $R^{11}$ | $CH(Z^1)(Z^2)$ | Physical Data |
|---|---|---|
| cyclohexyl-NH-C(O)-C(CH3)- | Benzhydryl | $C_{33}H_{38}N_4O_2$ . HCl<br>FAB: 523 (100) |
| H | 1-(bis(4-fluorophenyl))ethyl | $C_{26}H_{25}N_3F_2$ . HCl<br>ESI: 434 (29) 203 (100) |
| H | 1-(bis(3-fluorophenyl))ethyl | $C_{26}H_{25}N_3F_2O$ . HCl<br>CI: 434 (100) |
| H | 1-(4-chlorophenyl)(phenyl)ethyl | $C_{26}H_{26}N_3ClO$ . HCl<br>ESI: 432 (60) 201 (100) |
| n-butyl | Benzhydryl | $C_{29}H_{33}N_3O$ . HCl<br>ESI: 440 (100) 167 (89) |
| cyclohexyl-C(O)-C(CH3)- | Benzhydryl | $C_{33}H_{37}N_3O_2$ . HCl<br>ESI: 508 (100) 167 (35) |
| H | 1-(4-chlorophenyl)pentyl | $C_{24}H_{30}N_3ClO$ . HCl<br>ESI: 412 (100) 232 (92) |

TABLE 6-continued
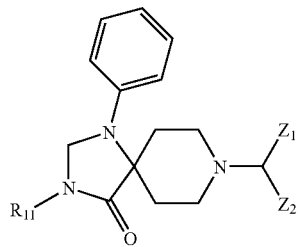
wherein $R^{11}$, $Z^1$ and $Z^2$ are as defined in the following table:
| $R^{11}$ | $CH(Z^1)(Z^2)$ | Physical Data |
|---|---|---|
| H | ![butyl-phenyl] | $C_{24}H_{31}N_3O$. HCl<br>ESI: 378 (100) 232 (82) |
| H | ![2-chlorophenyl ethyl] | $C_{21}H_{24}N_3ClO$. HCl<br>ESI: 370 (86) 265 (100) |
| H | ![butyl-4-fluorophenyl] | $C_{24}H_{30}N_3FO$. HCl<br>ESI: 396 (31) 232 (100) |
| H | ![butyl-4-bromophenyl] | $C_{24}H_{30}N_3BrO$. HCl<br>ESI: 456 (39) 232 (100) |
| H | ![isobutyl-phenyl] | $C_{25}H_{33}N_3O$. HCl<br>ESI: 392 (73) 232 (100) |
| H | ![phenyl-cyclopentyl] | $C_{25}H_{31}N_3O$. HCl<br>FAB: 390 (100) |

TABLE 6-continued

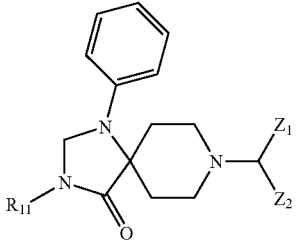

wherein $R^{11}$, $Z^1$ and $Z^2$ are as defined in the following table:

| $R^{11}$ | $CH(Z^1)(Z^2)$ | Physical Data |
|---|---|---|
| *n-pentyl* | 1-phenylpentyl | $C_{28}H_{39}N_3O \cdot HCl$<br>ESI: 434 (68) 288 (100) |
| cyclohexylmethyl | 1-phenylpentyl | $C_{31}H_{43}N_3O \cdot HCl$<br>ESI: 474 (90) 328 (100) |
| isobutyl | 1-phenylpentyl | $C_{27}H_{37}N_3O \cdot HCl$<br>ESI: 420 (81) 274 (100) |
| H | phenyl(2-methylphenyl)methyl | $C_{27}H_{29}N_3O \cdot HCl$<br>FAB: 412 (25) 181 (100) |
| *n-pentyl* | 5-methyl-1-phenylhexyl | $C_{29}H_{41}N_3O \cdot HCl$<br>ESI: 448 (97) 288 (100) |
| *n-butyl* | 1-phenylpentyl | $C_{27}H_{37}N_3O \cdot HCl$<br>ESI: 420 (62) 274 (100) |

TABLE 6-continued

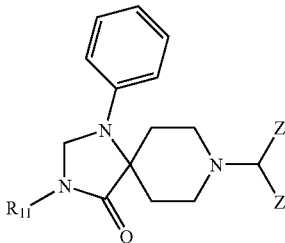

wherein $R^{11}$, $Z^1$ and $Z^2$ are as defined in the following table:

| $R^{11}$ | $CH(Z^1)(Z^2)$ | Physical Data |
|---|---|---|
| isobutyl | 4-methyl-1-phenylpentyl | $C_{28}H_{39}N_3O \cdot HCl$<br>ESI: 434 (66) 274 (100) |
| H | 1-(2-methylphenyl)pentyl | $C_{25}H_{33}N_3O \cdot HCl$<br>ESI: 392 (59) 232 (100) |
| benzyl | 1-phenylpentyl | $C_{31}H_{37}N_3O \cdot HCl$<br>ESI: 468 (100) 322 (92) |
| sec-butyl | 4-methyl-1-phenylpentyl | $C_{28}H_{39}N_3O \cdot HCl$<br>ESI: 434 (100) 274 (86) |
| H | methyl 2-phenyl-2-(...)acetate | $C_{22}H_{25}N_3O_3 \cdot HCl$<br>Cl: 380 (100) |
| benzyl | 4-methyl-1-phenylpentyl | $C_{32}H_{39}N_3O \cdot HCl$<br>ESI: 482 (100) 322 (78) |

TABLE 6-continued

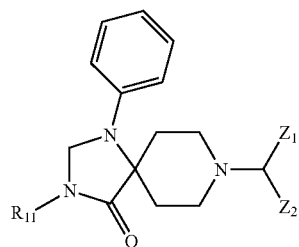

wherein $R^{11}$, $Z^1$ and $Z^2$ are as defined in the following table:

| $R^{11}$ | $CH(Z^1)(Z^2)$ | Physical Data |
|---|---|---|
| H | (2-hydroxy-1-phenylethyl group, wavy bond at CH) | $C_{21}H_{25}N_3O_2 \cdot HCl$<br>FAB: 352 (100) |
| 2-methylbenzyl (gem-dimethyl) | (4-methyl-1-phenylpentyl group) | $C_{33}H_{41}N_3O \cdot HCl$<br>FAB: 496 (100) |
| H | bis(2-methylphenyl)methyl | $C_{28}H_{31}N_3O \cdot HCl$<br>ESI: 426 (19) 195 (100) |
| H | bis(2-chlorophenyl)methyl | $C_{26}H_{26}N_3Cl_2O \cdot HCl$<br>ESI: 466 (79) 235 (100) |
| H | 2-morpholino-1-phenylethyl | $C_{25}H_{32}N_4O_2 \cdot HCl$<br>ESI: 421 (40) 190 (100) |
| H | (2-fluorophenyl)(phenyl)methyl | $C_{26}H_{26}N_3FO \cdot HCl$<br>FAB: 416 (100) |

TABLE 6-continued

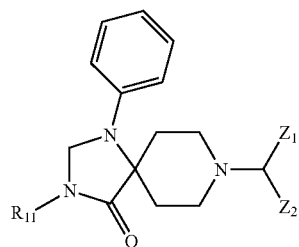

wherein $R^{11}$, $Z^1$ and $Z^2$ are as defined in the following table:

| $R^{11}$ | $CH(Z^1)(Z^2)$ | Physical Data |
|---|---|---|
| H | 3-Cl-C₆H₄, 3-Cl-C₆H₄ | $C_{26}H_{25}N_3Cl_2O \cdot HCl$<br>ESI: 466 (100) 235 (60) |
| H | C₆H₅, 2-Cl-C₆H₄ | $C_{26}H_{26}N_3ClO \cdot HCl$<br>ESI: 432 (48) 201 (100) |
| H | 2-F-C₆H₄, 2-F-C₆H₄ | $C_{26}H_{26}N_3F_2O \cdot HCl$<br>ESI: 434 (69) 203 (100) |
| cyclohexylmethyl | indanyl | $C_{29}H_{37}N_3O \cdot HCl$<br>ESI: 444 (52) 326 (100) |
| cyclobutylmethyl | indanyl | $C_{27}H_{33}N_3O \cdot HCl$<br>ESI: 416 (33) 300 (100) |
| 3-hydroxy-2,2-dimethylpropyl | 2-Cl-C₆H₄, 2-Cl-C₆H₄ | $C_{28}H_{29}N_3Cl_2O_2 \cdot HCl$<br>ESI: 510 (100) |

TABLE 6-continued
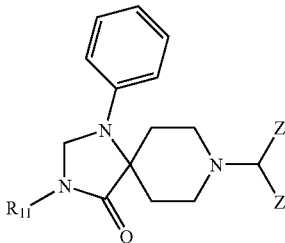
wherein R[11], Z[1] and Z[2] are as defined in the following table:
| R[11] | CH(Z[1])(Z[2]) | Physical Data |
|---|---|---|
| 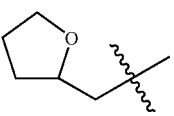 | 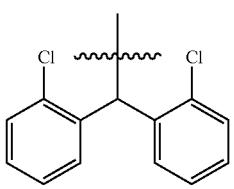 | $C_{31}H_{33}N_3Cl_2O_2$ · HCl<br>ESI: 550 (100) |
| 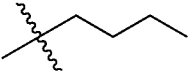 | 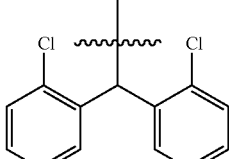 | $C_{30}H_{33}N_3Cl_2O$ · HCl<br>ESI: 522 (100) |
| 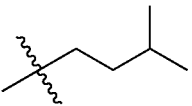 | 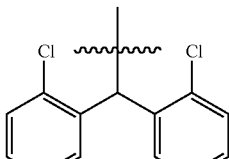 | $C_{31}H_{35}N_3Cl_2O$ · HCl<br>ESI: 536 (100) |
| 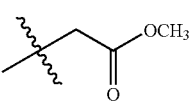 | 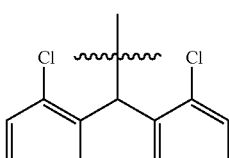 | $C_{29}H_{29}N_3Cl_2O_3$ · HCl<br>FAB: 538 (100) |
| 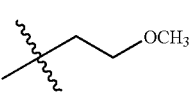 | 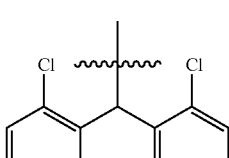 | $C_{29}H_{31}N_3Cl_2O_2$ · HCl<br>ESI: 524 (100) |
| 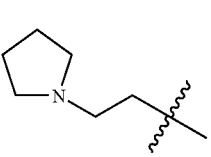 | 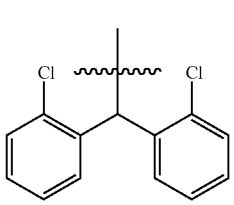 | $C_{32}H_{36}N_4Cl_2O$ · HCl<br>FAB: 563 (100) 235 (55) |

TABLE 6-continued

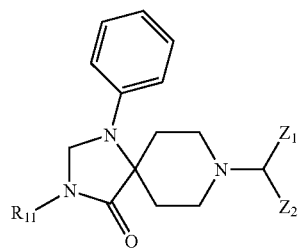

wherein $R^{11}$, $Z^1$ and $Z^2$ are as defined in the following table:

| $R^{11}$ | $CH(Z^1)(Z^2)$ | Physical Data |
|---|---|---|
| n-butyl | bis(2-chlorophenyl)methyl | $C_{27}H_{37}N_3O_2 \cdot HCl$<br>FAB: 436 (100) |
| CH₂CH₂OCH₃ | 2-phenyl-3-hydroxypropyl | $C_{24}H_{31}N_3O_3 \cdot HCl$<br>FAB: 410 (100) |
| isobutyl | 2-phenyl-3-hydroxypropyl | $C_{25}H_{33}N_3O_2 \cdot HCl$<br>FAB: 408 (100) |
| isopentyl | 2-phenyl-3-hydroxypropyl | $C_{26}H_{35}N_3O_2 \cdot HCl$<br>FAB: 422 (100) |
| CH₂CH₂NHMe | bis(2-chlorophenyl)methyl | $C_{29}H_{32}N_4Cl_2O \cdot 2HCl$<br>FAB: 523 (100) |
| CH₂CH₂NH-iPr | bis(2-chlorophenyl)methyl | $C_{31}H_{36}N_4Cl_2O \cdot 2HCl$<br>FAB: 551 (100) |

TABLE 6-continued

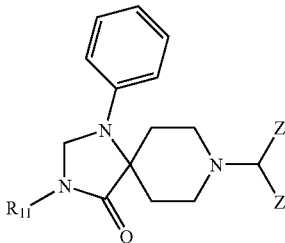

wherein $R^{11}$, $Z^1$ and $Z^2$ are as defined in the following table:

| $R^{11}$ | $CH(Z^1)(Z^2)$ | Physical Data |
|---|---|---|
| ethylaminoethyl | bis(2-chlorophenyl)methyl | $C_{30}H_{34}N_4Cl_2O \cdot 2HCl$<br>FAB: 537 (100) |
| (N-methyl-N-ethyl)aminoethyl | bis(2-chlorophenyl)methyl | $C_{30}H_{34}N_4Cl_2O \cdot 2HCl$<br>FAB: 537 (100) |
| pyrrolidinylethyl | 1,2,3,4-tetrahydronaphthalen-1-yl | $C_{29}H_{38}N_4O \cdot 2HCl$<br>FAB: 459 (100) |
| pyrrolidinylpropyl | bis(2-chlorophenyl)methyl | $C_{33}H_{38}N_4Cl_2O \cdot 2HCl$<br>ESI: 577 (56) 343 (100) |
| piperidinylethyl | bis(2-chlorophenyl)methyl | $C_{33}H_{38}Cl_2N_4O$<br>ESI 577 (100), 343 (45) |
| cyclopentylaminoethyl | bis(2-chlorophenyl)methyl | $C_{33}H_{38}Cl_2N_4O$<br>ESI 577 (100), 343 (45) |

TABLE 6-continued

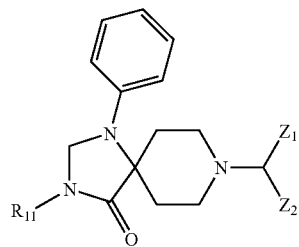

wherein $R^{11}$, $Z^1$ and $Z^2$ are as defined in the following table:

| $R^{11}$ | $CH(Z^1)(Z^2)$ | Physical Data |
|---|---|---|
| ~~~-CH2CH2CH2-NH-cyclohexyl | bis(2-chlorophenyl)methyl | $C_{34}H_{40}Cl_2N_4O$<br>ESI 487 (100), 327 (51) |
| ~~~-CH2CH2CH2-pyrrolidinyl | 1-phenyl-3-methylbutyl | $C_{31}H_{44}N_4O$<br>ESI 487 (100), 327 (51) |
| ~~~-CH2CH2CH2-(4-methylpiperazinyl) | bis(2-chlorophenyl)methyl | $C_{33}H_{39}Cl_2N_5O$<br>ESI 592 (100), 358 (71), 235 (64) |
| ~~~-CH2CH2CH2-NH-cyclopropyl | bis(2-chlorophenyl)methyl | $C_{31}H_{34}Cl_2N_4O$<br>ESI 549 (100), 315 (52) |
| ~~~-CH2CH2CH2-pyrrolidinyl | 4,4-dimethyl-1,2,3,4-tetrahydronaphthalen-1-yl | $C_{31}H_{42}N_4O$<br>ESI 487 (100), 329 (85) |
| ~~~-CH2CH2CH2-NH-isobutyl | 4,4-dimethyl-1,2,3,4-tetrahydronaphthalen-1-yl | $C_{31}H_{44}N_4O$<br>ESI 487 (100), 331 (99) |

TABLE 6-continued
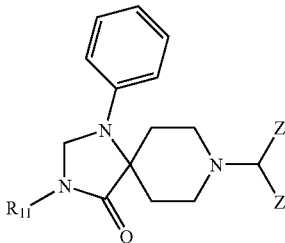
wherein $R^{11}$, $Z^1$ and $Z^2$ are as defined in the following table:
| $R^{11}$ | $CH(Z^1)(Z^2)$ | Physical Data |
|---|---|---|
| 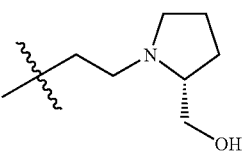 | 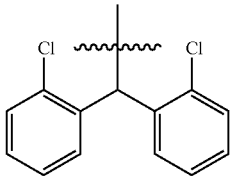 | $C_{33}H_{38}Cl_2N_4O_2$<br>ESI 593 (100), 359 (45), 297 (45) |
| 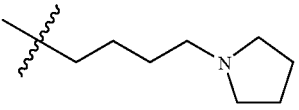 | 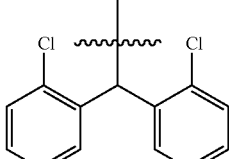 | $C_{34}H_{40}Cl_2N_4O$<br>ESI 591 (100), 357 (82), 235 (99) |
| 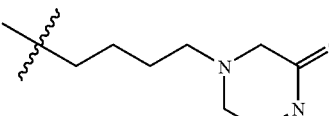 | 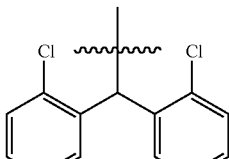 | $C_{34}H_{39}Cl_2N_5O_2$<br>ESI 620 (100), 386 (12), 235 (28) |
| 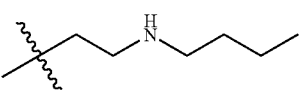 | 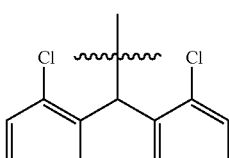 | $C_{32}H_{38}Cl_2N_4O$<br>ESI 565 (100), 331 (56), 235 (52) |
| 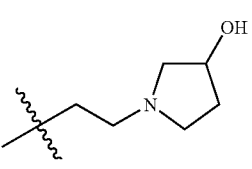 | 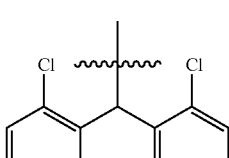 | $C_{32}H_{36}Cl_2N_4O_2$<br>ESI 579 (100), 345 (51), 235 (76) |
| 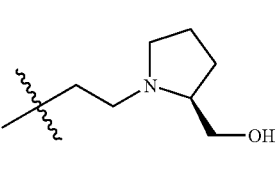 | 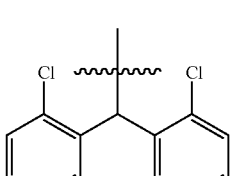 | $C_{33}H_{38}Cl_2N_4O_2$<br>ESI 593 (100), 359 (63), 235 (90) |

TABLE 6-continued
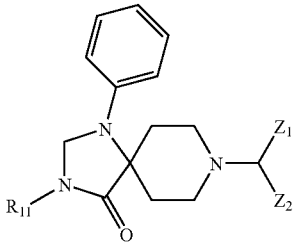
wherein $R^{11}$, $Z^1$ and $Z^2$ are as defined in the following table:
| $R^{11}$ | $CH(Z^1)(Z^2)$ | Physical Data |
|---|---|---|
| 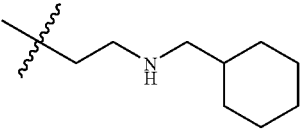 | 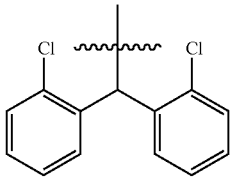 | $C_{35}H_{42}Cl_2N_4O$<br>ESI 605 (100), 371 (83) |
| 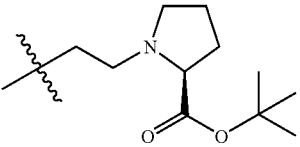 | 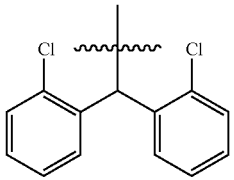 | $C_{37}H_{44}Cl_2N_4O_3$<br>FAB 663 (100), 234 (42) |
| 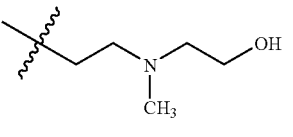 | 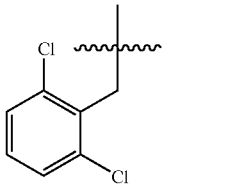 | $C_{25}H_{32}Cl_2N_4O_2$<br>ESI 491 (100), 333 (29) |
| 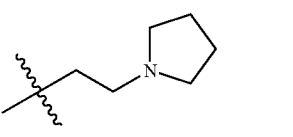 | 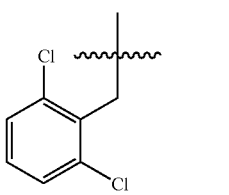 | $C_{26}H_{32}Cl_2N_4O$<br>ESI 487 (100), 319 (31) |
| 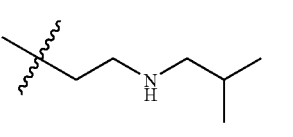 | 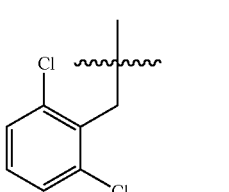 | $C_{26}H_{34}Cl_2N_4O$<br>ESI 489 (100), 331 (18) |
| 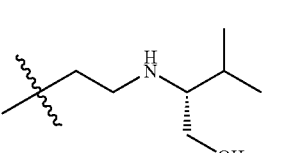 | 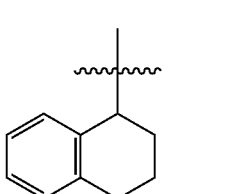 | $C_{32}H_{46}N_4O_2$<br>ESI 519 (91), 361 (100) |

TABLE 6-continued

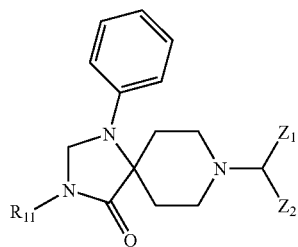

wherein $R^{11}$, $Z^1$ and $Z^2$ are as defined in the following table:

| $R^{11}$ | $CH(Z^1)(Z^2)$ | Physical Data |
|---|---|---|
| propylaminopropyl | 2,6-dichlorobenzyl | $C_{25}H_{32}N_4Cl_2O$<br>ESI 475 (100), 317 (24), 159 (69) |
| methylaminopropyl | 4,4-dimethyltetrahydronaphthalen-1-yl | $C_{28}H_{38}N_4O$<br>FAB 447.3 (100), 289.2 (25), 242.2 (36) |
| ethylaminopropyl | 4,4-dimethyltetrahydronaphthalen-1-yl | $C_{29}H_{40}N_4O$<br>FAB 461.2 (100), 303.2 (20) |
| morpholinopropyl | 4,4-dimethyltetrahydronaphthalen-1-yl | $C_{31}H_{42}N_4O_2$<br>ESI 503.1 (100), 345.1 (95) |
| isopropylaminopropyl | 4,4-dimethyltetrahydronaphthalen-1-yl | $C_{30}H_{42}N_4O$<br>ESI 475.1 (99), 317.1 (100) |

TABLE 6-continued
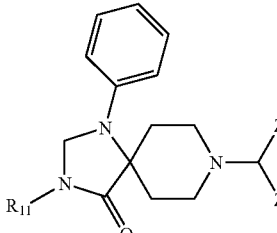
wherein R[11], Z[1] and Z[2] are as defined in the following table:
| R[11] | CH(Z[1])(Z[2]) | Physical Data |
|---|---|---|
| 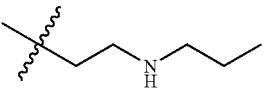 | 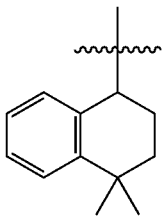 | $C_{30}H_{42}N_4O$<br>ESI 475.1 (89), 317.1 (100) |
| 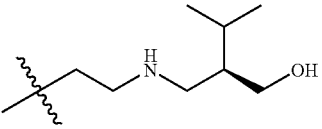 | 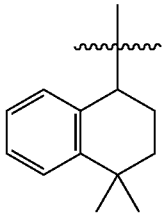 | $C_{33}H_{48}N_4O_2$<br>ESI 519.1 (95), 361.1 (100) 256.1 (12) |
| 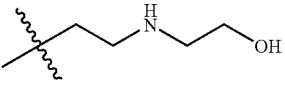 | 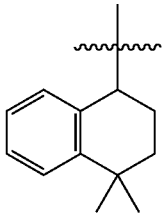 | $C_{29}H_{40}N_4O_2$<br>ESI 477.1 (100), 319.1 (100) |
| 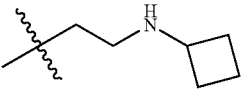 | 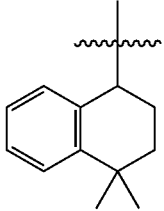 | $C_{31}H_{42}N_4O$<br>ESI 487.10 (100), 329.1 (88) |
| 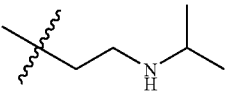 | 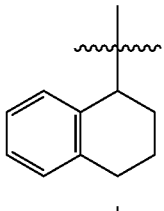 | $C_{28}H_{38}N_4O$<br>FAB 447 (100), 391 (30), 317 (20) |
| 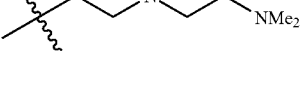 | 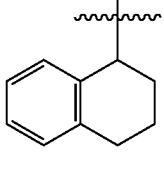 | $C_{29}H_{41}N_5O$<br>FAB 476 (100), 346 (40) |

TABLE 6-continued
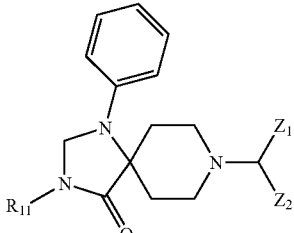
wherein R¹¹, Z¹ and Z² are as defined in the following table:
| R¹¹ | CH(Z¹)(Z²) | Physical Data |
|---|---|---|
| 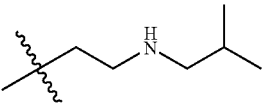 | 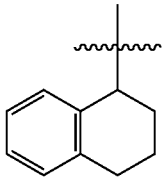 | $C_{29}H_{40}N_4O$<br>FAB 461 (100), 391 (40), 167 (22) |
| 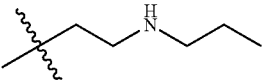 | 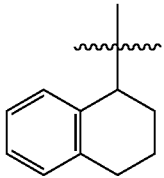 | $C_{28}H_{38}N_4O$<br>FAB 447 (100), 391 (60) |
| 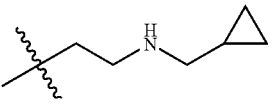 | 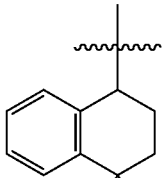 | $C_{31}H_{42}N_4O$<br>ESI 487.1 (100), 329.1 (86) |
| 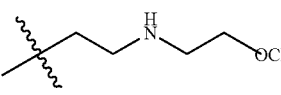 | 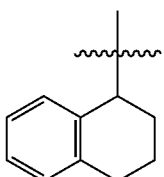 | $C_{30}H_{42}N_4O_2$<br>ESI 491.1 (63), 333.10 (100) |
|  | 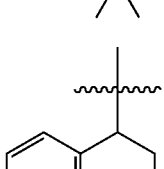 | $C_{34}H_{48}N_4O$<br>ESI 529.1 (79), 371.1 (100) |
|  | 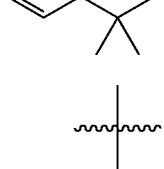 | $C_{31}H_{45}N_5O$<br>ESI 504.1 (99), 358.1 (100) |

TABLE 6-continued

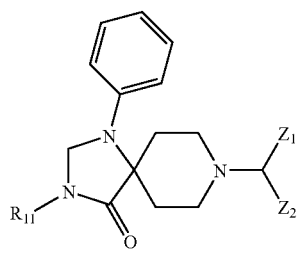

wherein $R^{11}$, $Z^1$ and $Z^2$ are as defined in the following table:

| $R^{11}$ | $CH(Z^1)(Z^2)$ | Physical Data |
|---|---|---|
| piperazinylpropyl (N-methyl) | 1,1-dimethyl-tetrahydronaphthalenyl | $C_{32}H_{45}N_5O$<br>ESI 516.1 (92), 358.1 (100), 251.1 (28) |
| isopropylaminopropyl | 2,6-dichlorobenzyl | $C_{25}H_{32}Cl_2N_4O$<br>ESI 475 (100), 317 (16) |
| ethylaminopropyl | 2,6-dichlorobenzyl | $C_{24}H_{30}Cl_2N_4O$<br>ESI 461 (100), 303 (25) |
| methylaminopropyl | 2,6-dichlorobenzyl | $C_{23}H_{28}Cl_2N_4O$<br>ESI 447 (100), 224 (64) |
| diethylaminopropyl | 2,6-dichlorobenzyl | $C_{26}H_{34}Cl_2N_4O$<br>ESI 489 (100), 331 (33) |
| 2,6-difluorobenzyl | 2,6-difluorobenzyl | $C_{27}H_{25}F_4N_3O$<br>ESI 484 (100) |

TABLE 6-continued wherein R$^{11}$, Z$^1$ and Z$^2$ are as defined in the following table:

| R$^{11}$ | CH(Z$^1$)(Z$^2$) | Physical Data |
|---|---|---|
| ~~~N(H)–CH$_2$–cyclopropyl (propyl linker) | 2,6-dichlorobenzyl | C$_{26}$H$_{32}$Cl$_2$N$_4$O<br>ESI 487 (100), 433 (39) |
| ~~~N(H)–cyclobutyl (propyl linker) | 2,6-dichlorobenzyl | C$_{26}$H$_{32}$Cl$_2$N$_4$O<br>ESI 487 (100), 433 (46) |
| ~~~N(H)–n-butyl (propyl linker) | 4,4-dimethyltetrahydronaphthalen-1-yl | C$_{31}$H$_{44}$N$_4$O<br>ESI 489.1 (100), 331.1 (68) |
| ~~~N(H)–allyl (propyl linker) | 4,4-dimethyltetrahydronaphthalen-1-yl | C$_{30}$H$_{40}$N$_4$O<br>ESI 473.1 (100), 315.1 (55) |
| ~~~N(H)–isobutyl (propyl linker) | 4,4-dimethyltetrahydronaphthalen-1-yl | C$_{32}$H$_{46}$N$_4$O<br>ESI 503.1 (100), 345.1 (834) |
| ~~~N(H)–cyclohexyl (propyl linker) | 4,4-dimethyltetrahydronaphthalen-1-yl | C$_{33}$H$_{46}$N$_4$O<br>ESI 515.1 (73), 357.1 (100), 258.1 (9) |

TABLE 6-continued

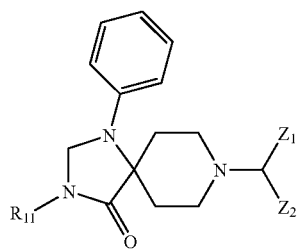

wherein $R^{11}$, $Z^1$ and $Z^2$ are as defined in the following table:

| $R^{11}$ | $CH(Z^1)(Z^2)$ | Physical Data |
|---|---|---|
| ![thiophene-methylamino-propyl] | ![1,1-dimethyl-tetrahydronaphthalen-4-yl] | $C_{32}H_{40}N_4OS$<br>ESI 433.1 (22), 371.1 (83) |
| ![cyclopentylamino-propyl] | ![1,1-dimethyl-tetrahydronaphthalen-4-yl] | $C_{32}H_{44}N_4O$<br>ESI 501.1 (80), 343.1 (100), 251.1 (7), 159.1 (69) |
| ![furan-methylamino-propyl] | ![1,1-dimethyl-tetrahydronaphthalen-4-yl] | $C_{32}H_{40}N_4O_2$<br>ESI 513.1 (87), 433.1 (32), 355.1 (100), 275.1 (12) |
| ![benzylamino-propyl] | ![1,1-dimethyl-tetrahydronaphthalen-4-yl] | $C_{34}H_{42}N_4O$<br>ESI 523.1 (91), 365.1 (100) |
| ![butylamino-propyl] | ![bis(2-chlorophenyl)methyl] | $C_{32}H_{38}Cl_2N_4O$<br>ESI 565 (100), 331 (56), 235 (52) |

TABLE 6-continued
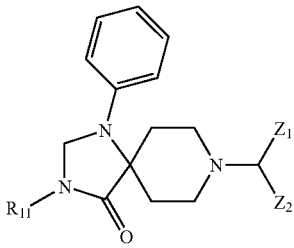
wherein $R^{11}$, $Z^1$ and $Z^2$ are as defined in the following table:
| $R^{11}$ | $CH(Z^1)(Z^2)$ | Physical Data |
|---|---|---|
| H | 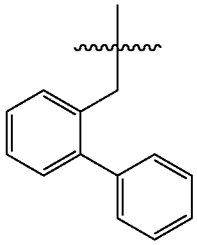 | $C_{26}H_{27}N_3O$<br>ESI 398 (100), 397 (4) |
| 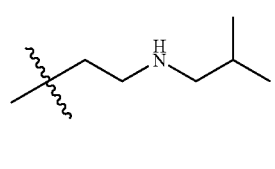 | 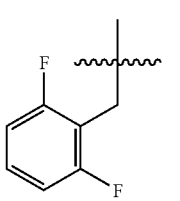 | $C_{26}H_{34}FN_4O$<br>ESI 457 (92), 229 (100) |
| 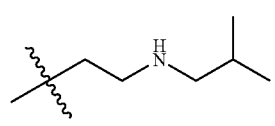 | 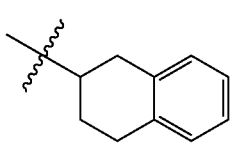 | $C_{29}H_{40}N_4O$<br>ESI 461 (99), 231 (100) |
| 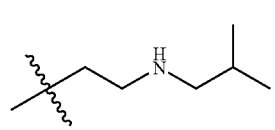 | 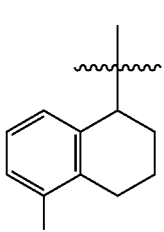 | $C_{30}H_{42}O_2$<br>ESI 491.1 (90), 331.1 (65), 61 (100) |
| 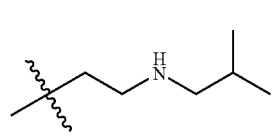 | 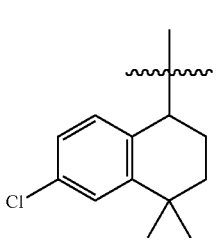 | $C_{31}H_{43}ClN_4O$<br>ESI 525.1 (42), 524.1 (53), 523.1 (65), 331.1 (60), 193.1 (100) |
| 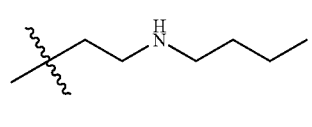 | 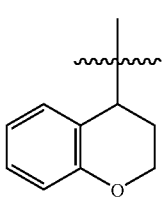 | $C_{28}H_{38}N_4O_2$<br>ESI 463 (100), 331 (38) |

TABLE 6-continued wherein R[11], Z[1] and Z[2] are as defined in the following table:

| R[11] | CH(Z[1])(Z[2]) | Physical Data |
|---|---|---|
| *n-butylaminoethyl* | 2-(ethoxycarbonyl)benzyl | $C_{29}H_{40}N_4O_3$<br>ESI 494 (100), 247 (95) |
| *n-butylaminoethyl* | 2,6-dichlorobenzyl | $C_{26}H_{34}Cl_2N_4O$<br>ESI 491 (86) 489 (100), 245 (72) |
| *isobutylaminopropyl* | indan-2-yl | $C_{28}H_{38}N_4O$<br>ESI 447 (88), 224 (100) |
| *isobutylaminopropyl* | 2-chlorobenzyl | $C_{26}H_{35}ClN_4O$<br>ESI 455 (100), 228 (85) |
| *n-butylaminopropyl* | 2-chlorobenzyl | $C_{26}H_{35}ClN_4O$<br>ESI 455 (100), 228 (60) |
| *ethylaminopropyl* | 2-chlorobenzyl | $C_{24}H_{31}ClN_4O$<br>ESI 427 (100), 303 (10), 214 (48) |

TABLE 6-continued
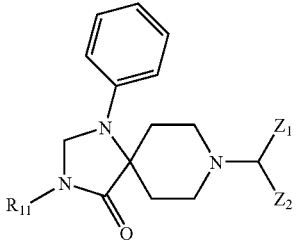
wherein R[11], Z[1] and Z[2] are as defined in the following table:
| R[11] | CH(Z[1])(Z[2]) | Physical Data |
|---|---|---|
| 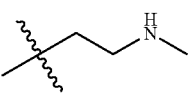 |  | $C_{23}H_{29}BrN_4O$<br>ESI 459 (99), 457 (100), 230 (45) |
| 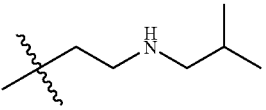 | 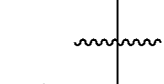 | $C_{26}H_{35}BrN_4O$<br>FAB 501 (99), 499 (100), 235 (40) |
| 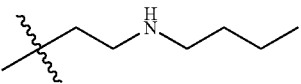 |  | $C_{26}H_{35}BrN_4O$<br>FAB 501 (99), 499 (100), 171 (28) |
| 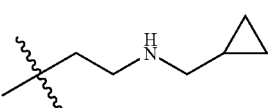 | 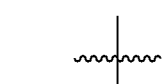 | $C_{26}H_{35}BrN_4O$<br>FAB 499 (99), 497 (100), 171 (20) |
| 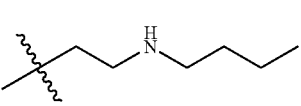 |  | $C_{26}H_{33}FN_4O$<br>FAB 439 (100), 220 (7) |
| 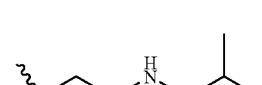 |  | $C_{26}H_{35}FN_4O$<br>FAB 439 (100), 220 (40) |

TABLE 6-continued

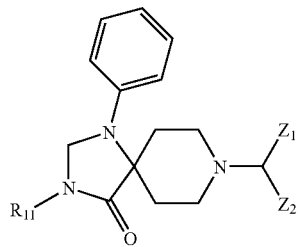

wherein R$^{11}$, Z$^1$ and Z$^2$ are as defined in the following table:

| R$^{11}$ | CH(Z$^1$)(Z$^2$) | Physical Data |
|---|---|---|
| H | phenethyl | C$_{21}$H$_{25}$N$_3$O<br>FAB 336 (100), 171 (100) |
| CH$_2$CH$_2$CH$_2$NHCH$_3$ | 2-fluorobenzyl | C$_{23}$H$_{29}$FN$_4$O<br>FAB 397 (100), 242 (100) |
| CH$_2$CH$_2$CH$_2$NHCH$_2$CH$_3$ | 2-fluorobenzyl | C24H31FN4O<br>FAB 411 (100), 242 (90) |
| H | cyclohexylmethyl | C$_{19}$H$_{27}$N$_3$O<br>FAB 314 (100), 247 (7) |
| CH$_2$CH$_2$CH$_2$NHCH$_2$CH$_2$CH$_2$CH$_3$ | 5-fluoro-1,2,3,4-tetrahydronaphthalen-1-yl | C$_{29}$H$_{39}$FN$_4$O<br>ESI 479.1(100), 424.1 (31), 331.1 (43), 203.1 (61) |
| CH$_2$CH$_2$CH$_2$NHCH$_2$CH$_2$CH$_2$CH$_3$ | 7-fluoro-1,2,3,4-tetrahydronaphthalen-1-yl | C$_{29}$H$_{39}$FN$_4$O<br>ESI 479.1 (100), 424.1 (11), 331.1 (39), 203.1 (38) |

TABLE 6-continued

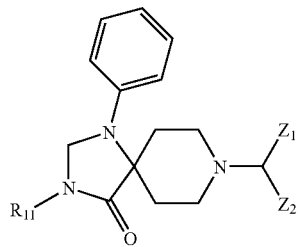

wherein R$^{11}$, Z$^1$ and Z$^2$ are as defined in the following table:

| R$^{11}$ | CH(Z$^1$)(Z$^2$) | Physical Data |
|---|---|---|
| ~~~NH-butyl | 5-chloro-1,2,3,4-tetrahydronaphthalen-1-yl | C$_{29}$H$_{39}$ClN$_4$O<br>ESI 495.1 (70), 345.1 (37), 65.0 (100) |
| H | naphthalen-2-ylmethyl | C$_{24}$H$_{25}$N$_3$O<br>ESI 372.1 (100), 200.1 (4) |
| ~~~NH-butyl | naphthalen-2-ylmethyl | C$_{30}$H$_{38}$N$_4$O<br>ESI 471.1 (100), 331.1 (36) |
| H | cyclohexylmethyl | C$_{20}$H$_{29}$N$_3$O<br>ESI 328 (100) |
| H | 2-cyclohexylethyl | C$_{21}$H$_{31}$N$_3$O<br>ESI 342 (100) |
| H | cyclooctylmethyl | C$_{22}$H$_{33}$N$_3$O<br>ESI 356.1 (100), 171.1 (5) |

TABLE 6-continued

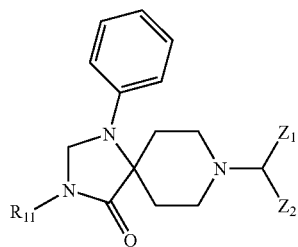

wherein $R^{11}$, $Z^1$ and $Z^2$ are as defined in the following table:

| $R^{11}$ | $CH(Z^1)(Z^2)$ | Physical Data |
|---|---|---|
| (isopropyl-ethyl group) | (cyclooctylmethyl group) | $C_{24}H_{37}N_3O$<br>ESI 370.1 (100), 247.1 (20) |

TABLE 7 compounds of the formulas shown, wherein Ph is phenyl

| Compound | Physical Data |
|---|---|
| (3-methyl-4-hydroxy-4-phenyl-1-benzhydryl-piperidine stereoisomer) | $C_{25}H_{27}NO\cdot HCl$<br>ESI 358.1 (44.50), 167.0 (100) |
| (3-methyl-4-hydroxy-4-phenyl-1-benzhydryl-piperidine stereoisomer) | $C_{25}H_{27}NO\cdot HCl$<br>FAB 358.2 (100), 232.1 (23.70) |
| (azabicyclic alcohol with phenyl and benzhydryl) | $C_{27}H_{29}NO\cdot HCl$<br>Cl 348.20 (58), 366.25 (23.70) |
| (azabicyclic alcohol with phenyl and benzhydryl) | $C_{26}H_{27}NO\cdot HCl$<br>FAB 370.1 (100), 167.0 (100) |

TABLE 7-continued compounds of the formulas shown, wherein Ph is phenyl

| Compound | Physical Data |
|---|---|
| (structure with 2-methylphenyl, bicyclic amine, OH, Ph) | $C_{28}H_{31}NO \cdot HCl$<br>FAB 398.1 (100), 195.1 (98) |
| (structure with 2-chlorophenyl, bicyclic amine, OH, Ph) | $C_{26}H_{25}NOCl_2 \cdot HCl$<br>FAB 440.1 (65), 438.0 (100), 236.9 (38), 234.9 (60) |
| (phthalide spiropiperidine with CHPh$_2$) | $C_{25}H_{23}NO_2 \cdot HCl$<br>FAB 370.2 (100), 292.2 (18) |
| (isobenzofuran spiropiperidine with CHPh$_2$) | $C_{25}H_{25}NO \cdot HCl$<br>ESI 356.1 (14.77), 168 (20.98), 167 (100) |
| (indane spiropiperidine with CHPh$_2$) | $C_{26}H_{27}N \cdot HCl$<br>ESI 354.1 (55.06), 167.1 (100), |
| (indene spiropiperidine with CHPh$_2$) | $C_{26}H_{25}NO \cdot HCl$<br>ESI 352.1 (41.94), 167.1 (100) |
| (hydroxy isobenzofuran spiropiperidine with CHPh$_2$) | $C_{25}H_{25}NO_2 \cdot HCl$<br>ESI 372.1 (15.42), 167 (100) |

TABLE 7-continued compounds of the formulas shown, wherein Ph is phenyl

| Compound | Physical Data |
|---|---|
| [structure] | $C_{26}H_{27}NO_2$·HCl<br>Cl 386.10 (73), 354.05 (88), 167.25 (100). |
| [structure] | $C_{25}H_{24}N_3Cl$·HCl<br>Cl 402 (55), 366.20 (77), 250.15 (34), 167.25 (74). |
| [structure] | $C_{25}H_{26}N_2$<br>Cl 356.2 (26) 355.2 (100), 167 (28) |
| [structure] | $C_{26}H_{25}N_3O_2$:HCl<br>ESI 412 (20), 167.1 (100) |
| [structure] | $C_{26}H_{25}F_2NO$<br>ESI 406.1 (100), 203.1 (89.11) |
| [structure] | $C_{26}H_{26}ClNO$<br>ESI 406.1 (34.35), 404.10 (81.42), 201.10 (100) |

TABLE 7-continued compounds of the formulas shown, wherein Ph is phenyl

| Compound | Physical Data |
|---|---|
| (structure) | C$_{27}$H$_{29}$NO<br>ESI 384.1 (54.52), 181 (100) |
| (structure) | C$_{27}$H$_{28}$Cl$_2$N$_2$O<br>ESI 399.1 (13.87), 398.1 (56.98),<br>397.1 (100) |
| (structure) | C$_{26}$H$_{26}$FNO<br>ESI 388.2 (90), 185.0 (100) |
| (structure) | C$_{29}$H$_{34}$N$_2$O<br>ESI 429.1 (8.33), 428.10 (36.55),<br>427.1 (74.28) |
| (structure) | C$_{24}$H$_{31}$NO<br>FAB 350.4 (100), 204.3 (18) |

TABLE 7-continued compounds of the formulas shown, wherein Ph is phenyl

| Compound | Physical Data |
|---|---|
| (structure with OH, N-CH(Ph)(CH₂)₄CH₃, phenyl) | $C_{25}H_{33}NO$<br>FAB 364.40 (100), 204.3 (20) |
| (structure with OH, 2-F-phenyl groups, CH₂NH₂) | $C_{27}H_{28}F_2N_2O$<br>FAB 435.2 (100), 203.1 (55) |
| (structure with OH, phenyl, N-CH(Ph)(2-Br-phenyl)) | $C_{26}H_{26}BrNO$<br>FAB 448.1 (100), 247.0 (58), 166.1 (38) |
| (structure with OH, phenyl, N-CH(2-Br-phenyl)₂) | $C_{26}H_{25}Br_2NO$<br>ESI 528 (100), 325.1 (54.35) |
| (structure with OH, CH₂NH₂-phenyl, N-CH(2-Br-phenyl)₂) | $C_{27}H_{28}Br_2N_2O$<br>FAB 560 (20), 557 (100), 324.8 (60) |

TABLE 7-continued
compounds of the formulas shown, wherein Ph is phenyl
| Compound | Physical Data |
|---|---|
| 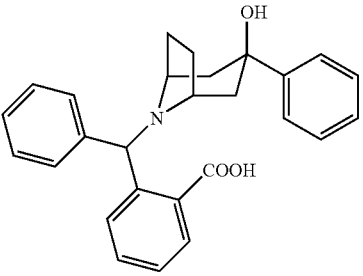 | $C_{27}H_{27}NO_3$<br>CI 414.20 (100), 396.20 (34), 211.15 (47), 186.15 (30) |
| 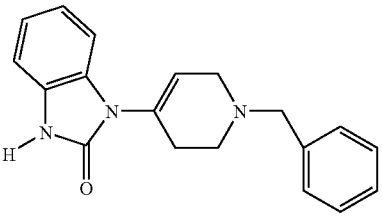 | $C_{19}H_{19}N_3O$<br>ESI 306.1 (100) |
| 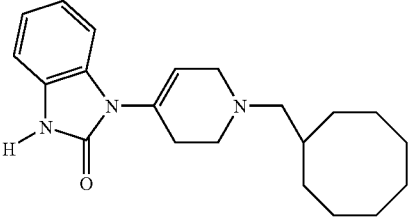 | $C_{21}H_{29}N_3O$<br>ESI 341.1 (30.27), 340.1 (100) |
| 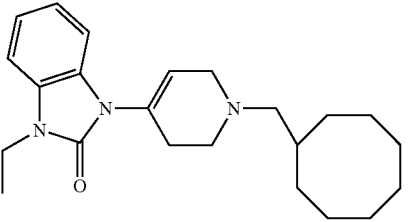 | $C_{23}H_{33}N_3O$<br>ESI 369.1 (39.66), 368.1 (100) |
| 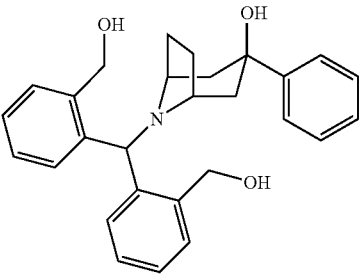 | $C_{28}H_{31}NO_3$<br>ESI 430.1 (100), 204.1 (52.46) |

TABLE 7-continued
compounds of the formulas shown, wherein Ph is phenyl
| Compound | Physical Data |
|---|---|
| 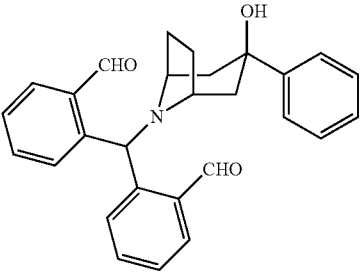 | $C_{28}H_{27}NO_3$<br>FAB 426.3 (100), 225.0 (18), 195 (18) |
| 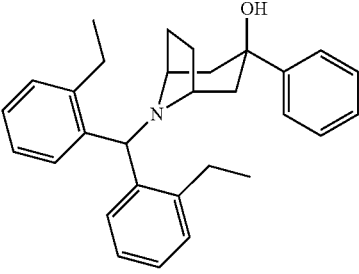 | $C_{30}H_{35}NO$<br>ESI 426.1 (100), 408 (11), 223.0 (43) |
| 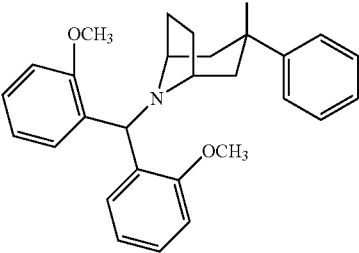 | $C_{28}H_{31}NO_3$<br>ESI 430.1 (100), 412.1 (11.0), 227.0 (24.2) |
| 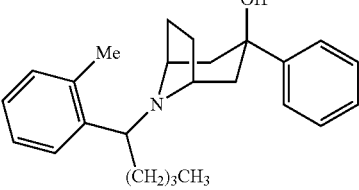 | $C_{25}H_{33}NO$<br>ESI 364.10 (100), 346 (7) |
| 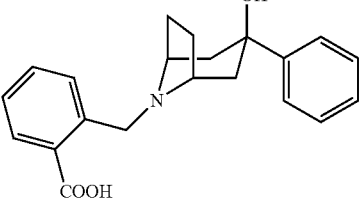 | $C_{21}H_{23}NO_3$<br>FAB 338.1 (100) |
| 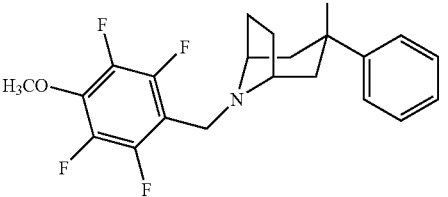 | $C_{21}H_{21}F_4NO_2$<br>ESI 396.1 (100) |

TABLE 7-continued
compounds of the formulas shown, wherein Ph is phenyl
| Compound | Physical Data |
|---|---|
| 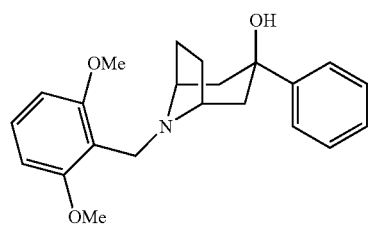 | $C_{22}H_{27}NO_3$<br>CI 354 (100), 336 (78) |
| 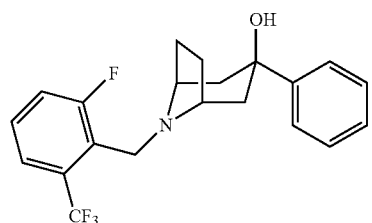 | $C_{21}H_{21}F_4NO$<br>ESI 380.1 (100) |
TABLE 8
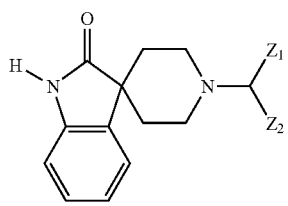
wherein $Z^1$ and $Z^2$ are as defined in the following table:
| $Z^1$ | $Z^2$ | Physical Data |
|---|---|---|
| 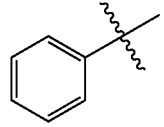 | 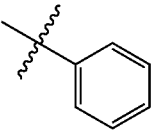 | $C_{25}H_{24}N_2O\cdot HCl$<br>FAB 369.2 (75), 167.1 (100) |
| 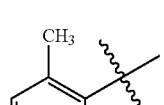 | 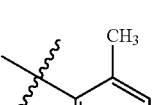 | $C_{27}H_{28}N_2O\cdot HCl$<br>FAB 397.2 (40), 195.1 (100) |
| 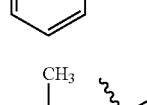 | 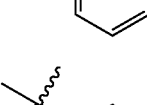 | $C_{26}H_{26}N_2O\cdot HCl$<br>ESI 383.1 (11.64), 181.1 (100) |
| 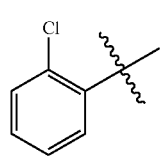 | 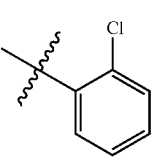 | $C_{25}H_{24}N_2Cl_2O\cdot HCl$<br>ESI 441.1 (11.05), 440.1 (15.61),<br>439.1 (48.02), 438.1 (23.94), 437.1<br>(64.05), 235.1 (100) |

TABLE 8-continued

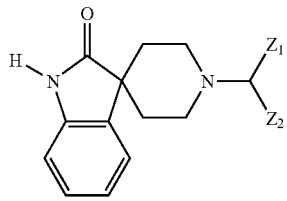

wherein $Z^1$ and $Z^2$ are as defined in the following table:

| $Z^1$ | $Z^2$ | Physical Data |
|---|---|---|
| 2-F-C6H4-CH(CH3)- | 2-F-C6H4-CH(CH3)- | $C_{25}H_{22}N_2OF_2 \cdot HCl$<br>FAB 405.2 (100), 203.1 (76) |
| 2-Cl-C6H4-CH(CH3)- | C6H5-CH2- | $C_{25}H_{23}ClN_2O \cdot HCl$<br>FAB 403.1 (100) 201 (70) |

ASSAYS

Nociceptin Binding Assay

CHO cell membrane preparation expressing the ORL-1 receptor (2 mg) was incubated with varying concentrations of [$^{125}$I][Tyr$^{14}$]nociceptin (3–500 pM) in a buffer containing 50 mM HEPES (pH7.4), 10 mM NaCl, 1 mM $MgCl_2$, 2.5 mM $CaCl_2$, 1 mg/ml bovine serum albumin and 0.025% bacitracin. In a number of studies, assays were carried out in buffer 50 mM tris-HCl (pH 7.4), 1 mg/ml bovine serum alumbin and 0.025% bacitracin. Samples were incubated for 1 h at room temperature (22° C.). Radiolabelled ligand bound to the membrane was harvested over GF/B filters presoaked in 0.1% polyethyleneimine using a Brandell cell harvester and washed five times with 5 ml cold distilled water. Nonspecific binding was determined in parallel by similar assays performed in the presence of 1 μM nociceptin. All assay points were performed in duplicates of total and non-specific binding.

Calculations of Ki were made using methods well known in the art.

For compounds of this invention, Ki values were determined to be in the range of 0.6 to 3000 nM, with compounds having a Ki value less than 10 nM being preferred. Ki values for representative compounds of the invention are as follows:

| Compounds | Ki (nM) |
|---|---|
| [4-phenyl-4-hydroxypiperidine with N-CHPh2] | 13 |
| [4-phenyl-4-amino piperidine with N-CHPh2] | 200 |
| [4-(4-bromophenyl)-4-hydroxypiperidine with N-CHPh2] | 60 |
| [4-(2-aminomethylphenyl)-4-hydroxypiperidine with N-CH(2-Cl-C6H4)2] | 0.6 |
| [bicyclic amine with OH, Ph and N-CHPh2] | 2.3 |

-continued
| Compounds | Ki (nM) |
|---|---|
| 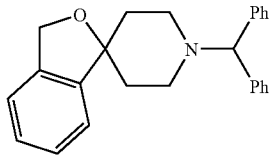 | 77 |
| 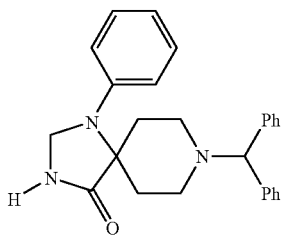 | 18 |
-continued
| Compounds | Ki (nM) |
|---|---|
| 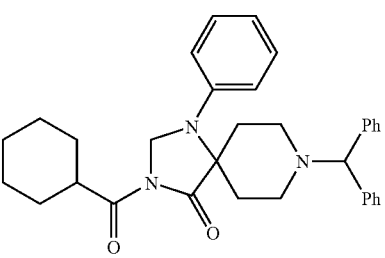 | 3,000 |
Using the procedures described the *European Journal of Pharmacology*, 336 (1997), p. 233–242, the agonist activity of compounds of the invention was determined:
| Compound | % Stimulation of [$^{35}$S]-GTPγS binding to human ORL-1 receptor @ 100 nM |
|---|---|
| 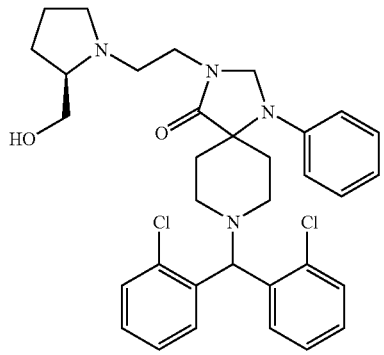 | 77 |
| 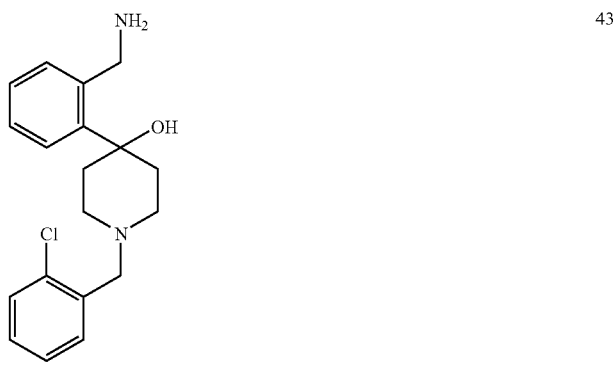 | 43 |

-continued
| Compound | % Stimulation of [$^{35}$S]-GTPγS binding to human ORL-1 receptor @ 100 nM |
|---|---|
| 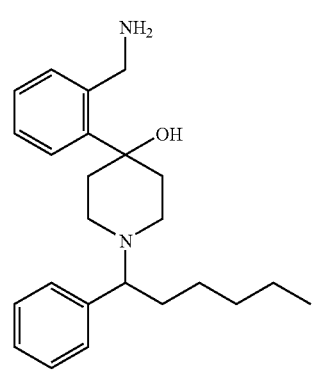 | 59 |
| 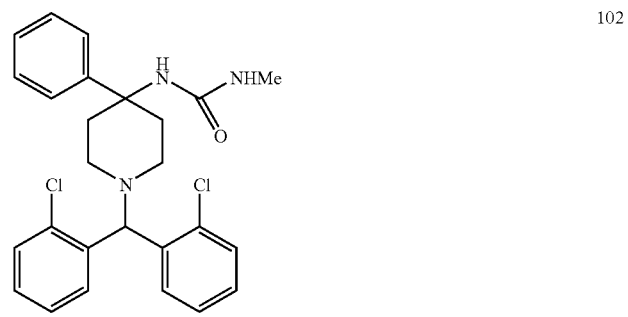 | 102 |
| 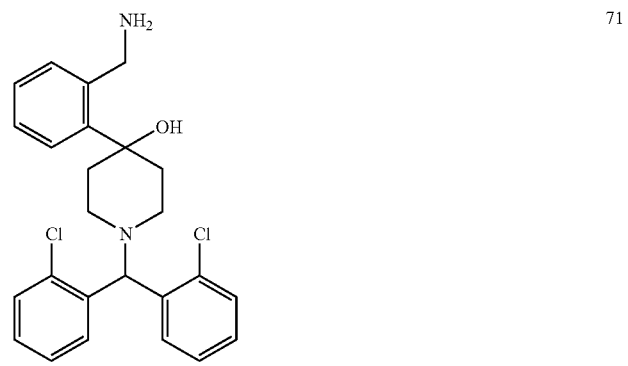 | 71 |
| 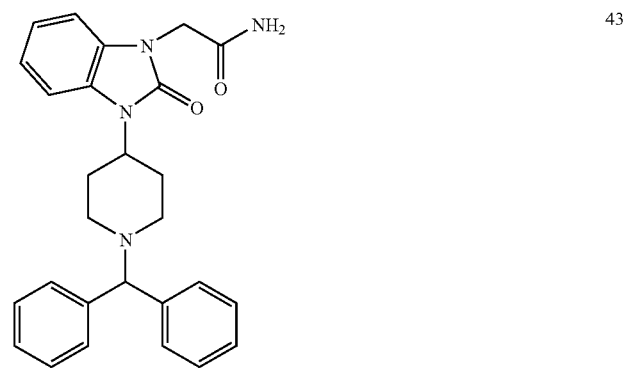 | 43 |

-continued
| Compound | % Stimulation of [$^{35}$S]-GTPγS binding to human ORL-1 receptor @ 100 nM |
|---|---|
| 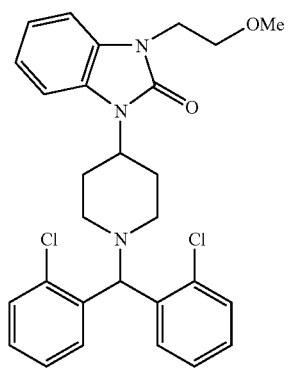 | 15 |
| 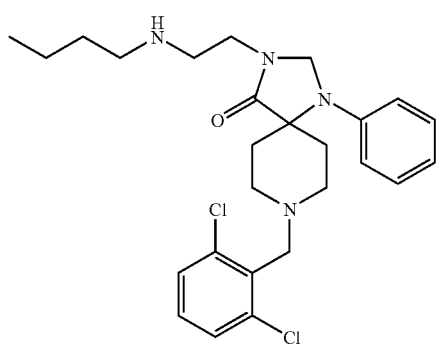 | 95 |
| 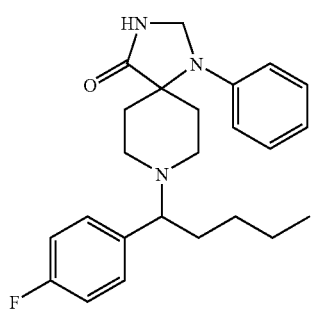 | 107 |
| 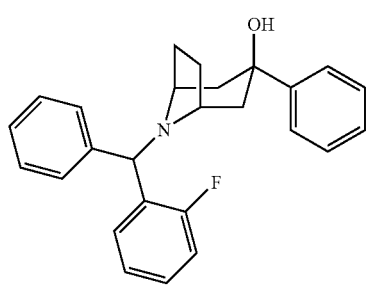 | 120 |

-continued

| Compound | % Stimulation of [$^{35}$S]-GTPγS binding to human ORL-1 receptor @ 100 nM |
|---|---|
| 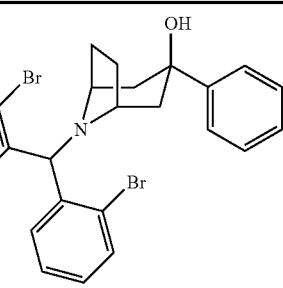 | 70 |
| 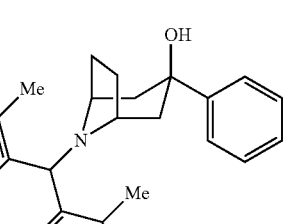 | 101 |

EXAMPLE 12

Cough Studies

The effects of nociceptin agonist Compound A (0.3–10 mg/kg, p.o.) and Compound B (10 mg/kg, p.o.)

COMPOUND A

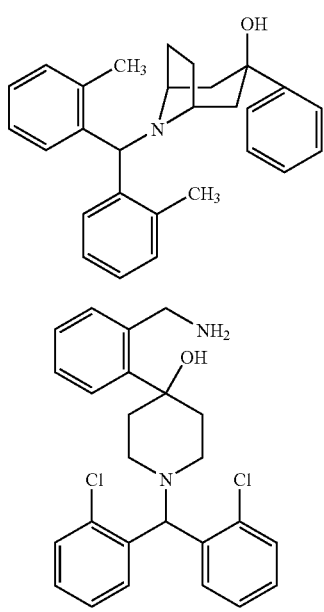

COMPOUND B were evaluated in capsaicin-induced cough in the guinea pig according to the methods of Bolser et al. *British Journal of Pharmacology* (1995) 114, 735–738. This model is a widely used method to evaluate the activity of potential antitussive drugs. Overnight fasted male Hartley guinea pigs (350–450 g, Charles River, Bloomington, Mass., USA) were placed in a 12"×14" transparent chamber. The animals were exposed to aerosolized capsaicin (300 μM, for 4 min) produced by a jet nebulizer (Puritan Bennett, Lenexa, Kans., USA) to elicit the cough reflex. Each guinea pig was exposed only once to capsaicin. The number of coughs were detected by a microphone placed in the chamber and verified by a trained observer. The signal from the microphone was relayed to a polygraph which provided a record of the number of coughs. Either vehicle (methylcellulose 1 ml/kg, p.o.) or Compound A or Compound B were given 2 hours before aerosolized capsaicin. The antitussive activity of baclofen (3 mg/kg, p.o.) was also tested as a positive control. The results are summarized in the bar graph in FIG. 1.

EXAMPLE 13

Respiratory Measurements

Studies were performed on male Hartley guinea pigs ranging in weight from 450 to 550 g. The animals were fasted overnight but given water and libitum. The guinea pigs were placed in a whole-body, head-out plethysmograph and a rubber collar was placed over the animal's head to provide an airtight seal between the guinea pig and the plethysmograph. Airflow was measured as a differential pressure across a wire mesh screen which covered a 1-in hole in the wall of the plethysmograph. The airflow signal was integrated to a signal proportional to volume using a preamplifier circuit and a pulmonary function computer (Buxco Electronics, Sharon, Conn., model XA). A head chamber was attached to the plethysmograph and air from a compressed gas source (21% $O_2$, balance $N_2$) was circulated through the head chamber for the duration of study. All respiratory measurements were made while the guinea pigs breathed this circulating air.

The volume signal from each animal was fed into a data acquisition/analysis system (Buxco Electronics, model XA)

that calculated tidal volume and respiratory rate on a breath-by-breath basis. These signals were visually displayed on a monitor. Tidal volume and respiratory rate were recorded as an average value every minute.

The guinea pigs were allowed to equilibrate in the plethysmograph for 30 min. Baseline measurements were obtained at the end of this 30 min period. The guinea pigs were then removed from the plethysmograph and orally dosed with Compound A from Example 12 (10 mg/kg, p.o.), baclofen (3 mg/kg, p.o.) or a methylcellulose vehicle placebo (2 ml/kg, p.o.). Immediately after dosing, the guinea pigs were placed into the plethysmograph, the head chamber and circulating air were reconnected and respiratory variables were measured at 30, 60, 90 and 120 min post treatment. This study was performed under ACUC protocol #960103.

Data Analysis

Figure 2A:
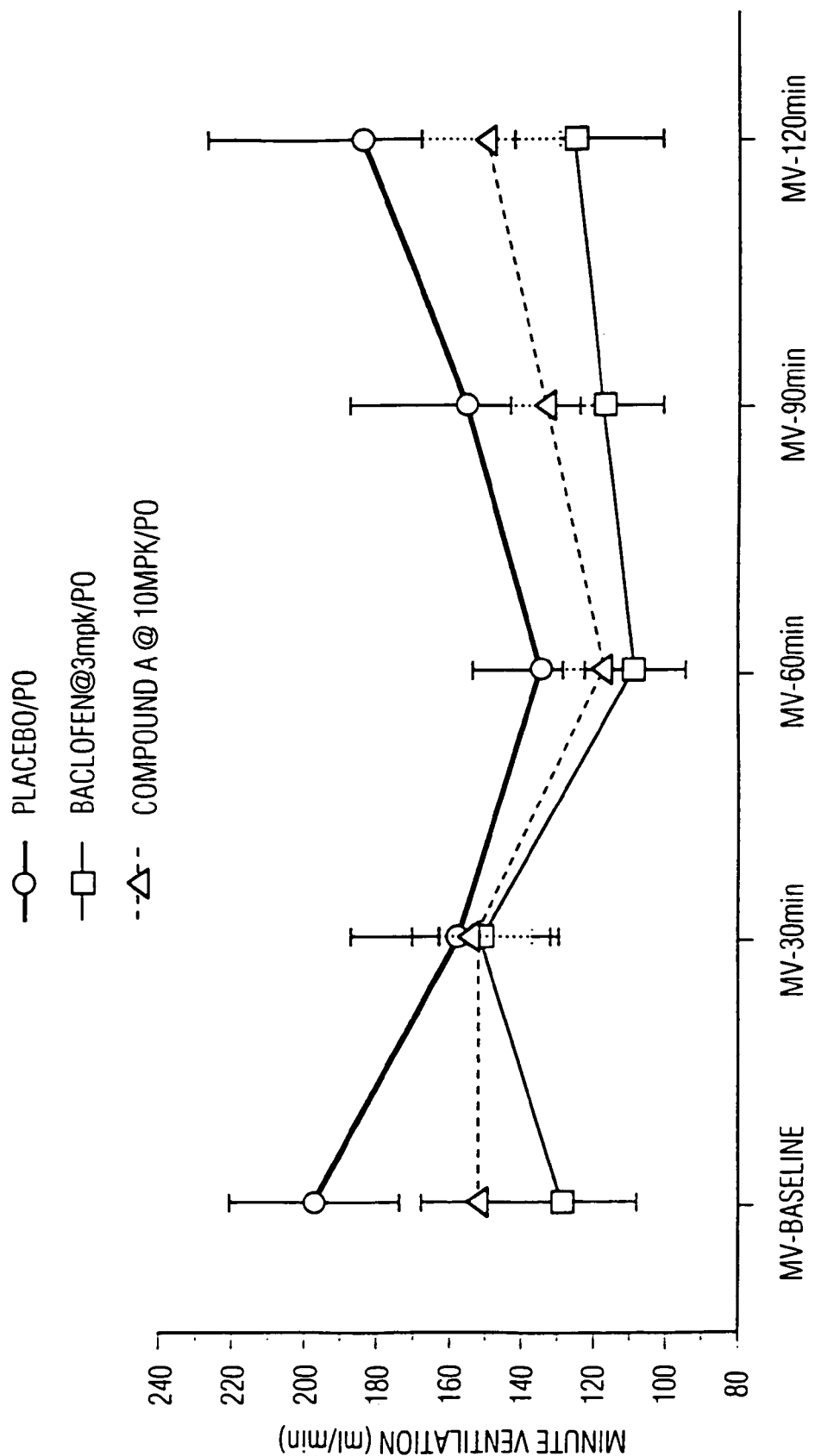
FIGS. 2A and 2B show changes in Tidal Volume after administration of Compound A or baclofen.
Figure 2B:
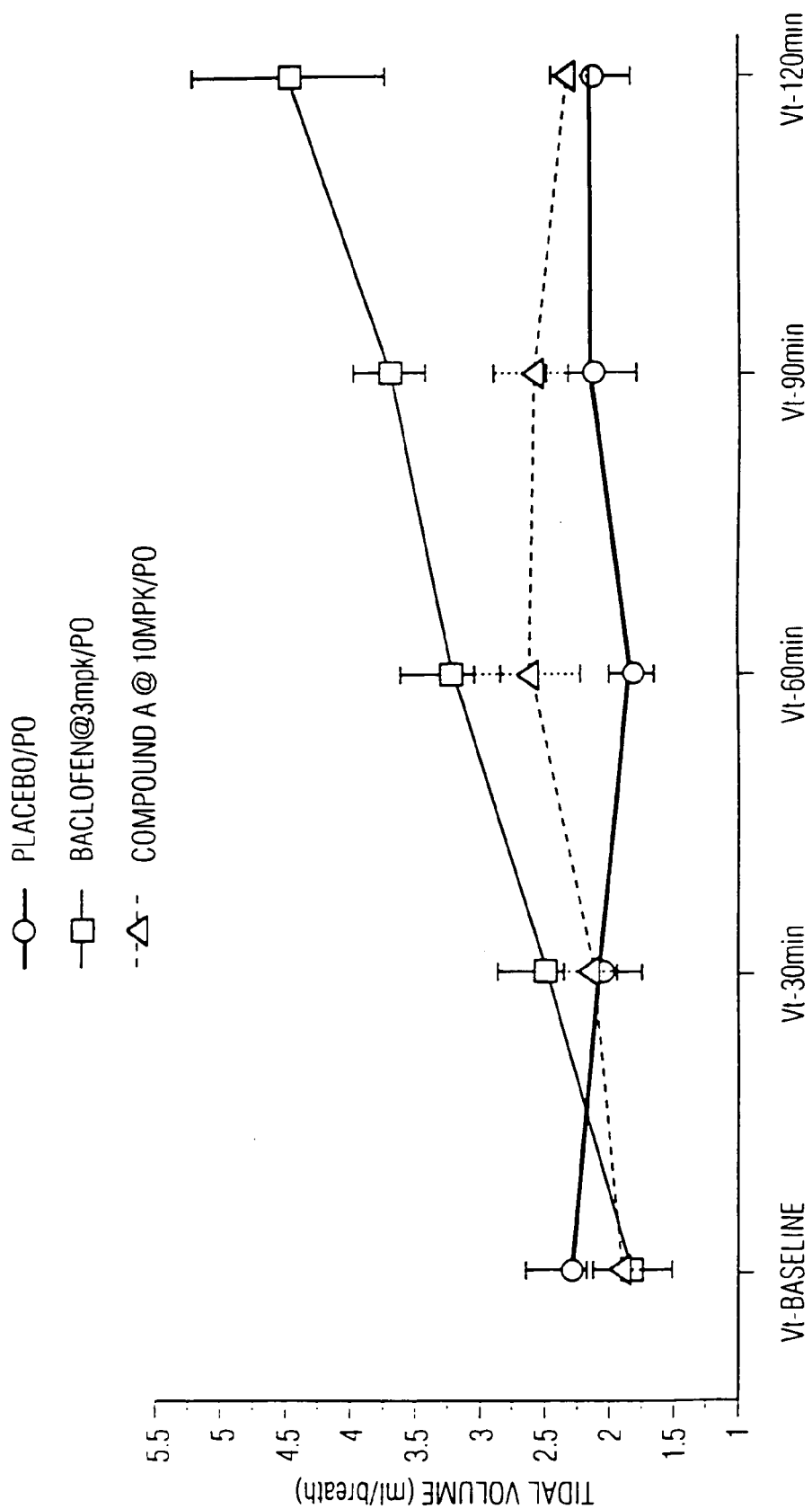
Figure 2C:
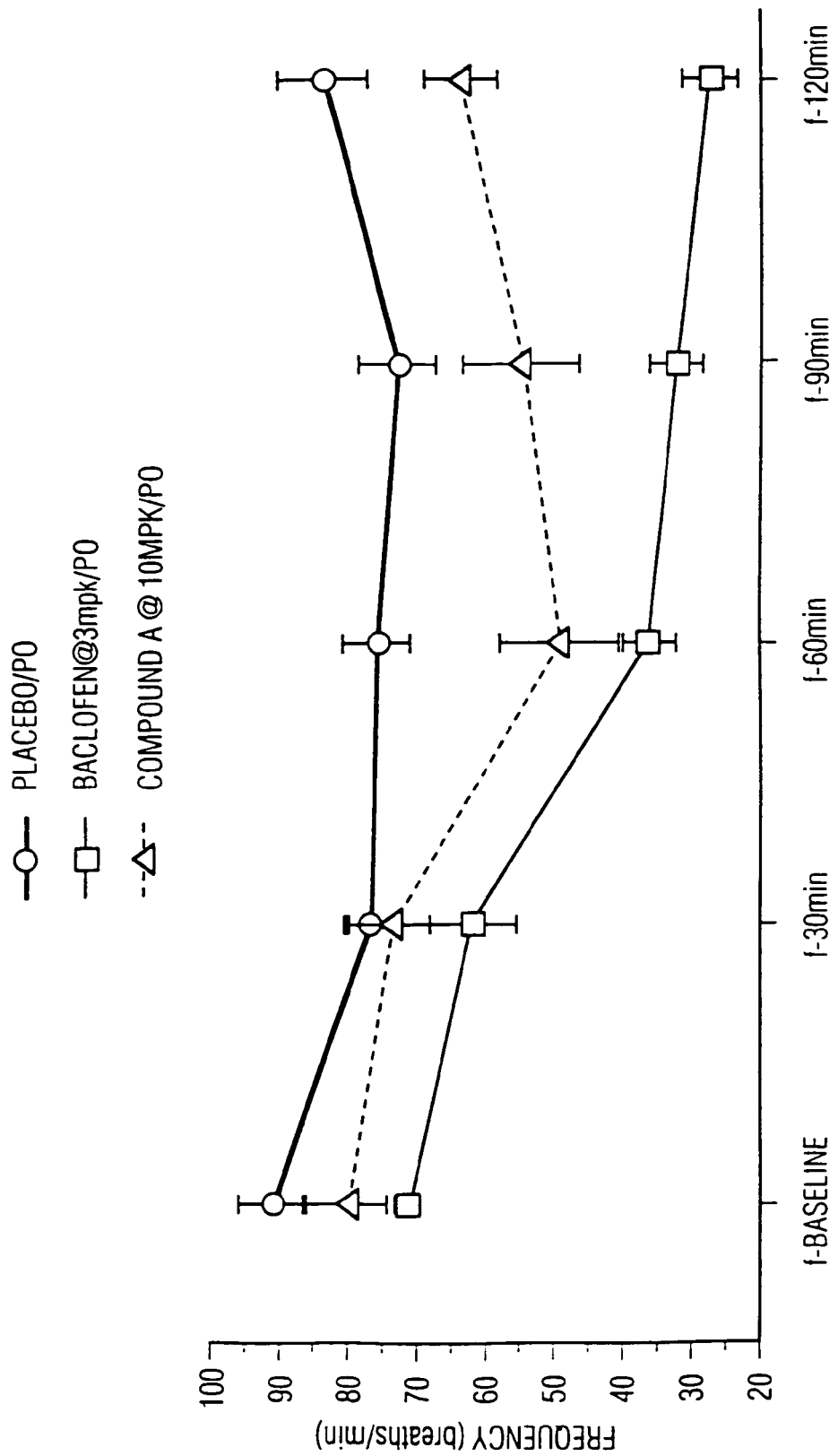
FIG. 2C shows changes in frequency of breaths after administration of Compound A or baclofen.

The data for tidal volume ($V_T$), respiratory rate (f) and minute volume ($MV = V_T \times f$) were made for the baseline condition and at each time point after the drug or vehicle. The results are expressed as the mean ±SEM. The results are shown in FIGS. 2A, 2B and 2C. FIG. 2A shows the change in Tidal Volume, FIG. 2B shows the change in Tidal Volume and FIG. 2C shows the change in frequency of breaths.

We have surprisingly discovered that nociceptin receptor ORL-1 agonists exhibit anti-tussive activity, making them useful for suppressing coughing in mammals. Non-limitative examples of nociceptin receptor ORL-1 agonists include the nociceptin receptor ORL-1 agonist compounds described herein. For mammals treated for coughing, the nociceptin receptor ORL-1 agonists may be administered along with one or more additional agents for treating cough, allergy or asthma symptoms selected from antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, antitussives, expectorants, $NK_1$, $NK_2$ and $NK_3$ tachykinin receptor antagonists, and $GABA_B$ agonists.

Non limitative examples of antihistamines include: astemizole, azatadine, azelastine, acrivastine, brompheniramine, certirizine, chlorpheniramine, clemastine, cyclizine, carebastine, cyproheptadine, carbinoxamine, descarboethoxyloratadine (also known as SCH-34117), doxylamine, dimethindene, ebastine, epinastine, efletirizine, fexofenadine, hydroxyzine, ketotifen, loratadine, levocabastine, mizolastine, equitazine, mianserin, noberastine, meclizine, norastemizole, picumast, pyrilamine, promethazine, terfenadine, tripelennamine, temelastine, trimeprazine and triprolidine.

Non-limitative examples of histamine $H_3$ receptor antagonists include: thioperamide, impromidine, burimamide, clobenpropit, impentamine, mifetidine, S-sopromidine, R-sopromidine, SKF-91486, GR-175737, GT-2016, UCL-1199 and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two-$H_3$-Histamine Receptor Subtypes," *Molecular Pharmacology*, Vol. 38, pages 610–613 (1990).

The term "leukotriene inhibitor" includes any agent or compound that inhibits, restrains, retards or otherwise interacts with the action or activity of leukotrienes. Non-limitative examples of leukotriene inhibitors include montelukast [R-(E)]-1[[[1-[3-[2-(7-Chloro-2-quinolinyl)-ethenyl] phenyl]-3[2-(1-hydroxy-1-methylethyl)phenyl]propyl]thio]methyl]cyclo-propaneacetic acid and its sodium salt, described in EP 0 480 717; 1-(((R)-(3-(2-(6,7-difluoro-2-quinolinyl) ethenyl)phenyl)-3-(2-(2-hydroxy-2-propyl)phenyl)thio) methylcyclopropaneacetic acid, and its sodium salt, described in WO 97/28797 and U.S. Pat. No. 5,270,324; 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, and its sodium salt, described in WO 97/28797 and U.S. Pat. No. 5,472,964; praniukast, N-[4-oxo-2-(1H-tetrazol-5-yl)-4H-1-benzopyran-8-yl]-p-(4-phenylbutoxy)benzamide) described in WO 97/28797 and EP 173,516; zafirlukast, (cyclopentyl-3-[2-methoxy-4-[(o-tolylsulfonyl) carbamoyl]benzyl]-1-methylindole-5-carbamate) described in WO 97/28797 and EP 199,543; and [2-[[2(4-tert-butyl-2-thiazolyl)-5-benzofuranyl]oxymethyl]phenyl]acetic acid, described in U.S. Pat. No. 5,296,495 and Japanese patent JP08325265 A.

The term "5-lipoxygenase inhibitor" or "5-LO inhibitor" includes any agent or compound that inhibits, restrains, retards or otherwise interacts with the enzymatic action of 5-lipoxygenase. Non-limitative examples of 5-lipoxygenase inhibitors include zileuton, docebenone, piripost, ICI-D2318, and ABT 761.

Non-limitative examples of β-adrenergic receptor agonists include: albuterol, bitolterol, isoetharine, mataproterenol, perbuterol, salmeterol, terbutaline, isoproterenol, ephedrine and epinephrine.

A non-limitative example of a xanthine derivative is theophylline.

Non-limitative examples of α-adrenergic receptor agonists include arylalkylamines, (e.g., phenylpropanolamine and pseudephedrine), imidazoles (e.g., naphazoline, oxymetazoline, tetrahydrozoline, and xylometazoline), and cycloalkylamines (e.g., propylhexedrine).

A non-limitative example of a mast cell stabilizer is nedocromil sodium.

Non-limitative examples of anti-tussive agents include codeine, dextromethorphan, benzonatate, chlophedianol, and noscapine.

A non-limitative example of an expectorant is guaifenesin.

Non-limitative examples of $NK_1$, $NK_2$ and $NK_3$ tachykinin receptor antagonists include CP-99,994 and SR 48968.

Non-limitative examples of $GABA_B$ agonists include baclofen and 3-aminopropyl-phosphinic acid.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to provide relief from pain, anxiety, depression, asthma or alcohol abuse. The compounds are non-toxic when administered within this dosage range.

For treating cough, the amount of nociceptin receptor ORL-1 agonist in a unit dose is preferably from about 0.1 mg to 1000 mg, more preferably, from about 1 mg to 300 mg. A typical recommended dosage regimen is oral administration of from 1 mg to 2000 mg/day, preferably 1 to 1000 mg/day, in two to four divided doses. When treating coughing, the nociceptin receptor ORL-1 agonist may be administered with one or more additional agents for treating cough, allergy or asthma symptoms selected from the group consisting of: antihistamines, 5-lipoxygenase inhibitors, leukotriene inhibitors, $H_3$ inhibitors, $\beta$-adrenergic receptor agonists, xanthine derivatives, $\alpha$-adrenergic receptor agonists, mast cell stabilizers, anti-tussives, expectorants, $NK_1$, $NK_2$ and $NK_3$ tachykinin receptor antagonists, and $GABA_B$ agonists. The nociceptin receptor ORL-1 agonist and the additional agents are preferably administered in a combined dosage form (e.g., a single tablet), although they can be administered separately. The additional agents are administered in amounts effective to provide relief from cough, allergy or asthma symptoms, preferably from about 0.1 mg to 1000 mg, more preferably from about 1 mg to 300 mg per unit dose. A typical recommended dosage regimen of the additional agent is from 1 mg to 2000 mg/day, preferably 1 to 1000 mg/day, in two to four divided doses.

The following are examples of pharmaceutical dosage forms which contain a compound of the invention. The scope of the invention in its pharmaceutical composition aspect is not to be limited by the examples provided.

Pharmaceutical Dosage Form Examples

| EXAMPLE A Tablets | | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

METHOD OF MANUFACTURE

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

| EXAMPLE B Tablets | | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A pharmaceutical composition comprising: a therapeutically effective amount of a nociceptin receptor ORL-1 agonist of the formula

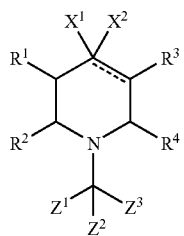

or a pharmaceutically acceptable salt or solvate thereof, wherein:

the dotted line represents an optional double bond;

$X^1$ is $R^5$—$(C_1-C_{12})$alkyl, $R^6$—$(C_3-C_{12})$cycloalkyl, $R^7$-aryl, $R^8$-heteroaryl or $R^{10}$—$(C_3-C_7)$heterocycloalkyl;

$X^2$ is —CHO, —CN, —NHC(=NR$^{26}$)NHR$^{26}$, —CH(=NOR$^{26}$), —NHOR$^{26}$, $R^7$-aryl, $R^7$-aryl$(C_1-C_6)$alkyl, $R^7$-aryl$(C_1-C_6)$alkenyl, $R^7$-aryl$(C_1-C_6)$-alkynyl, —(CH$_2$)$_v$OR$^{13}$, —(CH$_2$)$_v$COOR$^{27}$, —(CH$_2$)$_v$CONR$^{14}$R$^{15}$, —(CH$_2$)$_v$NR$^{21}$R$^{22}$ or —(CH$_2$)$_v$NHC(O)R$^{21}$, wherein v is zero, 1, 2 or 3 and wherein q is 1 to 3 and a is 1 or 2;

$R^1$ and $R^3$ are each hydrogen;

$R^2$ and $R^4$ together form an alkylene bridge of 1 to 3 carbon atoms;

$R^5$ is 1 to 3 substituents independently selected from the group consisting of H, $R^7$-aryl, $R^6$—$(C_3-C_{12})$cycloalkyl, $R^8$-heteroaryl, $R^{10}$—$(C_3-C_7)$heterocycloalkyl, —NR$^{19}$R$^{20}$, —OR$^{13}$ and —S(O)$_{0-2}$R$^{13}$;

$R^6$ is 1 to 3 substituents independently selected from the group consisting of H, $(C_1-C_6)$alkyl, $R^7$-aryl, —NR$^{19}$R$^{20}$, —OR$^{13}$ and —SR$^{13}$;

$R^7$ is 1 to 3 substituents independently selected from the group consisting of hydrogen, halo, $(C_1-C_6)$alkyl, $R^{25}$-aryl, $(C_3-C_{12})$cycloalkyl, —CN, —CF$_3$, —OR$^{19}$, —$(C_1-C_6)$alkyl-OR$^{19}$, —OCF$_3$, —NR$^{19}$R$^{20}$, —$(C_1-C_6)$alkyl-NR$^{19}$R$^{20}$, —NHSO$_2$R$^{19}$, —SO$_2$N(R$^{26}$)$_2$, —SO$_2$R$^{19}$, —SOR$^{19}$, —SR$^{19}$, —NO$_2$, —CONR$^{19}$R$^{20}$, —NR$^{20}$COR$^{19}$, —COR$^{19}$, —COCF$_3$, —OCOR$^{19}$, —OCO$_2$R$^{19}$, —COOR$^{19}$, —$(C_1-C_6)$alkyl-NHCOOC(CH$_3$)$_3$, —$(C_1-C_6)$alkyl-NHCOCF$_3$, —$(C_1-C_6)$alkyl-NHSO$_2$—$(C_1-C_6)$alkyl, —$(C_1-C_6)$alkyl-NHCONH—$(C_1-C_6)$-alkyl or

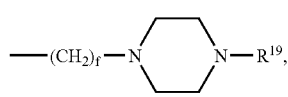

wherein f is 0 to 6; or $R^7$ substituents on adjacent ring carbon atoms may together form a methylenedioxy or ethylenedioxy ring;

$R^8$ is 1 to 3 substituents independently selected from the group consisting of hydrogen, halo, $(C_1-C_6)$alkyl, $R^{25}$-aryl, $(C_3-C_{12})$cycloalkyl, —CN, —CF$_3$, —OR$^{19}$, —$(C_1-C_6)$alkyl-OR$^{19}$, —OCF$_3$, —NR$^{19}$R$^{20}$, —$(C_1-C_6)$alkyl-NR$^{19}$R$^{20}$, —NHSO$_2$R$^{19}$, —SO$_2$N(R$^{26}$)$_2$, —NO$_2$, —CONR$^{19}$R$^{20}$, —NR$^{20}$COR$^{19}$, —COR$^{19}$, —OCOR$^{19}$, —OCO$_2$R$^{19}$ and —COOR$^{19}$;

$R^9$ is hydrogen, $(C_1-C_6)$alkyl, halo, —OR$^{19}$, —NR$^{19}$R$^{20}$, —NHCN, —SR$^{19}$ or —$(C_1-C_6)$alkyl-NR$^{19}$R$^{20}$;

$R^{10}$ is H, $(C_1-C_6)$alkyl, —OR$^{19}$, —$(C_1-C_6)$alkyl-OR$^{19}$, —NR$^{19}$R$^{20}$ or —$(C_1-C_6)$alkyl-NR$^{19}$R$^{20}$;

$R^{13}$ is H, $(C_1-C_6)$alkyl, $R^7$-aryl, —$(C_1-C_6)$alkyl-OR$^{19}$, —$(C_1-C_6)$alkyl-NR$^{19}$R$^{20}$ or —$(C_1-C_6)$alkyl-SR$^{19}$;

$R^{14}$ and $R^{15}$ are independently selected from the group consisting of H, $R^5$—$(C_1-C_6)$alkyl, $R^7$-aryl and

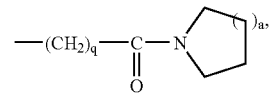

wherein q and a are as defined above;

$R^{19}$ and $R^{20}$ are independently selected from the group consisting of hydrogen, $(C_1-C_6)$alkyl, $(C_3-C_{12})$cycloalkyl, aryl and aryl$(C_1-C_6)$alkyl;

$R^{21}$ and $R^{22}$ are independently selected from the group consisting of hydrogen, $(C_1-C_6)$alkyl, $(C_3-C_{12})$cycloalkyl, $(C_3-C_{12})$cycloalkyl$(C_1-C_6)$alkyl, $(C_3-C_7)$heterocycloalkyl, —$(C_1-C_6)$alkyl$(C_3-C_7)$-heterocycloalkyl, $R^7$-aryl, $R^7$-aryl$(C_1-C_6)$alkyl, $R^8$-heteroaryl$(C_1-C_{12})$alkyl, —$(C_1-C_6)$alkyl-OR$^{19}$, —$(C_1-C_6)$alkyl-NR$^{19}$R$^{20}$, —$(C_1-C_6)$alkyl-SR$^{19}$, —$(C_1-C_6)$alkyl-NR$^{18}$—$(C_1-C_6)$alkyl-O—$(C_1-C_6)$alkyl and —$(C_1-C_6)$alkyl-NR$^{18}$—$(C_1-C_6)$alkyl-NR$^{18}$—$(C_1-C_6)$alkyl;

$R^{18}$ is hydrogen or $(C_1-C_6)$alkyl;

and $Z^1$ is $R^7$-aryl; $Z^2$ is $R^7$-aryl; $Z^3$ is hydrogen or $(C_1-C_3)$alkyl;

$R^{25}$ is 1–3 substituents independently selected from the group consisting of H, $(C_1-C_6)$alkyl, $(C_1-C_6)$alkoxy and halo;

$R^{26}$ is independently selected from the group consisting of H, $(C_1-C_6)$alkyl and $R^{25}$—$C_6H_4$—CH$_2$—;

$R^{27}$ is H, $(C_1-C_6)$alkyl, $R^7$-aryl$(C_1-C_6)$alkyl, or $(C_3-C_{12})$cycloalkyl; and a therapeutically effective amount of a second agent selected from the group consisting of: antihistamines, 5-lipoxygenase inhibitors, leukotriene inhibitors, H$_3$ inhibitors, β-adrenergic receptor agonists, xanthine derivatives, α-adrenergic receptor agonists, mast cell stabilizers, anti-tussives, expectorants, NK$_1$, NK$_2$ and NK$_3$ tachykinin receptor antagonists, and GABA$_B$ agonists; and a pharmaceutically acceptable carrier.

2. A method of treating cough comprising administering a combination of an effective amount of an ORL-1 agonist of the formula

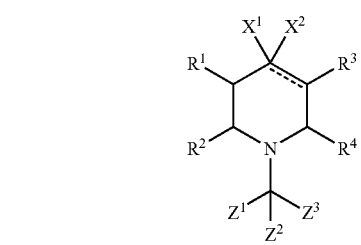

or a pharmaceutically acceptable salt or solvate thereof, wherein:

the dotted line represents an optional double bond;

$X^1$ is $R^5$—$(C_1-C_{12})$alkyl, $R^6$—$(C_3-C_{12})$cycloalkyl, $R^7$-aryl, $R^8$-heteroaryl or $R^{10}$—$(C_3-C_7)$heterocycloalkyl;

$X^2$ is —CHO, —CN, —NHC(=NR$^{26}$)NHR$^{26}$, —CH(=NOR$^{26}$), —NHOR$^{26}$, R$^7$-aryl, R$^7$-aryl(C$_1$–C$_6$)alkyl, R$^7$-aryl(C$_1$–C$_6$)alkenyl, R$^7$-aryl(C$_1$–C$_6$)-alkynyl, —(CH$_2$)$_v$OR$^{13}$, —(CH$_2$)$_v$COOR$^{27}$, —(CH$_2$)$_v$CONR$^{14}$R$^{15}$, —(CH$_2$)$_v$NR$^{21}$R$^{22}$ or —(CH$_2$)$_v$NHC(O)R$^{21}$, wherein v is zero, 1, 2 or 3 and wherein q is 1 to 3 and a is 1 or 2;

R$^1$ and R$^3$ are each hydrogen;

R$^2$ and R$^4$ together form an alkylene bridge of 1 to 3 carbon atoms;

R$^5$ is 1 to 3 substituents independently selected from the group consisting of H, R$^7$-aryl, R$^6$—(C$_3$–C$_{12}$)cycloalkyl, R$^8$-heteroaryl, R$^{10}$—(C$_3$–C$_7$)heterocycloalkyl, —NR$^{19}$R$^{20}$, —OR$^{13}$ and —S(O)$_{0-2}$R$^{13}$;

R$^6$ is 1 to 3 substituents independently selected from the group consisting of H, (C$_1$–C$_6$)alkyl, R$^7$-aryl, —NR$^{19}$R$^{20}$, —OR$^{13}$ and —SR$^{13}$;

R$^7$ is 1 to 3 substituents independently selected from the group consisting of hydrogen, halo, (C$_1$–C$_6$)alkyl, R$^{25}$-aryl, (C$_3$–C$_{12}$)cycloalkyl, —CN, —CF$_3$, —OR$^{19}$, —(C$_1$–C$_6$)alkyl-OR$^{19}$, —OCF$_3$, —NR$^{19}$R$^{20}$, —(C$_1$–C$_6$)alkyl-NR$^{19}$R$^{20}$, —NHSO$_2$R$^{19}$, —SO$_2$N(R$^{26}$)$_2$, —SO$_2$R$^{19}$, —SOR$^{19}$, —SR$^{19}$, —NO$_2$, —CONR$^{19}$R$^{20}$, —NR$^{20}$COR$^{19}$, —COR$^{19}$, —COCF$_3$, —OCOR$^{19}$, —OCO$_2$R$^{19}$, —COOR$^{19}$, —(C$_1$–C$_6$)alkyl-NHCOOC(CH$_3$)$_3$, —(C$_1$–C$_6$)alkyl-NHCOCF$_3$, —(C$_1$–C$_6$)alkyl-NHSO$_2$—(C$_1$–C$_6$)alkyl, —(C$_1$–C$_6$)alkyl-NHCONH—(C$_1$–C$_6$)-alkyl or

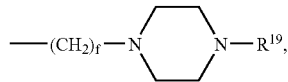

wherein f is 0 to 6; or R$^7$ substituents on adjacent ring carbon atoms may together form a methylenedioxy or ethylenedioxy ring;

R$^8$ is 1 to 3 substituents independently selected from the group consisting of hydrogen, halo, (C$_1$–C$_6$)alkyl, R$^{25}$-aryl, (C$_3$–C$_{12}$)cycloalkyl, —CN, —CF$_3$, —OR$^{19}$, —(C$_1$–C$_6$)alkyl-OR$^{19}$, —OCF$_3$, —NR$^{19}$R$^{20}$, —(C$_1$–C$_6$)alkyl-NR$^{19}$R$^{20}$, —NHSO$_2$R$^{19}$, —SO$_2$N(R$^{26}$)$_2$, —NO$_2$, —CONR$^{19}$R$^{20}$, —NR$^{20}$COR$^{19}$, —COR$^{19}$, —OCOR$^{19}$, —OCO$_2$R$^{19}$ and —COOR$^{19}$;

R$^9$ is hydrogen, (C$_1$–C$_6$)alkyl, halo, —OR$^{19}$, —NR$^{19}$R$^{20}$, —NHCN, —SR$^{19}$ or —(C$_1$–C$_6$)alkyl-NR$^{19}$R$^{20}$;

R$^{10}$ is H, (C$_1$–C$_6$)alkyl, —OR$^{19}$, —(C$_1$–C$_6$)alkyl-OR$^{19}$, —NR$^{19}$R$^{20}$ or —(C$_1$–C$_6$)alkyl-NR$^{19}$R$^{20}$;

R$^{13}$ is H, (C$_1$–C$_6$)alkyl, R$^7$-aryl, —(C$_1$–C$_6$)alkyl-OR$^{19}$, —(C$_1$–C$_6$)alkyl-NR$^{19}$R$^{20}$ or —(C$_1$–C$_6$)alkyl-SR$^{19}$;

R$^{14}$ and R$^{15}$ are independently selected from the group consisting of H, R$^5$—(C$_1$–C$_6$)alkyl, R$^7$-aryl and

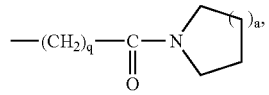

wherein q and a are as defined above;

R$^{19}$ and R$^{20}$ are independently selected from the group consisting of hydrogen, (C$_1$–C$_6$)alkyl, (C$_3$–C$_{12}$)cycloalkyl, aryl and aryl(C$_1$–C$_6$)alkyl;

R$^{21}$ and R$^{22}$ are independently selected from the group consisting of hydrogen, (C$_1$–C$_6$)alkyl, (C$_3$–C$_{12}$)cycloalkyl, (C$_3$–C$_{12}$)cycloalkyl(C$_1$–C$_6$)alkyl, (C$_3$–C$_7$)heterocycloalkyl, —(C$_1$–C$_6$)alkyl(C$_3$–C$_7$)-heterocycloalkyl, R$^7$-aryl, R$^7$-aryl(C$_1$–C$_6$)alkyl, R$^8$-heteroaryl(C$_1$–C$_{12}$)alkyl, —(C$_1$–C$_6$)alkyl-OR$^{19}$, —(C$_1$–C$_6$)alkyl-NR$^{19}$R$^{20}$, —(C$_1$–C$_6$)alkyl-SR$^{19}$, —(C$_1$–C$_6$)alkyl-NR$^{18}$—(C$_1$–C$_6$)alkyl-O—(C$_1$–C$_6$)alkyl and —(C$_1$–C$_6$)alkyl-NR$^{18}$—(C$_1$–C$_6$)alkyl-NR$^{18}$—(C$_1$–C$_6$)alkyl;

R$^{18}$ is hydrogen or (C$_1$–C$_6$)alkyl;

and Z$^1$ is R$^7$-aryl; Z$^2$ is R$^7$-aryl; Z$^3$ is hydrogen or (C$_1$–C$_3$)alkyl;

R$^{25}$ is 1–3 substituents independently selected from the group consisting of H, (C$_1$–C$_6$)alkyl, (C$_1$–C$_6$)alkoxy and halo;

R$^{26}$ is independently selected from the group consisting of H, (C$_1$–C$_6$)alkyl and R$^{25}$—C$_6$H$_4$—CH$_2$—;

R$^{27}$ is H, (C$_1$–C$_6$)alkyl, R$^7$-aryl(C$_1$–C$_6$)alkyl, or (C$_3$–C$_{12}$)cycloalkyl;

and an effective amount of second agent for treating cough, allergy or asthma symptoms selected from the group consisting of: antihistamines, 5-lipoxygenase inhibitors, leukotriene inhibitors, H$_3$ inhibitors, β-adrenergic receptor agonists, xanthine derivatives, α-adrenergic receptor agonists, mast cell stabilizers, anti-tussives, expectorants, NK$_1$, NK$_2$ and NK$_3$ tachykinin receptor antagonists, and GABA$^B$ agonists.

3. A method of claim 2 wherein Z$^1$ and Z$^2$ are each R$^7$-phenyl.

4. A method of claim 3 wherein R$^7$ is selected from the group consisting of (C$_1$–C$_6$)alkyl and halo.

5. A method of claim 2 wherein X$^1$ is R$^7$-aryl and X$^2$ is OH or —NHC(O)R$^{21}$.

6. A method of claim 5 wherein X$^1$ is R$^7$-phenyl.

\* \* \* \* \*